United States Patent
Wan et al.

(10) Patent No.: US 7,335,488 B2
(45) Date of Patent: Feb. 26, 2008

(54) FLUORESCENT PROTEINS

(75) Inventors: David Chi-Cheong Wan, Shatin (HK); Denis Tsz-Ming Ip, Shatin (HK)

(73) Assignee: The Chinese University of Hong Kong, Shatin, N.T. (HK)

( * ) Notice: Subject to any disclaimer, the term of this patent is extended or adjusted under 35 U.S.C. 154(b) by 534 days.

(21) Appl. No.: 10/406,618

(22) Filed: Apr. 2, 2003

(65) Prior Publication Data

US 2003/0219814 A1 Nov. 27, 2003

Related U.S. Application Data

(60) Provisional application No. 60/387,968, filed on Jun. 11, 2002, provisional application No. 60/370,598, filed on Apr. 5, 2002.

(51) Int. Cl.
C12P 21/06 (2006.01)
(52) U.S. Cl. ............... 435/69.1; 435/325; 435/320.1; 435/6; 435/252.3; 530/350; 536/23.1
(58) Field of Classification Search ............... 435/7.1, 435/6, 320.1, 325, 252; 536/23.1, 23.4
See application file for complete search history.

(56) References Cited

U.S. PATENT DOCUMENTS

| 5,491,084 | A | 2/1996 | Chalfie et al. |
|---|---|---|---|
| 6,027,881 | A | 2/2000 | Pavlakis et al. |
| 6,172,188 | B1 | 1/2001 | Thastrup et al. |
| 6,265,548 | B1 | 7/2001 | Pavlakis et al. |
| 6,747,137 | B1 * | 6/2004 | Weinstock et al. ......... 536/23.1 |
| 6,780,975 | B2 * | 8/2004 | Tsien et al. ................. 530/350 |

OTHER PUBLICATIONS

Tuddenham et al., Nucleic Acids Research, vol. 22, No. 17, pp. 3511-3533, 1994.*
Heim et al., PNAS, vol. 91, pp. 12501-12504, 1994.*
Cody et al. (Biochemistry, vol. 32, pp. 1212-1218, 1993).*
Carmichael, Gordon G., Nature, 418:379-380 (2002).
Chalfie, M., Tu, Yuan, Euskirchen, G., Ward, W.W., Prasher, D.C., Science, 263: 802-805 (1994).
Cody, C.W., Prasher, D.C., Westler, W.M., Prendergast, F.G. and Ward, W.W., 1993. Chemical structure of the hexapeptide chromophore of the *Aequorea* green-fluorescent protein. *Biochemistry*. 32: 1212-8.
Cormack, B., Valdivia, R. and Falkow, S., 1996. FACS-optimized mutants of the green fluorescent protein (GFP). *Gene*. 173: 33-38.
Delagrave, S., Hawtin, R., Silva, C., Yang, M. and Youvan, D., 1995. Red-shifted excitation mutants of the green fluorescent protein. *Biotechnology*. 13: 151-154.
Ehrig, T., O'Kane, D. and Prendergast, F., 1995. Green-fluorescent protein mutants with altered fluorescence excitation spectra. *FEBS Lett*. 367: 163-6.
Gage, et al., *J. Bacteriol*, 178:24: 7159-7166 (1996).
Heim, R., Cubitt, A. and Tsien, R., 1995. Improved green fluorescence. *Nature*. 373: 663-664.
Heim, R., Prasher, D.C. and Tsien, R.Y., 1994. Wavelength mutations and posttranslational autoxidation of green fluorescent protein. *Proceedings of the National Academy of Sciences of the United States of America*. 91: 12501-4.
Prasher, *Trends in Genetics* 11:320 (1995).
Prasher, D., Eckenrode, V., Ward, W., Prendergast, F. and Cormier, M., Primary structure of the *Aequorea victoria* green-fluorescent protein. *Gene*. 111: 229-33 (1992).
Ward, W., Prentice, H., Roth, A., Cody, C. and Reeves, S., 1982. Spectral perturbations of the *Aequoria* green fluorescent protein. *Photochem. Photobiol*. 35: 803-808.
Heim, R. and Tsien, R. Y.; *Current Biology*, 6(2): 178-182 (1996).
Kendall, J. M. and Badminton, M. J.; *TIBTECH*, 16: 216-224 (1998).
Labas, Y. A.; Gurskaya, N. G.; Yanushevich, Y. G.; Fradkov, A. F.; Lukyanov, K. A.; Lukyanov, S. A. and Matz, M. V.; *PNAS*, 99(7): 4256-4261 (Apr. 2, 2002).
Matz, M. V.; Fradkov, A. F.; Labas, Y. A.; Savitsky, A. P.; Zaraisky, A. G.; Markelov, M. L. and Lukyanov, S. A.; *Nature Biotechnology*, 17: 969-973 (Oct. 1999).
Murphy, J. T. and Lagarias, J. C.; *Current Biotechnology*, 7(11): 870-876 (Oct. 17, 1997)..
Schwartz, S.; Campbell, M.; Nasioulas, G.; Harrison, J.; Felber, B. K. and Pavlakis, G. N.; *J.Virol.*, 66:7176-7182 (Dec. 1992).
Wiedenmann, J.; Elke, C.; Spindler, K. and Funke, W.; *PNAS*, 97(26): 14091-14096 (Dec. 19, 2000).

* cited by examiner

*Primary Examiner*—Hope Robinson
(74) *Attorney, Agent, or Firm*—Townsend and Townsend and Crew LLP

(57) ABSTRACT

The present invention is directed to novel spontaneously fluorescent proteins having a unique chromophore formed from the amino acid sequence $FR_1R_2R_3F$ where $R_1$ is Q or S; $R_2$ is Y, W, F or H; and $R_3$ is G, A or S (SEQ ID NO:34). The invention also encompasses the expression of nucleic acids that encode the proteins of the invention in a wide variety of engineered host cells, and the isolation of engineered proteins. In other embodiments, the invention comprises methods of use, generally including tagging a molecule or cell with the proteins of the invention by either chemical means or recombinant techniques.

11 Claims, 7 Drawing Sheets

FIG. 7

```
OFP     1                                                    --------------MN-                 1
CFP484  1   MKCKFVFCLSFLVLAITNANI FLRNEADLEEKTLRI PKALTTMGVIKPDMKIKLKMEGN                        60
dsRed   1                                                    --MR-----------SSKNVIKEFMRFKVRMEGTV  22

OFP     18                   NNEFEYDGEGEGDPSTGKYSMKMTLRGQNCSPFSYDITTAFQYGFRVFTKYPEGTVDY         77
CFP484  61  NGHAVIEGEGEGKPYDGTHTLNLEVKEGAPLPFSYDILSNAFQYGNRALTKYPDDIADY                         120
dsRed   23  NGHEFEIEGEGEGRPYEGHNTVKLKVTKGGPLSPQFILSPQFMRAWDILSPQFMYGSKVYVKHPADIPDY              82

OFP     78   FKDSLRDAFQMNFRIVREDGVLNMSSDITYKDNVLHGDVWAVGVNLPPNGPVMKNEIVM                       137
CFP484  121  FKQSFREGYSMERTMTFEDKGIVKVKSDISMEEDSFIYEIRFDGMNLPPNGPVMQKKTLK                      180
dsRed   83   KKLSFPEGFKWERVMNFEDGGVVTVTQDSSLQDGCFIYKVKFIGVNFPSDGPVMQKKTMG                      142

OFP     138  ELPTETFTPKNGCVLVGFCPKAYLEKDGSYSYYGNMTTFYRSKLSGQAPPGYHFVKHRLVK                     197
CFP484  181  WEPSTEIMYVRDGVLVGDISHSLLDEGGHSVRCDFKSIYKKAYVVKLP-DYHFVDHRIEI                      239
dsRed   143  WEASTERLYPRDGVLKGEIHKALKEKDGSHLVEFKSIYMAKKPVQLP-GYYYVDSKLDI                       201

OFP     198  TNVGHGFKTVEQTEYATAHVSDLPK--                                                       222
CFP484  240  LNHDKDYNKVTLYENAVARYSLLPSQA                                                       266
dsRed   202  TSHNEDYTIVEQYERTEGRHHLFL---                                                       225
```

FLUORESCENT PROTEINS

CROSS-REFERENCES TO RELATED APPLICATIONS

This application claims the benefit of U.S. Provisional Application No. 60/370,598 filed Apr. 5, 2002 and U.S. Provisional Application No. 60/387,968 filed Jun. 11, 2002, which are incorporated herein by reference.

FIELD OF THE INVENTION

This invention relates generally to the field of reporter genes and particularly provides novel orange fluorescent proteins (OFP), nucleic acid constructs encoding OFP and methods for their use.

BACKGROUND

The discovery that Spontaneously Fluorescent Proteins (SFPs) retain their fluorescent properties when expressed in heterologous cells has provided biological research with new, unique and powerful tools (Chalfie et al, Science, 263:802 (1994); Prasher, Trends in Genetics, 11:320 (1995); WO 95/07463; Heim et al., Proc. Natl. Acad. Sci. USA, 91:12501 (1994).

The limited number of colors expressed by currently known fluorescent proteins however, limits their utility in a number of aspects. First, the number of discernable colors displayed by the fluorescent proteins limits the number of biomolecules that can be tagged with fluorescent proteins and simultaneously monitored in a cell. Second, fluorescent activated cell sorting has a preference for chromophores emitting in the red end of the spectrum. The number of spontaneously fluorescent proteins emitting in this region of the spectra is limited. Third, some applications, such as FRET, require pairs of chromophores where overlap of the emission spectra of one chromophore (the donor) with the excitation spectra of the other chromophore (the acceptor) is a necessary component of the technique. The need for overlapping spectra demands multiple chromophore variants to provide suitable donor/receptor pairs for a given application.

Creating mutations to existing spontaneously fluorescent proteins does not entirely solve the problem, as such mutations can only result in limited shifts in the spectra of the molecule. Formulation or discovery of novel chromophores for use in spontaneously fluorescent proteins would make additional regions of the spectrum available for use in fluorescent studies and advance research and diagnostic analyses using such fluorescent markers.

SUMMARY OF THE INVENTION

The present invention provides nucleic acids and proteins containing a novel chromophore capable of fluorescing in the absence of a prosthetic group. In addition to these nucleic acids and proteins, the present invention also provides methods of assay and identification of the nucleic acids and proteins, and numerous assay systems for their use.

In one embodiment, the invention comprises a nucleic acid encoding a protein having a sequence segment of between 5 and 15 amino acids within which resides the pentapeptide $FR_1R_2R_3F$ where $R_1$ is Q or S; $R_2$ is Y, W, F or H; and $R_3$ is G, A or S (SEQ ID NO:34). Preferably, the central three amino acids of the pentapeptide cyclize to form a p-hydroxybenzylidene-imidazolidinone chromophore structure. More preferably, the pentapeptide is the sequence FQYGF (SEQ ID NO:30). In a preferred aspect, the sequence segment comprising the chromophore has at least one α helical region. In another preferred aspect, the sequence segment comprising the chromophore resides in a cylindrical structure formed by the protein. More preferably, this cylindrical structure is formed for a series of β strands, most preferably eleven β strands, each β strand comprising between 7 and 15 amino acids. The nucleic acid also preferably hybridizes to one of the primer pairs selected from the group of SEQ. ID NOS: 12 and 13; and, SEQ. ID NOS: 14 and 15. Preferably, the nucleic acid has at least 55% sequence identity to the nucleotide sequence in SEQ ID NO:1. More preferably, the nucleic acid hybridizes under stringent conditions to the nucleic acid of SEQ. ID NO:1. Most preferably, the nucleic acid has the nucleotide sequence of SEQ ID NO:1.

In another embodiment, the invention provides a spontaneously fluorescent protein having a sequence segment of between 5 and 15 amino acids within which resides the pentapeptide $FR_1R_2R_3F$ where $R_1$ is Q or S; $R_2$ is Y, W, F or H; and $R_3$ is G, A or S (SEQ ID NO:34). Preferably, the central three amino acids of the pentapeptide cyclize to form a p-hydroxybenzylidene-imidazolidinone chromophore structure. More preferably, the pentapeptide is the sequence FQYGF (SEQ ID NO:30). In a preferred aspect, the sequence segment comprising the chromophore has at least one or helical region. In another preferred aspect, the sequence segment comprising the chromophore resides in a cylindrical structure formed by the protein. More preferably, this cylindrical structure is formed by a series of β strands, most preferably eleven β strands, each β strand comprising between 7 and 15 amino acids.

Preferably, spontaneously fluorescent proteins having the general structure identified above will have an amino acid sequence selected from SEQ ID NO:2, SEQ ID NO:17, SEQ ID NO:18, SEQ ID NO:19, SEQ ID NO:20, SEQ ID NO:21, SEQ ID NO:22, SEQ ID NO:27, SEQ ID NO:28, and SEQ ID NO:29.

Preferably, antibodies raised against a protein with an amino acid sequence of SEQ ID NO:2 recognize the spontaneously fluorescent protein. Most preferably, the SFP is the protein with the amino acid sequence of SEQ ID NO:2.

Still another embodiment of the invention is a heterologous molecule comprising a spontaneously fluorescent protein with a p-hydroxybenzylidene-imidazolidinone chromophore structurally linked to a biochemical composition that can be a nucleic acid, polynucleotide, amino acid, polypeptide, lipid, simple sugar, or polysaccharide. Preferably the biochemical composition is a polypeptide, most preferably the polypeptide contains at least one PEST sequence.

The invention also embodies an expression vector comprising a coding sequence, part of which is a nucleotide sequence encoding a spontaneously fluorescent protein having a β can structure. The β can structure comprises a sequence segment of between 5 and 15 amino acids where five contiguous amino acids in the sequence segment are $FR_1R_2R_3F$ where $R_1$ is Q or S; $R_2$ is Y, W, F or H; and $R_3$ is G, A or S (SEQ ID NO:34). The β can structure further comprises a plurality of eleven β strands, each β strand having a continuous amino acid sequence of between 7 and 15 amino acids. The entire structure comprises the eleven β strands forming a cylinder within which resides the sequence segment. The expression vector also contains regulatory sequences operably linked to the coding sequence. A further aspect is a kit comprising a sealed container having a measured amount of a composition comprising the expression vector and instructions for using the composition.

In addition to the coding sequences noted in the previous paragraph, one aspect of the expression vector further comprises a nucleotide sequence encoding a second polypeptide, this second nucleotide sequence being in frame with the nucleotide sequence encoding the spontaneously fluorescent protein.

Another embodiment of the invention is a recombinant cell comprising an expression vector. The expression vector comprises a coding sequence, part of which is a nucleotide sequence encoding a spontaneously fluorescent protein having a β can structure. The β can structure comprises a sequence segment of between 5 and 15 amino acids where five contiguous amino acids in the sequence segment are $FR_1R_2R_3F$ where $R_1$ is Q or S; $R_2$ is Y, W, F or H; and $R_3$ is G, A or S (SEQ ID NO:34). The β can structure further comprises a plurality of eleven β strands, each β strand having a continuous amino acid sequence of between 7 and 15 amino acids. The entire structure comprises the eleven β strands forming a cylinder within which resides the sequence segment. The expression vector also contains regulatory sequences operably linked to the coding sequence. The recombinant cell can be a bacterium, an insect cell, yeast or other fungal cell, or a mammalian cell.

Another embodiment of the invention is a recombinant cell comprising an expression vector. The expression vector comprises a coding sequence, part of which is a nucleotide sequence encoding a spontaneously fluorescent protein having a β can structure. The β can structure comprises a sequence segment of between 5 and 15 amino acids where five contiguous amino acids in the sequence segment are $FR_1R_2R_3F$ where $R_1$ is Q or S; $R_2$ is Y, W, F or H; and $R_3$ is G, A or S (SEQ ID NO:34). The β can structure further comprises a plurality of eleven β strands, each β strand having a continuous amino acid sequence of between 7 and 15 amino acids. The entire structure comprises the eleven β strands forming a cylinder within which resides the sequence segment. Functionally linked to the first nucleic acid is a second nucleotide sequence encoding a second polypeptide, this second nucleotide sequence being in frame with the nucleotide sequence encoding the spontaneously fluorescent protein. The expression vector also contains regulatory sequences operably linked to the coding sequence.

Several methods are also embodied within the invention, including a method of manufacturing a spontaneously fluorescent protein. The spontaneously fluorescent protein has a p-hydroxybenzylidene-imidazolidinone chromophore. The method for making the SFP comprises obtaining a nucleic acid encoding the spontaneously fluorescent protein; operably linking the nucleic acid to an expression cassette; incorporating the expression cassette into a host cell; permitting the host to express the spontaneously fluorescent protein; and isolating the spontaneously fluorescent protein from the host cell.

Another method embodied in the invention is a method of studying cellular dynamics, the method comprising: obtaining a nucleic acid encoding a spontaneously fluorescent protein comprising a p-hydroxybenzylidene-imidazolidinone chromophore; creating a fusion gene by linking the nucleic acid encoding the spontaneously fluorescent protein to a coding sequence for a protein to be labeled; operably linking the fusion gene to an expression cassette; incorporating the expression cassette into a cell; and observing the cell with a fluorescent microscope.

A further method embodied in the invention is a method of labeling a biochemical composition, the method comprising: obtaining a spontaneously fluorescent protein comprising a p-hydroxybenzylidene-imidazolidinone chromophore of the invention (e.g., FIG. 1) producing a labeled biochemical by structurally linking the biochemical composition to the spontaneously fluorescent protein; and, isolating the labeled biochemical composition.

Antibodies specifically recognizing the spontaneously fluorescent proteins of the invention are also embodied in the invention. One such embodiment is an antibody or antigen-binding fragment thereof, that specifically binds to the spontaneously fluorescent protein having the amino acid sequence in SEQ ID NO:2. This antibody could be either polyclonal or monoclonal. Other aspects of the invention are antibodies generated against a polypeptide found in SEQ ID NO:2.

BRIEF DESCRIPTION OF FIGURES

FIG. 7 is a multiple sequence alignment including the orange fluorescent protein of SEQ ID NO:1, the green fluorescent protein cFP484 (SEQ ID NO:31), and the spontaneously fluorescent protein DsRed (SEQ ID NO:32). The sequences are aligned on the FQYG (SEQ ID NO:33) sequence common to the chromophores of all three fluorescent proteins.

DEFINITIONS

Figure 1:
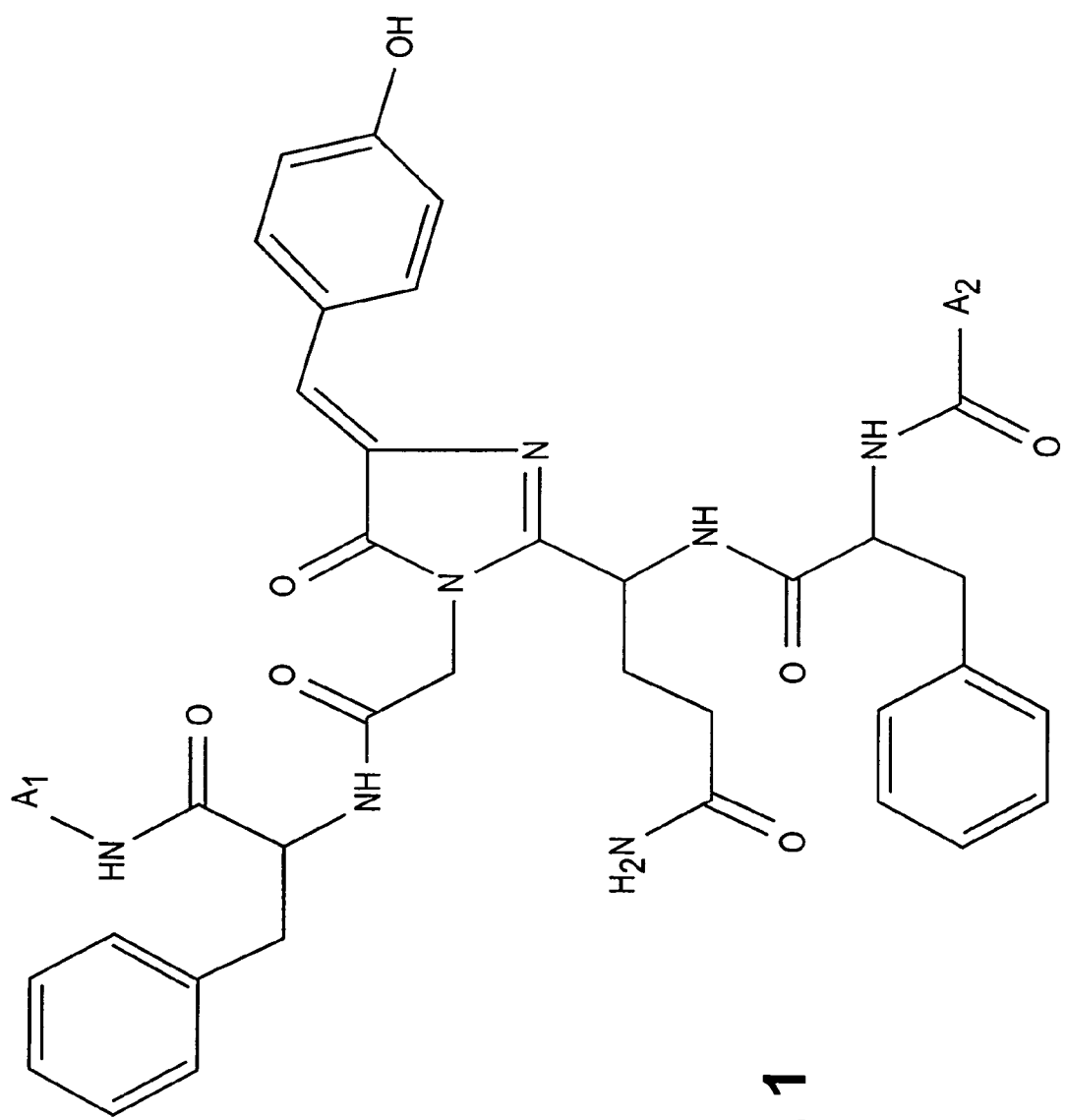
FIG. 1 illustrates the chemical structure of the orange fluorescent protein chromophore of Cnidaria "tube anemone" Cerianthus sp., formed from the amino acid pentamer FQYGF (SEQ ID NO:30). The central three amino acids of this pentamer cyclize to form the p-hydroxybenzylidene-imidazolidinone structure characteristic of all spontaneously fluorescent proteins. A1 and A2 are respectively different polypeptides linked to the chromophore through amino (amide) bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and o-phosphoserine. "Amino acid analog" refers to compounds that have the same basic chemical structure as a naturally occurring amino acid, i.e., a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The term "amino acid sequence" refers to the positional relationship of amino acid residues as they exist in a given polypeptide or protein.

In the context of both amino acid and nucleic acid sequences of the present invention, the terms include "Conservatively modified variants", whether representing the entire functional sequence or a fragment thereof. With respect to particular nucleic acid sequences, conservatively modified variants refers to those nucleic acids which encode identical or essentially identical amino acid sequences, or where the nucleic acid does not encode an amino acid sequence, to essentially identical sequences. The term also refers to fragments of particular sequences, where the sequence of the fragment has been conservatively modified as described herein. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein that encodes a polypeptide also describes every possible silent variation of the nucleic acid. One of skill will recognize that each codon in a nucleic acid (except AUG, which is ordinarily the only codon for methionine, and UGG, which is ordinarily the only codon for tryptophan) can be modified to yield a functionally identical molecule. Accordingly, each silent variation of a nucleic acid that encodes a polypeptide is implicit in each described sequence.

As to amino acid sequences, one of skill will recognize that individual substitutions, deletions or additions to a polynucleotide, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well-known in the art. Such conservatively modified variants are in addition to and do not exclude polymorphic variants, interspecies homologues, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins*, $2^{nd}$ ed., W.H. Freeman (1993)).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. For sequence comparison of OFPs, homologues of OFPs, or nucleic acid sequences encoding the same, the BLAST and BLAST 2.0 algorithms and the default parameters discussed below are used.

A "comparison window", as used herein, includes reference to a segment of any one of the number of contiguous positions selected from the group consisting of from 4 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith and Waterman, *Adv. Appl. Math.,* 2:482 (1981), by the homology alignment algorithm of Needleman and Wunsch, *J. Mol. Biol.,* 48:443 (1970), by the search for similarity method of Pearson and Lipman, *Proc. Natl. Acad. Sci. USA,* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

A preferred example of an algorithm that is suitable for determining percent sequence identity and sequence similarity are the BLAST and BLAST 2.0 algorithms, which are described in Altschul et al., *Nuc. Acids Res.,* 25:3389-3402 (1977) and Altschul et al., *J. Mol. Biol.,* 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues;

always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, M=5, N=−4 and a comparison of both strands. For amino acid sequences, the BLASTP program uses as defaults a word length (W) of 3, and expectation (E) of 10, and the BLOSUM62 scoring matrix (see Henikoff and Henikoff, *Proc. Natl. Acad. Sci. USA,* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin and Altschul, *Proc. Natl. Acad. Sci. USA,* 90:5873-5787 (1993)). One measure of similarity provided by the BLAST algorithm is the smallest sum probability (P(N)). P(N) provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An alternative to the BLAST program is the GCG (Genetics Computer Group, Program Manual for the GCG Package, Version 7, Madison, Wis.) PILEUP program. PILEUP creates a multiple sequence alignment from a group of related sequences using progressive, pair wise alignments to show relationship and percent sequence identity. It also plots a tree or dendrogram showing the clustering relationships used to create the alignment. PILEUP uses a simplification of the progressive alignment method of Feng and Doolittle, *J. Mol. Evol.,* 35:351-360 (1987). The method used is similar to the method described by Higgins and Sharp, *CABIOS,* 5:151-153 (1989). The program can align up to 300 sequences, each of a maximum length of 5,000 nucleotides or amino acids. The multiple alignment procedure begins with the pair wise alignment of the two most similar sequences, producing a cluster of two aligned sequences. This cluster is then aligned to the next most related sequence or cluster of aligned sequences. Two clusters of sequences are aligned by a simple extension of the pair wise alignment of two individual sequences. The final alignment is achieved by a series of progressive, pair wise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

When the polypeptide encoded by the first nucleic acid is immunologically cross reactive with the antibodies raised against the polypeptide encoded by the second nucleic acid, this is an indication that two nucleic acid sequences or polypeptides are substantially identical, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "antibody" refers to a polypeptide comprising a framework region from an immunoglobulin gene or fragments thereof that specifically binds and recognizes an antigen. The recognized immunoglobulin genes include the κ, λ, α, γ, δ, ε, and μ constant region genes, as well as the myriad immunoglobulin variable region genes. Light chains are classified as either κ or λ. Heavy chains are classified as γ, λ, α, δ, or ε, which in turn define the immunoglobulin classes, IgG, IgM, IgA, IgD and IgE, respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H1$ by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3$^{rd}$ ed. 1993)). While various antibody fragments, or antigen-binding fragments, are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature,* 348:552-554 (1990)).

For preparation of monoclonal or polyclonal antibodies, any technique known in the art can be used (see, e.g., Kohler and Milstein, *Nature,* 256:495-497 (1975); Kozbor et al., *Immunology Today,* 4:72 (1983); Cole et al., pp.77-96 in *Monoclonal Antibodies and Cancer Therapy*, Alan R. Liss, Inc. (1985); (U.S. Pat. No. 4,946,778)).

The term "biochemical composition" refers to any molecular component found in a cell, including fusion molecules, precipitates, salts, chelates and other structurally-linked molecular entities of the same.

"α helix" refers to a peptide conformation comprising at least 4 contiguous amino acid residues, where the peptide backbone is coiled such that the structure repeats itself approximately every 5.4 Å along a helical axis. This helical repetition completes a turn after approximately 3.6 amino acid residues, with the separation between amino acid residues along the helical axis generally being about 1.5 Å. The peptide planes are roughly parallel with the helix axis and the dipoles within the helix aligned (all C═O groups point in roughly the same direction and all N—H groups point in the opposite direction). This structure results in every main chain C═O and N—H group potentially hydrogen-bonding to a peptide bond 4 residues away (i.e., $O_{(i)}$ to $N_{(i+4)}$), producing a regular, stable arrangement. Side chains point outward from helical axis and are generally oriented towards its amino-terminal end. All the amino acids have negative phi and psi angles, with phi values ranging from −20 to −170 degrees and psi values of between −15 and −80. Typical phi and psi values are −60 degrees and −50 degrees respectively.

The α helical structure is able to absorb considerable variation from ideal structural parameters. Variation is introduced into the structure through side chain interactions with both each other and surrounding solvent molecules. The term "α helix enhancing" amino acid or like term is meant an amino acid which has a recognized tendency to form or stabilize an alpha-helix as measured by assays well-known in the field. See generally O'Neil, K. T. and DeGrado, W. F., *Science*, 250:646 (1990) and references cited therein for such an assay. Preferred α helix enhancing amino acids are listed in Table 1 and discussed in detail below. A particularly preferred α helix enhancing amino acid is alanine. By the term "substantial α helicity" is meant that a particular peptide has a recognizable α-helical structure as determined, e.g., by a helical wheel diagram or other conventional means.

The term "β strand" refers to a peptide conformation where the peptidyl backbone zigzags in a more or less extended conformation, with axial distances between adjacent amino acids of approximately 3.5 Å. Portions of polypeptide chains that run "parallel" all run in the same direction. Polypeptide chains that are "antiparallel" run in the opposite direction from the parallel chains. Amino acid residues of a peptide in a β conformation have negative phi angles and the psi angles are positive. Within a β-sheet structure, phi angles generally range from −30 to −170 degrees, with psi values ranging from 90 to 180 degrees. Typical values are phi=−140 degrees and psi=130 degrees. A section of polypeptide with 3 or more residues in the β conformation is referred to as a "β strand", with individual β strand being capable of associating by main chain hydrogen bonding interactions to form a "β sheet".

The β sheet is stabilized by hydrogen bonds between NH and CO groups in different polypeptide strands. Additionally, the dipoles of the peptide bonds alternate along the strands, imparting intrinsic stability to the β sheet. The adjacent strands in the β sheet can run in the same direction (i.e., a parallel β sheet) or in opposite directions (i.e., an antiparallel β sheet). Although the two forms differ slightly in dihedral angles, both are sterically favorable. The extended conformation of the β sheet conformation results in the amino acid side chains protruding on alternating faces of the β sheet.

Numerous articles and programs are available for calculating phi and psi bond angles, and determining molecular structure through comparison of primary sequence, including PROCHECK: Laskowski et al., *J. App. Cryst.*, 26:283 (1993). VERIFY3D: Assessment of protein models with three-dimensional profiles by Eisenberg et al., *Meth. Enz.*, 277:366-404 (1997). Assessment of protein models with three-dimensional profiles by Luethy et al., *Nature*, 256:83-85 (1992). WHAT IF: A molecular modeling and drug design program by Vriend, G., *J. Mol. Graph.*, 8:52-56 (1990). *Errors in protein structures*, Hooft et al., *Nature*, 381:272-272 (1996).

A classical method, with a predictive success rate of 50% or better, was suggested by Chou and Fasman. In this method, the frequency of occurrences for each amino acid in α helices and β sheets of proteins with known structure are first determined. Frequencies are assigned for both the ability to initiate and terminate various secondary structures, and the residues classified as strong formers, weak formers, formers, indifferent formers, strong breakers and breakers. Exemplary amino acids for each category are as follows;

TABLE 1

| Strength | α Helix | β Strand |
|---|---|---|
| Strong former | glu, ala, leu | met, val, ile |
| Former | his, met, gln, trp, val, phe | cys, tyr, phe, gln, leu, thr, trp |
| Weak former | lys, ile | ala |
| Indifferent former | asp, thr, ser, arg, cys | arg, gly, asp |
| Breaker | asn, tyr | lys, ser, his, asn, pro |
| Strong breaker | pro, gly | glu |

Briefly, the Chou and Fasman method entails assigning residues to one of the categories above, for both α helix and β strand. Working through the primary sequence six residues at a time, the method searches for a nucleus of four residues out of the six that are either helix formers or strong helix formers. When a helix-forming nucleus is found, the method extends the helix region from the nucleus in both directions until terminated by a tetrapeptide with an average α helix propensity of the region equal to 1.0 (indifferent). At all times prolines are not allowed in the helical region.

The next stage of the method attempts to locate β strand regions in a similar manner to that described above for α helices. In the case of β strands, the comparison sequence is five residues, and the method searches for three of the five that are formers or strong formers, identifying a β strand nucleus. When a strand-forming nucleus is found, the method extends the β strand region from the nucleus in both directions until terminated by a tripeptide with an average β strand propensity of the region is equal 1.0 (indifferent). At all times prolines are not allowed in the β strand region.

"β can" or "β can structure" refers to a protein conformation first described by Yang, et al., *Nature Biotech.*, 14:1246-1251 (1996). The structure is characterized as a plurality of 9 to 14 antiparallel β strands, preferably 11 β strands, forming a compact cylindrical β sheet structure. In the context of this invention, an amino acid sequence segment comprising a fluorescent chromophore is located inside the β sheet cylinder. There may also be short helical segments on either or both ends of the cylinder. The cylinder of a typical 11-stranded β can has an approximate diameter of about 30 Å and a length of about 40 Å, as determined by X-ray crystallographic analysis.

The term "biochemical composition" refers to those compounds, both simple and complex in structure, that go to form cellular components, or are products or intermediates in biochemical pathways occurring in the course of cellular metabolism. The term also encompasses synthetic agonists, antagonists and other modulators of cellular function. The definition holds, regardless of whether the biochemical composition is used in conjunction with living cells or tissues, in vitro or in vivo, or in purely synthetic applications.

The term "cellular dynamics" refers to all chemical processes, movement, and transport occurring, or having had occurred, with a cell or tissue, regardless of whether the process is catabolic or anabolic in nature.

In the context of this invention, the term "chromophore" refers to a chemical group capable of selective light absorption and emission, potentially resulting in the coloration of a spontaneously fluorescent protein. The chromophore of the present invention is formed from a cyclization reaction of three amino acids to form an imidazolidinone ring. The spectroscopic characteristics of the chromophore are a product of the interaction of the imidazolidinone ring and neighboring amino acids as they are found in the tertiary structure of the protein comprising the chromophore. The emission of light by the chromophore results from the presence in the chromophore of a coordinate bond structure comprised of electrons capable of being excited from a ground state to an excited state. Light emission occurs when the excited electrons return to their ground state by releasing energy in the form of selective wavelengths of light energy.

The term "coding sequence", in relation to nucleic acid sequences, refers to a plurality of contiguous sets of three nucleotides, termed codons, each codon corresponding to an amino acid as translated by biochemical factors according to the universal genetic code, the entire sequence coding for an expressed protein, or an antisense strand that inhibits expression of a protein. A "genetic coding sequence" is a coding sequence where the contiguous codons are intermittently interrupted by non-coding intervening sequences, or "introns." During mRNA processing intron sequences are removed, restoring the contiguous codon sequence encoding the protein or anti-sense strand.

The term "contiguous" in the context of polynucleotide or polypeptide sequences, refers to an uninterrupted sequence of bases or amino acids, each base or amino acid being immediately adjacent to its neighbors in the sequence.

The term "cylinder", in the context of this invention, refers to a molecular protein structure resulting from the interaction of at least 6 β strands, each β strand being at least 5 amino acids in length, to form an enclosed anti-parallel β sheet conformation that is roughly circular in cross-section when viewed down the axis of the β sheet.

The terms "expression vector" and "expression cassette" include any type of genetic construct containing a nucleic acid capable of being transcribed in a cell. The expression vectors of the invention generally supply sequence elements directing translation of the coding sequence into an OFP, as provided by the invention itself, although vectors used for the amplification of nucleotide sequences (both coding and non-coding) are also encompassed by the definition. In addition to the coding sequence, expression vectors will generally include restriction enzyme cleavage sites and the other initial, terminal and intermediate DNA sequences that are usually employed in vectors to facilitate their construction and use. The expression vector can be part of a plasmid, virus, or nucleic acid fragment.

The term "fusion gene" refers to the combination of one or more heterologous coding sequences joined in frame to form a single translational/transcriptional unit. Typically the heterologous coding sequences are joined end-to-end. The definition however includes fusion genes where one sequence, or fragment thereof, intervenes in another heterologous sequence.

The term "functionally compatible environment" refers to both a micro- and a macro-environment for an OFP chromophore that allows the chromophore to exhibit at least a trace of fluorescent capacity. Structurally this entails a stable protein conformation capable of maintaining the chromophore in a favorable orientation, the half-life of the conformation being greater than the half-life of the excited electrons involved in producing a fluorescence of the chromophore.

The term "fusion molecule", in the context of the present invention, refers to any molecule formed through the structural linkage of an SFP and another molecule from any source including natural, recombinant, semi-synthetic and synthetic.

The term "heterologous" when used with reference to portions of a nucleic acid or protein indicates that the molecule comprises two or more subsequences that are not found in the same relationship to each other in nature. For instance, a heterologous nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The term "host cell" refers to a cell that contains an expression vector and supports the replication and/or expression of genes encoded by the expression vector. Host cells may be prokaryotic cells such as $E.\ coli$, or eukaryotic cells such as yeast, insect, amphibian, or mammalian cells such as Ba/F3, COLO205 and the like, e.g., cultured cells, explants, and cells in vivo.

The term "isolated" refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other components normally present in a solution of the same. The terms "isolated" and "purified" do not encompass nucleic acids or polypeptides present in their natural source.

The term "lipid" refers to any of a group of organic compounds, including the fats, oils, waxes, sterols, and triglycerides that are generally insoluble in water but soluble in non-polar organic solvents, are oily to the touch, and together with carbohydrates and proteins constitute the principal structural material of living cells. "Lipid" also refers to bipolar molecules, having one region that is hydrophobic and another that is hydrophilic. Such bipolar molecules readily form micelles or bilayer structures.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-o-methyl ribonucleotides and peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.*, 19:5081 (1991); Ohtsuka et al., *J. Biol. Chem.*, 260:2605-2608 (1985); Rossolini et al., *Mol. Cell. Probes*, 8:91-98 (1994)). The term "nucleic acid" is used interchangeably with the terms "gene", "cDNA", "mRNA","oligonucleotide", and "polynucleotide" when referring to multiple covalently-linked strings of purine and/or pyrimidine bases.

Orange fluorescent protein (OFP) refers to a class of proteins comprising a functional chromophore formed from the amino acid pentapeptide $FR_1R_2R_3F$ where $R_1$ is Q or S; $R_2$ is Y, W, F or H; and $R_3$ is G, A or S (SEQ ID NO:34). The central three amino acids of the pentamer sequence form the p-hydroxybenzylidene-imidazolidinone ring structure characteristic of all spontaneously fluorescent proteins. The term "OFP" therefore refers to polymorphic variants, alleles, mutants, and interspecies homologues of the OFP that: (1) have an amino acid subsequence that has greater than about 60% amino acid sequence identity, 65%, 70%, 75%, 80%, 85%, 90%, preferably 95%, 96%, 97%, 98% or 99% or greater amino acid sequence identity, to an OFP sequence of SEQ ID NO:2; (2) binds to antibodies, e.g., polyclonal antibodies, raised against an immunogen comprising an amino acid sequence of SEQ ID NO:2, a fragment from SEQ ID NO:2, or conservatively modified variants thereof; (3) specifically hybridize under stringent hybridization conditions to a sequence of SEQ ID NO: 1, a fragment of SEQ ID NO:1, and conservatively modified variants thereof; (4) has a nucleic acid subsequence that has greater than about 90%, preferably greater than about 96%, 97%, 98%, 99%, or higher nucleotide sequence identity to SEQ ID NO:1; (5) is amplified by primers that specifically hybridize under stringent hybridization conditions to the same sequence as a primer set selected from the group consisting of SEQ ID NOS: 12 and 13 or 14 and 15; or (6) possess an OFP chromophore in a functionally compatible environment.

"p-hydroxybenzylidene-imidazolidinone" refers to the core ring structure of the chromophore found in the present invention, and is depicted in FIG. 1. The structure is formed from three contiguous amino acids, with the center amino acid having an aromatic side chain. The ring is formed in a condensation reaction that comprises a nucleophilic attack by the amino nitrogen of the third amino acid, on the carbonyl carbon of the first amino acid. The $C^\alpha$—$C^\beta$ bond in the aromatic side chain of the central tyrosyl residue is also oxidized, forming a large delocalized π-electron system.

The term "PEST sequence" refers to a sequence segment of a protein that is rich in proline, glutamic acid, serine and threonine (P, E, S and T) and generally flanked by clusters of positively charged amino acids (Rogers, et al., *Science* 234:364-68 (1986); Rechsteiner, M., *Seminars in Cell Biology*, 1:433-40 (1990)). Proteins comprising such sequences typically have intracellular half-lives of less than two hours (See e.g., U.S. Pat. No. 6,306,600).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

Macromolecular structures such as polypeptide structures can be described in terms of various levels of organization. For a general discussion of this organization, see, e.g., Alberts et al., *Molecular Biology of the Cell* (3$^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three-dimensional structures within a polypeptide. These structures are commonly known as domains. Domains are portions of a polypeptide that form a compact unit of the polypeptide and are typically 5 to 350 amino acids long. Typical domains are made up of organized sections of peptide such as stretches of β strands (that can interact to form β sheets) and α helices. "Tertiary structure" refers to the complete three-dimensional structure of a polypeptide monomer. "Quaternary structure" refers to the three dimensional structure formed by the non-covalent association of independent tertiary units. Anisotropic terms are also known as energy terms.

The term "scaffold" or "protein scaffold" refers to the tertiary structure of the protein. More particularly, in the context of this invention, the term "scaffold" refers to those aspects of the tertiary structure of a fluorescent protein involved in creating a functionally compatible environment for the chromophore. This entails maintaining the chromophore in a molecular orientation compatible with fluorescence and protecting the chromophore from outside influence as necessary to allow the chromophore to maintain any degree of functionality.

The term "polysaccharide" refers to any of a class of carbohydrates, such as starch and cellulose, consisting of a number of monosaccharides joined by glycosidic bonds.

The terms "primers" or "primer pairs" refer to oligonucleotide probes capable of recognizing and hybridizing to specific nucleotide sequences found in a target gene or sequence to be amplified by polymerase chain reaction (PCR). The degree of complementarity required between the primers and the target sequence determines the specificity, or stringency of conditions required for hybridization of the sequences. A temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications*, Academic Press, Inc. N.Y. (1990)).

The term "Regulatory sequences" refers to those sequences, both 5' and 3' to a structural gene, that are required for the transcription and translation of the structural gene in the target host organism. Regulatory sequences include a promoter, ribosome binding site, optional inducible elements and sequence elements required for efficient 3' processing, including polyadenylation. When the structural gene has been isolated from genomic DNA, regulatory sequences also include those intronic sequences required to remove of the introns as part of mRNA formation in the target host.

The term "recombinant" when used with reference, e.g., to a cell, or nucleic acid, protein, or vector, indicates that the cell, nucleic acid, protein or vector, has been modified by the introduction of a heterologous nucleic acid or protein, or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under-expressed or not expressed at all.

DNA regions are "operably linked" when they are functionally related to each other. For example, DNA for a signal peptide (secretory leader) is operably linked to DNA for a polypeptide if it is expressed as a precursor which participates in the secretion of the polypeptide; a promoter is operably linked to a coding sequence if it controls the transcription of the sequence; or a ribosome-binding site is operably linked to a coding sequence if it is positioned so as to permit translation. Generally, operably linked means contiguous and in reading frame.

The phrase "selectively (or specifically) hybridizing" refers to the binding, duplexing, or hybridizing between two particular nucleotide sequences under stringent hybridization conditions when the sequences are present in a complex mixture (e.g., total cellular or library DNA or RNA).

The term "binding specifically (or selectively)" is also used to describe specific antigen-antibody interactions, and, in the context of this invention, is synonymous with "specifically (or selectively) immunoreactive with." The terms refer to specified antibodies binding to a particular protein or homologues of a particular protein, typically with the reaction signal being at least twice the background signal and more typically more than 10 to 100 times background, without significant binding to other peptides or proteins present in the sample.

Specific binding to an antibody under such conditions may require an antibody that is selected for its specificity for a particular protein. For example, polyclonal antibodies raised to the OFP sequence as presented in SEQ ID NO:2, variants, or portions thereof, can be selectively screened to yield only those polyclonal antibodies that are specifically immunoreactive with the protein of SEQ ID NO:2 and not with other proteins. This selection may be achieved by subtracting out antibodies that cross-react with other molecules. In addition, polyclonal antibodies raised to OFP homologues, orthologs, and conservatively modified variants can be selectively screened to yield only those antibodies that recognize members of the OFP family. A variety of immunoassay formats may be used to select antibodies specifically immunoreactive with a particular protein. For example, solid-phase ELISAs s are routinely utilized for this purpose (see, e.g., Harlow and Lane, *Antibodies, A Laboratory Manual* (1988) for a description of immunoassay formats and conditions that can be used to determine specific immunoreactivity).

The terms "sequence similarity", "sequence identity", or "percent identity" in the context of two or more nucleic acids or polypeptide sequences, refer to two or more sequences or subsequences that are, when optimally aligned with appropriate nucleotide insertions or deletions, the same or have a specified percentage of amino acid residues or nucleotides that are the same (i.e., 50% identity, 65%, 70%, 75%, 80%, preferably 85%, 90%, 91%, 92%, 93%, 94%, 95%, 96%, 97%, 98%, 99% or higher identity to an acid sequence such as SEQ ID NO:2, or a nucleotide sequence such as SEQ ID NO:1), when compared and aligned for maximum correspondence over a comparison window, or designated region as measured using one of the following sequence comparison algorithms or by manual alignment and visual inspection. This definition also refers to the compliment of a test sequence. Preferably, the identity exists over a region that is at least about 25 amino acids or nucleotides in length, or more preferably over a region that is 50-100 amino acids or nucleotides in length. These relationships hold, notwithstanding evolutionary origin (Reeck et al., *Cell,* 50:667 (1987)). When the sequence identity of a pair of polynucleotides or polypeptides is greater or equal to 65%, the sequences are said to be "substantially identical."

Alternatively, substantial identity will exist when a nucleic acid will hybridize under selective hybridization conditions, to a strand or its complement. Typically, selective hybridization will occur when there is at least about 55% homology over a stretch of at least about 14 nucleotides, more typically at least about 65%, preferably at least about 75%, and more preferably at least about 90%. See, Kanehisa, *Nuc. Acids Res.,* 12:203-213 (1984), which is incorporated herein by reference. The length of homology comparison, as described, may be over longer stretches, and in certain embodiments will be over a stretch of at least about 17 nucleotides, generally at least about 20 nucleotides, ordinarily at least about 24 nucleotides, usually at least about 28 nucleotides, typically at least about 32 nucleotides, more typically at least about 40 nucleotides, preferably at least about 50 nucleotides, and more preferably at least about 75 to 100 or more nucleotides.

Amino acid sequence homology, or sequence identity, is determined by optimizing residue matches, if necessary, by introducing gaps as required. This change when considering conservative substitutions as matches. Conservative substitutions typically include substitutions within the following groups: [glycine, alanine]; [valine, isoleucine, leucine]; [aspartic acid, glutamic acid]; [asparagine, glutamine]; [serine, threonine]; [lysine, arginine]; and [phenylalanine, tyrosine]. Homologous amino acid sequences are intended to include natural allelic and interspecies variations in each respective receptor sequence. Typical homologous proteins or peptides will have from 25-100% homology (if gaps can be introduced), to 50-100% homology (if conservative substitutions are included). Homology measures will be at least about 50%, generally at least 56%, more generally at least 62%, often at least 67%, more often at least 72%, typically at least 77%, more typically at least 82%, usually at least 86%, more usually at least 90%, preferably at least 93%, and more preferably at least 96%, and in particularly preferred embodiments, at least 98% or more.

In relation to proteins, the term "sequence homology" in all its grammatical forms refers to the relationship between proteins that possess a "common evolutionary origin" including proteins from superfamilies (e.g., the immunoglobulin superfamily) and homologous proteins from different species (e.g., myosin light chain, etc.) (Reeck et al., *Cell,* 50:667 (1987)). The present invention naturally contemplates homologues of the OFP as falling within the scope of the invention.

The term "sequence segment" refers to a contiguous string of amino or nucleic acids, regardless of sequence.

The terms "simple sugar" and "monosaccharide" refers to any of several carbohydrates, such as tetroses, pentoses, and hexoses that cannot be broken down to simpler sugars by hydrolysis.

The term "spontaneously fluorescent protein" (SFP) refers to a class of proteins comprising a fluorescent chromophore, the chromophore being formed from at least 3 amino acids and characterized by a cyclization reaction creating a p-hydroxybenzylidene-imidazolidinone chromophore. The chromophore does not contain a prosthetic group and is capable of emitting light of selective energy, the energy having been stored in the chromophore by previous illumination from an outside light source comprising the correct wavelength(s). Spontaneously fluorescent proteins can be of any structure, with a chromophore comprising any number of amino acids, provided that the chromophore comprises the p-hydroxybenzylidene-imidazolidinone ring structure, as detailed above. SFP's typically, but not exclusively, comprise a β-barrel structure such as that found in green fluorescent proteins and described in Chalfie et al., *Science,* 263, 802-805 (1994).

The phrase "stringent conditions" or "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength and pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous references, e.g., Wetmur and Davidson, *J. Mol. Biol.*, 31:349-370 (1968) and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C. to 95° C. for 30 sec to 2 min., an annealing phase lasting 30 sec. to 2 min., and an extension phase of about 72° C. for 1 to 2 min. Protocols and guidelines for low and high stringency amplification reactions are provided, e.g., in Innis et al. (1990) *PCR Protocols, A Guide to Methods and Applications*, Academic Press, Inc. N.Y.).

The term "structurally-linked" refers to a specific interaction between two molecules that is stable under physiologic conditions. A "structural link" can take the form of any type of bond, including but not limited to covalent, hydrophobic, ionic and electrostatic. When two or more components are structurally-linked in a manner that does not interfere with the function of one or more of the linked components, then the components are said to be "functionally-linked."

DETAILED DESCRIPTION

I. Introduction

The present invention provides, for the first time, fluorescent proteins and the nucleic acids encoding them, where the fluorescent proteins have a novel chromophore. The chromophore is preferably formed from a pentameric amino acid sequence having the structure $FR_1R_2R_3F$, where $R_1$ is Q or S; $R_2$ is Y, W, F or H; and $R_3$ is G, A or S. Ideally, the pentameric amino acid sequence is FQYGF (SEQ ID NO:30). We have coined the term "orange fluorescent proteins" (OFP) for this new class of proteins, as the original isolate displayed a brilliant orange fluorescence after excitation with light of wavelength 548 nm. It must be noted however that the actual color displayed by a given OFP is highly dependent upon the environment provided to the OFP chromophore and the particular OFP chromophore variant present in the protein. As different members of the OFP class of proteins are contemplated to have diverse structural characteristics leading to color shifts away from the orange fluorescence of the original isolate, the term "orange fluorescent protein" should in no way be construed as limiting upon the present invention.

OFPs can be found in a diverse set of organisms, including species of sea anemones, corals, tubeworms, jellyfish, and sea pansies. The original isolate was purified from the *Cnidaria* "tube anemone" *Cerianthus* sp., purchased from a distributor of ornamental aquatic life and widely distributed throughout the Indo-Pacific Ocean region, particularly found in association with coral beds.

The invention also provides methods for identifying and isolating OFPs, and the nucleic acids encoding them. Nucleic acids encoding OFP can be isolated from cDNA or genomic libraries constructed from sea anemones, corals, tubeworms, jellyfish, sea pansies and other sources using PCR and molecular biological techniques described herein. The invention provides an exemplary OFP nucleic acid sequence, allowing one of ordinary skill in the art to synthetically construct a nucleic acid encoding an OFP.

Methods for identifying nucleic acids of the invention are also described. These include Southern blotting, Northern blotting, PCR and sequence analysis techniques, among others.

Several techniques for expressing OFP in a diverse set of cell types are included in the invention. Cell types suitable for expression of OFP include, but are not limited to, bacteria, yeast, insect, filamentous fungi, plant and mammalian cells. Expression constructs suitable for expression of OFP in each cell type are also disclosed, including exemplary regulatory sequences for controlling expression.

The present invention includes numerous methods for isolating expressed OFP, both from a native source and from recombinant sources. These methods include conventional chromatography techniques, "tagging" protocols such as incorporation of a string of histidines into a protein structure allowing the protein to be purified by chelation columns that specifically recognize the added histidine residues. Epitope tagging, particularly FLAG™ tagging, is described in detail, as are other immunochemical techniques for isolating and identifying OFP proteins.

Identification of OFP, whether the protein is intracellular, extracellular or purified, can be performed using immunological techniques, protein analysis such as N-terminal sequencing, spectro- and fluoroscopic analysis, chromatographic analysis techniques such as polyacrylamide gel electrophoresis, a combination of immunological and chromatographic analysis, i.e., Western blotting, or any other analytical procedure well-known in the art for detecting proteins.

Functionally, OFPs are fluorescent proteins that do not require a prosthetic group to display their characteristic spectroscopic properties. OFPs are readily amenable to forming fusion proteins, whether chemically or recombinantly generated. Fusion proteins of the invention include fusions of OFP with lipids, nucleic acids, carbohydrates, as well as proteins. Fusion of any of these molecules generally has little effect on either OFP or it's fusion partner owing to the extremely stable and generally compact core structure of OFP, as discussed below.

Structurally, OFPs are believed to be tetrameric complexes, with each monomer having a core structure that and is quite small, around 25 kDa or less, that is required for functional fluorescence. The OFPs of the present invention are preferably between about 20 kDa and about 100 kDa, more preferably between 25 kDa and 50 kDa. The structural characteristic shared by all OFPs is a fluorescent chromophore formed from the pentapeptide $FR_1R_2R_3F$ where $R_1$ is Q or S; $R_2$ is Y, W, F or H; and $R_3$ is G, A or S (SEQ ID NO:34), with the central three peptides cyclizing to form a p-hydroxybenzylidene-imidazolidinone ring structure. In the exemplary OFP isolated from *Cerianthus* sp., this chromophore is located in a peptide segment that resides within a cylindrical structure referred to as a "β can". The β can is formed from eleven β strands that in essence form a tubular β sheet. This β can scaffold support for the chromophore is the preferred OFP tertiary conformation. However, the critical aspect of the β can structure is that it holds the chromophore in the correct orientation and environment to fluoresce, thus alternative structures capable of orientating and maintaining the chromophore correctly to allow for fluorescence are also encompassed in the invention. Such structures must generally be extremely stable to maintain the chromophore in a functional orientation.

Figure 4:
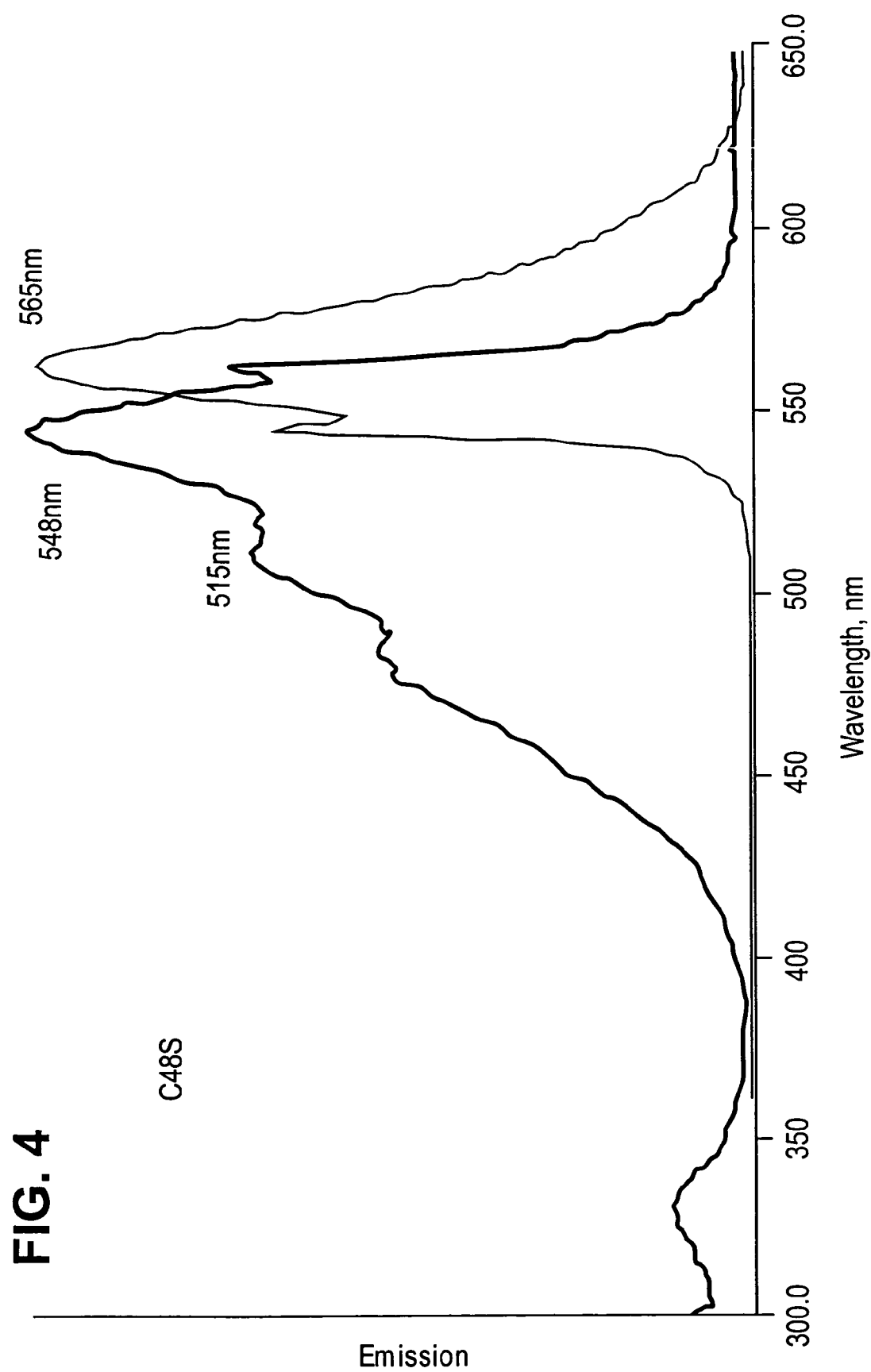
FIG. 4 is a spectrograph of the excitation and emission spectra for the orange fluorescent protein generated by the $Cys^{48}Ser$ point mutation to the OFP encoded by SEQ ID NO:1, and having the primary sequence of SEQ ID NO:27.
Figure 5:
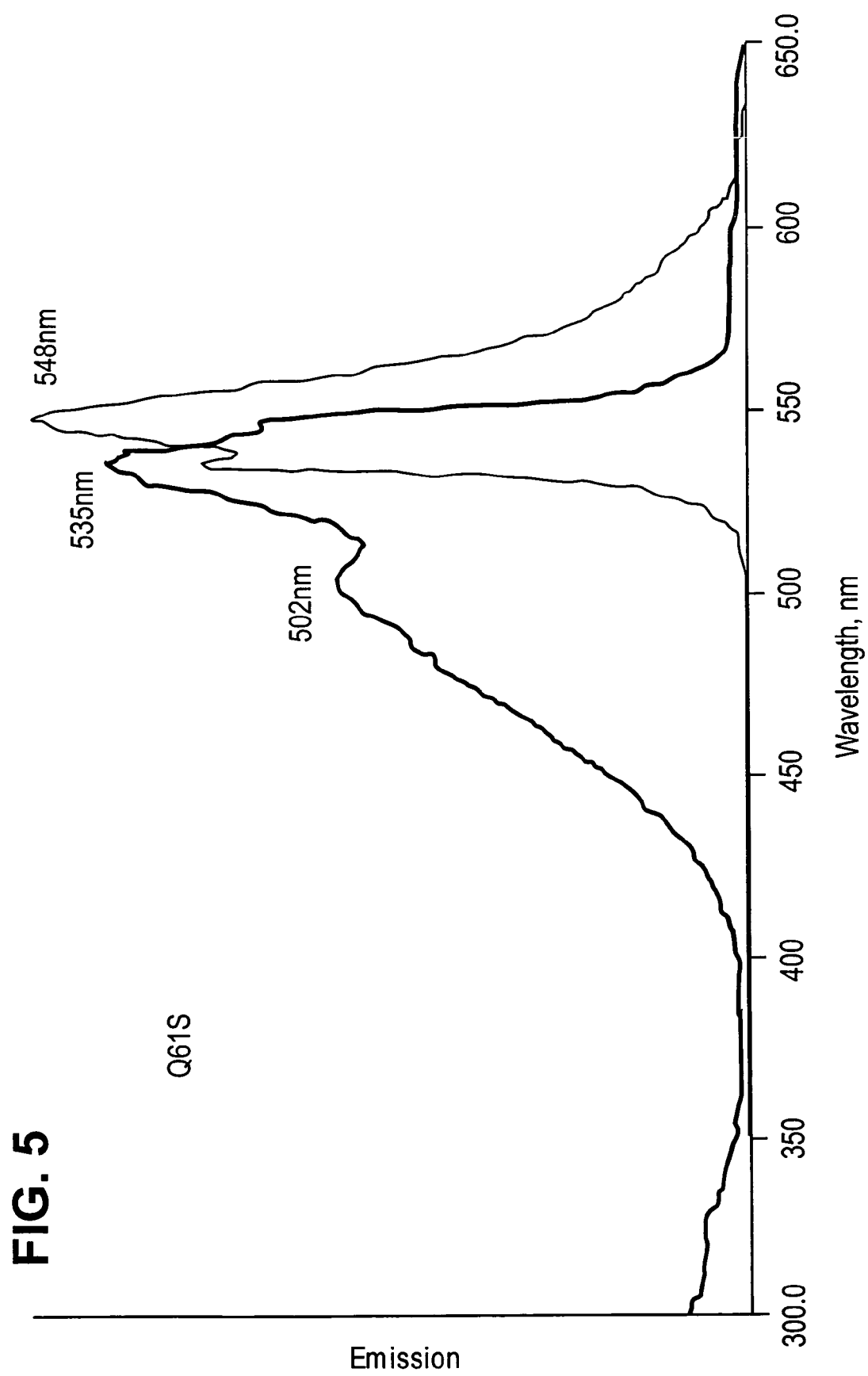
FIG. 5 is a spectrograph of the excitation and emission spectra for the orange fluorescent protein generated by the $Gln^{61}Ser$ point mutation to the OFP encoded by SEQ ID NO:1, and having the primary sequence of SEQ ID NO:28.
Figure 6:
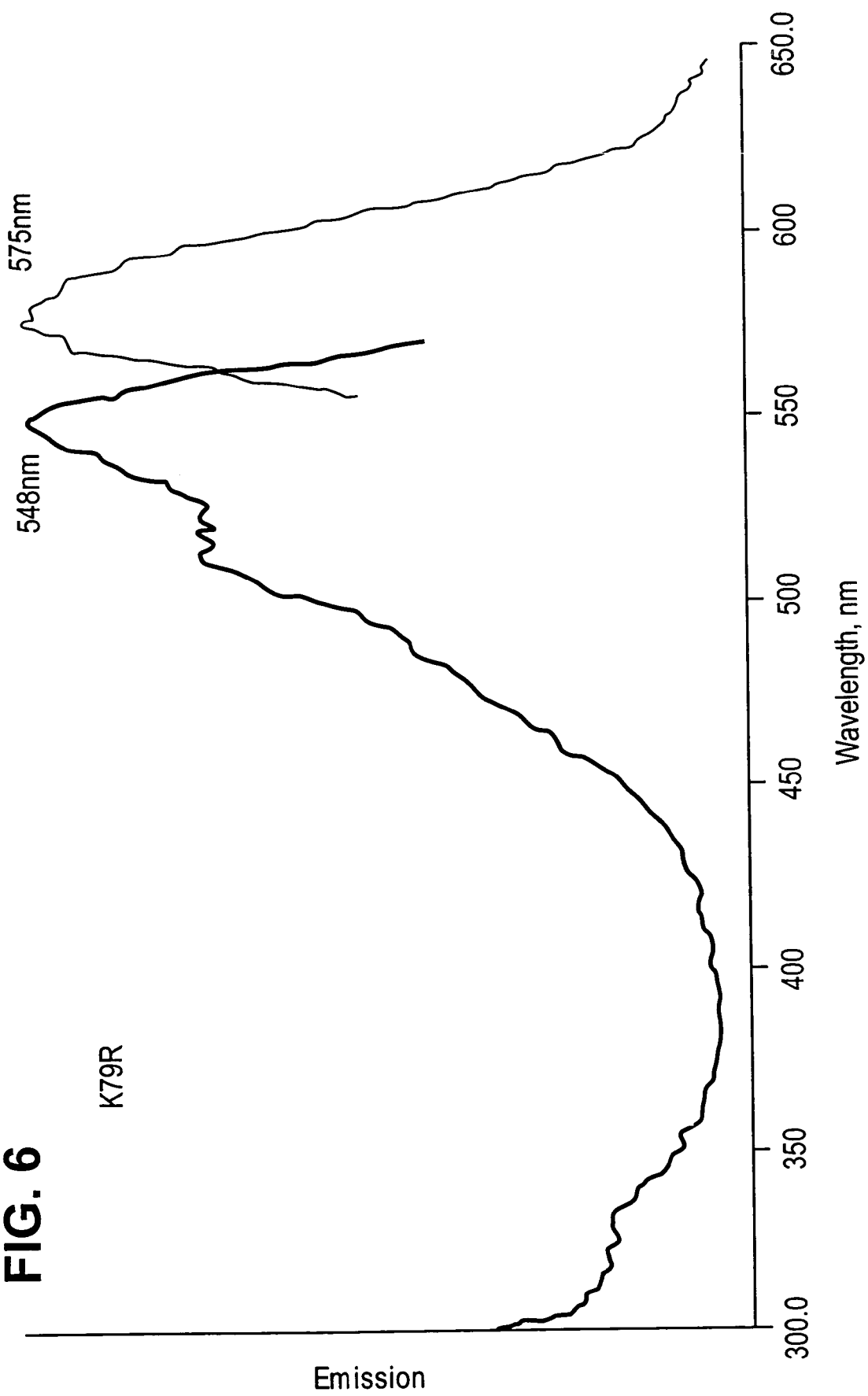
FIG. 6 is a spectrograph of the excitation and emission spectra for the orange fluorescent protein generated by the $Lys^{79}Arg$ point mutation to the OFP encoded by SEQ ID NO:1, and having the primary sequence of SEQ ID NO:29.

As is apparent from amino acid sequence homologies for spontaneously fluorescent proteins having a p-hydroxybenzylidene-imidazolidinone component to their chromophore (Table 2, below), the structure required to maintain a derived chromophore in a functional orientation does not require any consistent, meaningful amino acid sequence homology. Thus OFP molecules of the present invention include mutant forms having primary sequence heterogeneity. In some cases, this heterogeneity may result in proteins having diverse spectral properties. For example, FIGS. 2 through 6 illustrate the divergent spectral properties of a family of OFP's whose primary amino acid sequence is based on that of SEQ ID NO:2. The spectra of the protein having the amino acid sequence disclosed in SEQ ID NO:2 is given in FIG. 2 and designated wild-type OFP. The other proteins of the family differ in sequence from SEQ ID NO:2 by a single amino acid substitution. Three of these substitutions are outside the sequence segment containing the chromophore, e.g., $Y^{37}F$ (FIG. 3), $C^{48}S$ (FIG. 4), and $K^{79}R$ (FIG. 6). One of the substitutions is in the OFP chromophore itself, e.g., $Q^{61}S$ (FIG. 5).

From the foregoing discussion, it will be appreciated that so long as a mutation or other sequence alteration does not result in an OFP that has complete loss of fluorescence, the resultant protein will be considered a functional equivalent for the purposes of the invention. Indeed, all amino acid replacements that yield proteins with different spectral properties fall within the scope of the invention, provided sequence of the amino acid pentamer forming the chromophore is not altered.

Any biomolecule can be readily tagged through fusion with OFP, either through expression of nucleic acid fusion construct or by creating tagged biomolecules in vitro and then injecting them into a cell. This type of tagging allows for assays that track the movement and location of proteins in living cells, track the migration of cells within a living organism, monitor molecular movement through FRET analysis, sort cells based on gene expression (FACS), and track expression from inducible promoters. As OFPs readily fluoresce in response to light of correct wavelength, techniques such as fluorescent microscopy and laser confocal microscopy allow for the monitoring of the cellular location and translocation of OFP-tagged biomolecules. Similarly, the fluorescent properties of OFP-tagged molecules allow for cellular migration to be monitored in, for example, embryological studies, or in the monitoring of metastatic tumors. Coupling a nucleic acid encoding OFP to a tissue specific or inducible promoter allows for the study of the activation of the promoter. Such constructs can be used, for example, in toxicology and drug studies.

II. Isolating Genes Encoding OFP

One of skill in the art will recognize many ways of generating alterations in a given nucleic acid sequence. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Berger and Kimmel, *Guide to Molecular Cloning Techniques, Methods in Enzymology* Volume 152 Academic Press, Inc., San Diego, Calif. (Berger); Sambrook et al. (2001) *Molecular Cloning: A Laboratory Manual* (3$^{rd}$ ed.) Vol. 1-3, Cold Spring Harbor Laboratory, Cold Spring Harbor Press, N.Y., (Sambrook); and *Current Protocols in Molecular Biology*, F. M. Ausubel et al., eds., *Current Protocols*, a joint venture between Greene Publishing Associates, Inc. and John Wiley & Sons, Inc., (1994 Supplement) (Ausubel); Pirrung et al., U.S. Pat. No. 5,143,854; and Fodor et al., *Science*, 251:767-77 (1991). Product information from manufacturers of biological reagents and experimental equipment also provide information useful in known biological methods. Such manufacturers include the SIGMA Chemical Company (Saint Louis, Mo.), R&D systems (Minneapolis, Minn.), Pharmacia LKB Biotechnology (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersberg, Md.), Fluka Chemica-Biochemika Analytika (Fluka Chemie AG, Buchs, Switzerland), and Applied Biosystems (Foster City, Calif.), as well as many other commercial sources known to one of skill. Using these techniques, it is possible to substitute at will any nucleotide in a nucleic acid that encodes any OFP disclosed herein or any amino acid in an OFP described herein for a predetermined nucleotide or amino acid.

A. General Recombinant Methods

This invention relies on routine techniques in the field of recombinant genetics. Basic texts disclosing the general methods of use in this invention include Sambrook et al., *Molecular Cloning: A Laboratory Manual* (3$^{rd}$ ed. 2001);

Kriegler, *Gene Transfer and Expression: A Laboratory Manual* (1990); and *Current Protocols in Molecular Biology* (Ausubel et al., eds., 1994)).

For nucleic acids, sizes are given in either kilobases (Kb) or base pairs (bp). These are estimates derived from agarose or acrylamide gel electrophoresis, from sequenced nucleic acids, or from published DNA sequences. For proteins, sizes are given in kilodaltons (kDa) or the number of amino acid residues. Proteins sizes are estimated from gel electrophoresis, from automated protein sequencing, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.*, 22:1859-1862 (1981), using an automated synthesizer, as described in Van Devanter et. al., *Nucleic Acids Res.*, 12:6159-6168 (1984). Purification of oligonucleotides is by either native acrylamide gel electrophoresis or by anion-exchange HPLC as described in Pearson & Reanier, *J. Chrom.*, 255:137-149 (1983).

The sequence of the cloned genes and synthetic oligonucleotides can be verified after cloning using, e.g., the chain termination method for sequencing double-stranded templates of Wallace et al., *Gene*, 16:21-26 (1981).

B. Cloning Methods for Isolating Nucleic Acids

In general, the nucleic acid sequences encoding SFP's and related nucleic acid sequence homologues are cloned from cDNA and genomic DNA libraries or isolated using amplification techniques with oligonucleotide primers. For example, OFP sequences are typically isolated from (genomic or cDNA) libraries of sea anemones, jellyfish, corals and sea pansies, by hybridizing with a nucleic acid probe or polynucleotide, the sequence of which can be derived from SEQ ID NO:1. By way of example, *Cerianthus* sp., provide a suitable source for OFP mRNA and DNA. Preferably, the template for the amplification is first strand cDNA derived from a *Cerianthus* sp. gene.

Amplification techniques using primers can also be used to amplify and isolate OFP coding sequences from cellular DNA or mRNA. For example, the following primers can be used to amplify nucleic acids encoding OFP from sea anemones, jellyfish, corals and sea pansies sources:

```
Primer set 1:

OFP-M13 forward primer
5'-ATGAAGGGGAATGTCAACAATCAT-3'        SEQ ID NO:12

OFP-STOP reverse primer
5'-TTACTTGGGAAGATCACTGACGAG-3'        SEQ ID NO:13

Primer set 2:

OFP-158 forward primer
5'-ACGGCATTTCAGTATGGTTTCCGCGTA-3'     SEQ ID NO:14

OFP-M131 reverse primer
5'-CATCACTGGCCCATTCGGCGGGAAGTT-3'     SEQ ID NO:15
```

These primers can be used, e.g., to amplify either the full-length sequence or a probe of one to several hundred nucleotides, which is then used to screen a library for a full-length OFP coding sequence.

Nucleic acids encoding the OFβ can also be isolated from expression libraries using antibodies as probes. Such polyclonal or monoclonal antibodies can be raised using the sequence of SEQ ID NO:2, or any immunogenic portion thereof.

OFP polymorphic variants, orthologs, and alleles that are substantially identical to the coding region of OFP can be isolated using OFP nucleic acid probes and oligonucleotides under stringent hybridization conditions, by screening genomic or cDNA libraries.

cDNA Libraries

Preparation of cDNA libraries can be performed by standard techniques well-known in the art. Well-known cDNA library construction techniques can be found for example, in Sambrook et al., 2001, *Molecular Cloning: A Laboratory Manual* ($3^{rd}$ ed.); Cold Spring Harbor Laboratory, Cold Spring Harbor, N.Y.

To make a cDNA library, one should choose a source that is rich in SFP mRNA, e.g., sea anemones, jellyfish, corals and sea pansies. The mRNA is then made into cDNA using reverse transcriptase, ligated into a recombinant vector using T4 DNA ligase, and transformed into a recombinant bacterial host for propagation, screening and cloning. Methods for making and screening cDNA libraries are well-known (see, e.g., Gubler & Hoffman, *Gene*, 25:263-269 (1983); Sambrook et al., supra; Ausubel et al., supra).

An OFP-containing cDNA library constructed in a bacteriophage or plasmid shuttle vector can be screened, for example, with a labeled oligonucleotide probe designed from the nucleic acid sequence of SEQ ID NO:1. The oligonucleotide probe design can be a partial cDNA encoding OFP, obtained by specific PCR amplification of OFP DNA fragments using degenerate oligonucleotide primers based on the amino acid sequence determined from N-terminal amino acid sequencing of OFP, such as SEQ ID NO:3. Alternatively PCR amplification techniques, such as those discussed in detail below, can be used to isolate the OFP-encoding cDNA.

It will be readily apparent to those skilled in the art that other types of libraries, as well as libraries constructed from other cell types or species types, may be useful for isolating an OFP-encoding cDNA or a homologue of an OFP-encoding cDNA. Other types of libraries include, but are not limited to, cDNA and genomic libraries derived from cells or cell lines other than *Cerianthus* sp., such as sea anemones, jellyfish, corals and sea pansies or any other such host which may contain OFP-encoding cDNA.

Genomic Libraries

For a genomic library, the DNA is extracted from the tissue and either mechanically sheared or enzymatically digested to yield fragments of about 12-20 Kb. The fragments are then separated by gradient centrifugation from undesired sizes and are constructed in bacteriophage λ vectors. These vectors and phage are packaged in vitro. Recombinant phage are analyzed by plaque hybridization as described in Benton & Davis, *Science*, 196:180-182 (1977). Colony hybridization is carried out as generally described in Grunstein et al., *Proc. Natl. Acad. Sci. USA.*, 72:3961-3965 (1975). See also, Gussow, D. and Clackson, T., *Nucl. Acids Res.*, 17:4000 (1989).

PCR Amplification

Polymerase chain reaction, or other in vitro amplification methods, may also be useful, for example, in cloning nucleic acid sequences encoding proteins to be expressed; in making nucleic acids to use as probes for detecting the presence of OFP encoding mRNA in physiological samples; for nucleic acid sequencing, or other purposes (see U.S. Pat. Nos. 4,683,195 and 4,683,202; *PCR Protocols. A Guide to Methods and Applications* (Innis et al., eds, 1990)). Such methods can be used to PCR amplify OFP nucleic acid sequences directly from mRNA, or from either genomic or cDNA libraries. Degenerate oligonucleotides can be designed to amplify OFP homologues using the sequences provided herein (e.g., SEQ ID NO:4 to 11). Restriction endonuclease sites can be incorporated into the primers. Genes amplified by the PCR reaction can be purified from agarose gels and cloned into an appropriate vector.

PCR techniques include 5' and/or 3' RACE techniques, both being capable of generating a full-length cDNA sequence from a suitable cDNA library (Frohman, et al., *Proc. Natl. Acad. Sci. USA*, 85:8998-9002 (1988)). The strategy involves using specific oligonucleotide primers for PCR amplification of OFP cDNA. These specific primers are designed through identification of nucleotide sequences either in the cDNA itself, and/or the vector comprising the cDNA. In an exemplary method, a full-length OFP cDNA was isolated by screening a tube anemone (*Cerianthus* sp.) λ phage cDNA library with degenerate primers. The degenerate primers ("guessmers", SEQ ID NO:4 to 11) were based on an N-terminal amino acid sequence (SEQ ID NO:3) generated from the purified OFP protein. The degenerate primers, together with Invitrogen GeneRacer™ Oligo-dT primer (SEQ ID NO:16), were used to amplify the OFP cDNA using the 3' RACE method discussed in detail below.

Synthetic Nucleic Acid Constructs

Synthetic oligonucleotides can also be used to construct recombinant OFP genes for use as probes or for expression of protein. This method is performed using a series of overlapping oligonucleotides usually 40-120 bp in length, representing both the sense and non-sense (antisense) strands of the gene. These DNA fragments are then annealed, ligated and cloned. Alternatively, amplification techniques can be used with precise primers to amplify a specific subsequence of the OFP gene. The specific subsequence is then ligated into an expression vector.

C. Expression of OFPs in Prokaryotes and Eukaryotes

The nucleic acids and proteins of the present invention can be expressed in a variety of host cell types, both prokaryotic and eukaryotic. Although some host systems are able to incorporate "naked" nucleic acids devoid of regulatory sequences (e.g., through recombination), generally the nucleic acid must be incorporated into a suitable expression vector to be expressed.

Suitable expression vectors typically comprise regulatory sequences suitable for expression of the nucleic acid in the host cell. These regulatory sequences are necessarily operably linked to the nucleic acid to control its expression. The expression vector may optionally comprise other regulatory, replication or manipulation sequences to aid in the expression and incorporation of the nucleic acid into the expression vector, as required by the particular application being pursued.

For example, to obtain a high level expression of OFP protein in a prokaryotic system, it is essential to construct expression vectors that contain, at a minimum; a strong promoter to direct transcription, a ribosome-binding site for translational initiation, a transcription/translation terminator, a bacterial replicon, and unique restriction sites in nonessential regions of the plasmid to allow insertion of foreign nucleic acids. Other factors may also be carried on the expression vector, such as selectable and/or scoreable markers, such as an antibiotic resistance gene that is expressed when the expression vector has been constructed and is functioning properly.

Expression Vectors

Suitable expression vectors for OFP and related sequences include plasmids, viruses, bacteriophage, integratable DNA fragments, and other vehicles that enable the integration of DNA fragments into the genome of the host. Plasmids are the most commonly used form of vector but all other forms of vectors which serve an equivalent function and which are, or become, known in the art are suitable for use herein. See, e.g., Pouwels, et al. (1985 and Supplements) *Cloning Vectors: A Laboratory Manual*, Elsevier, N.Y.; Rodriquez, et al. (eds.) *Vectors: A Survey of Molecular Cloning Vectors and Their Uses*, Buttersworth, Boston, 1988; and Luckow, V. A. and Summers, M. D., *BioTechnology*, 6:47-55 (1988) all of which are incorporated herein by reference.

Expression vectors used to transform host cells preferably contain DNA sequences to initiate transcription, and sequences to control the translation of the OFP nucleic acid sequence. These sequences are referred to as regulatory elements. To obtain a high level expression of a cloned gene, such as those cDNAs encoding OFP, a regulatory element typically included in an expression vector is a strong promoter. Suitable bacterial promoters are well-known in the art and described, e.g., in Sambrook et al., and Ausubel et al., supra; Herskowitz, I. and Hagen, D., *Ann. Rev. Genet.*, 14:399-445 (1980); and Yanofsky, C., *J Bacteriol.*, 158: 1018-1024 (1984).

Exemplary yeast promoters can be found in Hitzeman et al., *J. Biol. Chem.*, 255:12073-12080 (1980); Alber and Kawasaki, *J. Mol. Appl. Gen.*, 1:419-434 (1982); Young et al., in *Genetic Engineering of Microorganisms for Chemicals* (Hollaender et al, eds.), Plenum Press, New York, 1982; U.S. Pat. No. 4,599,311 and Russell et al., *Nature*, 304:652-654 (1983). Other exemplary promoter systems are described in McKnight et al., *The EMBO J.*, 4:2093-2099 (1985) (fungal ADH3 promoter); and Vasuvedan et al., *FEBS Lett.*, 311:7-11 (1992) (the insect polyhedrin promoter).

Other regulatory elements that may be incorporated into expression vectors include enhancer elements (see, *Enhancers and Eukaryotic Expression*, Cold Spring Harbor Press, Cold Spring Harbor, N.Y. 1983), termination sequences (Palmiter et al., op. cit.); and intron splice sequences (Sprague et al, *J. Virol.*, 45:773-781 (1983). Expression vectors may also optionally contain selectable markers, such as the gene coding for dihydrofolate reductase (DHFR) or the *Schizosaccharomyces pombe* TPI gene (described by Russell, P. R., *Gene*, 40:125-130 (1985)). The cloning vector containing the regulatory elements is cleaved using restriction enzymes and adjusted in size as necessary or desirable and ligated with sequences encoding the OFP protein by means well-known in the art.

Host Cells Suitable for OFP Expression

OFPs can be expressed in any host cell capable of accepting and expressing a DNA construct or expression vector of the invention. Suitable host cells include bacteria, yeast, fungi and higher eukaryotic cells, such as plant and mammalian cells. Exemplary bacterial host cells include gram-positive bacteria (Palva et al., *Gene*, 22:229-235 (1983); Mosbach et al., *Nature*, 302:543-545 (1983), and gram-negative bacteria such as *Echerichia coli* (cf. Sambrook et al., supra). Examples of suitable yeast cells include *Saccharomyces* sp. or *Schizosaccharomyces* sp. Other suitable fungal hosts include *Aspergillus* sp., *Neurospora* sp., *Fusarium* sp. or *Trichoderma* sp., in particular strains of *A. oryzae*, *A. nidulans* or *A. niger*.

Higher eukaryotic cells grown in tissue culture are often the preferred host cells for expression of the functionally active OFP protein. In principle, any higher eukaryotic tissue culture cell line is workable, e.g., insect baculovirus expression systems, whether from an invertebrate or vertebrate source. Mammalian cells are particularly preferred.

Examples of suitable mammalian cell lines include He—La cells, Chinese hamster ovary (CHO) cell lines, baby rat kidney (BRK) cell lines, insect cell lines, bird cell lines, and monkey (COS) cell lines.

Primary cell lines are also contemplated for use with this invention. These include, by way of example only, bone marrow cells, nerve cells, lung epithelial cells and hepatocytes. Such cells are often manipulated, e.g., to introduce a beneficial gene, and then re-introduced into the animal from which they were originally obtained. This technique is often termed ex vivo gene therapy.

Transfection of Host Cells

Standard transfection methods are used to introduce the DNA constructs and expression vectors of the present invention to host cells. Transformation of both eukaryotic and prokaryotic cells are performed according to standard techniques (see, e.g., Morrison, *J. Bact.*, 132:349-351 (1977); Clark-Curtiss & Curtiss, *Methods in Enzymology*, 101:347-362 (Wu et al., eds, 1983). Transformed host cells usually express OFP protein or its fragments, but for purposes of cloning, amplifying, and manipulating its DNA do not need to express the protein. This invention further contemplates culturing transformed cells in a nutrient medium, thus permitting OFP protein to accumulate in the culture. The proteins can be recovered from the cells or from the culture medium by standard protein purification techniques described herein.

Methods for transforming bacterial cells are described in Sambrook et al., and Ausubel et al., supra. Yeast cell transformation with heterologous DNA is described, e.g. in U.S. Pat. No. 4,599,311, U.S. Pat. No. 4,931,373, U.S. Pat. Nos. 4,870,008, 5,037,743, and U.S. Pat. No. 4,845,075. Methods of transfecting mammalian cells are described in e.g. Kaufman and Sharp, *J. Mol. Biol.*, 159:601-621 (1982); Southern and Berg, *J. Mol. Appl. Genet.*, 1:327-341 (1982); Loyter et al., *Proc. Natl. Acad. Sci. USA*, 79:422-426 (1982); Wigler et al., *Cell*, 14:725 (1978); Corsaro and Pearson, *Somatic Cell Genetics*, 7:603 (1981), Graham and van der Eb, *Virology*, 52:456 (1973); and Neumann et al., *EMBO J.*, 1:841-845 (1982).

D. Identifying an Isolated Nucleic Acid Encoding OFP.

The nucleic acids and proteins of the invention are detected, confirmed and quantified by any of a number of means well-known to those of skill in the art. The unique quality of the expressed proteins here is that they fluoresce, a property that can be readily and easily observed. Fluorescence assays for the expressed proteins are described in detail below. Other general methods for detecting both nucleic acids and corresponding proteins include analytic biochemical methods such as spectrophotometry, radiography, electrophoresis, capillary electrophoresis, high performance liquid chromatography (HPLC), thin layer chromatography (TLC), hyperdiffusion chromatography, and the like, and various immunological methods such as fluid or gel precipitin reactions, immunodiffusion (single or double), immunoelectrophoresis, radioimmunoassays (RIAs), enzyme-linked immunosorbent assays (ELISAs), immunofluorescent assays, and the like.

The detection of OFP nucleic acids can also be accomplished by Southern analysis (Southern et al., *J. Mol. Biol.*, 98:503 (1975)), Northern analysis, gel electrophoresis, PCR, radiolabeling, scintillation counting, and affinity chromatography. In performing nucleic acid hybridization techniques, the format is not critical. Additional formats include sandwich assays and competition or displacement assays. Hybridization techniques are generally described in "*Nucleic Acid Hybridization, A Practical Approach,*" Ed. Hames, B. D. and Higgins, S. J., IRL Press, 1985; Gall and Pardue, *Proc. Natl. Acad. Sci. USA*, 63:378-383 (1969); and John et al., *Nature,* 223:582-587 (1969). Sandwich assays, for example, are commercially useful hybridization assays for detecting or isolating nucleic acid sequences. Such assays utilize a "capture" nucleic acid covalently immobilized to a solid support and labeled "signal" nucleic acid in solution. The clinical sample will provide the target nucleic acid. The "capture" nucleic acid and "signal" nucleic acid probe hybridize with the target nucleic acid to form a "sandwich" hybridization complex. To be effective, the signal nucleic acid cannot hybridize with the capture nucleic acid.

Labeled signal nucleic acids, whether those described herein or others known in the art are used to detect hybridization. Complementary nucleic acids or signal nucleic acids may be labeled by any one of several methods typically used to detect the presence of hybridized polynucleotides, and discussed in detail below.

An alternative means for determining the level of expression of the OFP gene is in situ hybridization as described in Angerer et al., *Methods Enzymol.*, 152:649-660 (1987). In an in situ hybridization assay cells are fixed to a solid support, typically a glass slide. If DNA is to be probed, the cells are denatured with heat or alkali. The cells are then contacted with a hybridization solution at a moderate temperature to permit annealing of OFP-specific probes that are labeled. The probes are preferably labeled with radioisotopes or fluorescent reporters.

The sequence of the cloned genes and synthetic oligonucleotides can be verified using the chemical degradation method of A. M. Maxam et al., *Methods in Enzymology*, 65:499-560 (1980). The sequence can be confirmed after the assembly of the oligonucleotide fragments into the double-stranded DNA sequence using the method of Maxam and Gilbert, supra, or the chain termination method for sequencing double-stranded templates of R. B. Wallace et al., *Gene*, 16:21-26 (1981). DNA sequencing may also be performed by the PCR-assisted fluorescent terminator method (ReadyReaction DyeDeoxy Terminator Cycle Sequencing Kit, ABI, Columbia, Md.) according to the manufacturer's instructions, using the ABI Model 373A DNA Sequencing System. Sequencing data is analyzed using the commercially available Sequencher program (Gene Codes, Gene Codes, Ann Arbor, Mich.).

III. Constructing Variant OFPs

A. Mutant OFPs

As will be readily apparent to those in the art, to describe a fluorescent protein of the present invention, it is not necessary to provide the entire sequence of any particular OFP. A functional OFP is characterized by a functional OFP chromophore, as defined herein. In order for the chromophore to be functional however, an OFP protein must possess a tertiary structure that provides the chromophore with a suitable environment, particularly support of the correct chromophore orientation, to allow the chromophore to fluoresce. Consequently, minor deletions at either end of the protein sequence are expected to have little or no impact on the fluorescence spectrum of the protein. Moreover, modifications to the primary amino acid sequence that do not perturb the tertiary structure of the protein, including substitution, deletion and insertion of amino acids or chemical modification of amino acid residues of the protein, are expected to modify the absorption and/or emission spectrum of the OFP, but not extinguish fluorescence. Examples of altered fluorescent emission spectra generated from proteis having amino acid modifications (i.e., amino acid substitutions) as described above are depicted in FIGS. 2-6. Therefore, both mutant and wild-type OFP sequences are contemplated, as manifested not only in the complete polypeptide and oligonucleotide sequences discussed herein, but also functionally equivalent portions and mutations thereof (i.e., portions of the polypeptide sequences which exhibit the desired fluorescence properties and oligonucleotide sequences encoding these polypeptide sequences).

A functionally equivalent mutation includes mutations with neutral (or minor) effects on the fluorescent properties of the claimed proteins and mutations with more dramatic effects, including large shifts in absorbance, emission and/or excitation spectra. Whereas some amino acids of the chromophore itself (position 60-64) are obviously important, the locations of neutral mutations suggest that other amino acids of the claimed proteins are less critical to fluorescence, e.g., amino acids 144-160 of SEQ ID NO:2. This is apparent from studies performed on GFP, were the point mutations $Lys^3Arg$; $Asp^{76}Gly$; $Phe^{99}Ile$; $Asn^{105}Ser$; $Glu^{115}Val$; $Thr^{225}Ser$; and $LYS^{238}Glu$ have been found to be neutral (i.e., have no significant impact on the functional properties of the product). Similar neutral substitutions also exist in OFP proteins of the present invention, for example $Ser^8Thr$; $Val^{120}Ile$; $Ala^{159}Val$; $Asn^{171}Gln$; and $Thr^{214}Ser$ (SEQ ID NO:17-21). Other mutations encompassed by the invention modify spectroscopic properties of the protein without altering the amino acid sequence giving rise to the OFP chromophore. For example, the point mutation to wild-type OFP, $Tyr^{37}Phe$, shifts the peaks for the excitation and emission spectra of wild-type OFP (548 nm/565 nm) dramatically towards the blue region of the spectrum (478 nm/497 nm), resulting in an OFP that fluoresces green (see FIGS. 2 and 3). The properties of the $Tyr^{37}Phe$ mutation of wild-type OFP illustrate the point that fluorescent characteristics of the present invention can be dramatically altered by very minor primary sequence alterations (a Tyr to Phe mutation is a conservative change), even when those alterations are distant in sequence from the amino acids forming the chromophore. Additional evidence of the effect of minor changes in primary sequence on OFP Emission spectra are illustrated in FIGS. 4 through 6, showing the changes in emission spectra brought about by single amino acid substitutions $C^{48}S$, $K^{79}R$ and $Q^{61}S$, respectively.

Necessarily, mutations outside the chromophore that modify in character, but do not extinguish completely, the fluorescence of an OFP protein of the present invention are included in the claimed invention.

In addition, various types of fusion sequences that lengthen the resultant protein or serve some functional purpose in the preparation or purification of the protein are also routine and contemplated as within the scope of the present invention. As an example, it is common practice to add amino acid sequences including a polyhistidine tag to facilitate purification of product proteins, as detailed below herein, or "fuse" two molecules through covalent attachment with or without an intervening linker region. Such modifications generally do not significantly alter the salient properties of the molecules making up the fusion protein. OFPs modified in this manner are therefore also contemplated as within the scope of the present invention.

In general, the polypeptides and oligonucleotide sequences of the present invention (in addition to containing at least one of the specific mutations identified herein) will be at least about 55% homologous, more preferably at least about 75% homologous, and most preferably at least about 90% homologous, to the OFP sequence as disclosed in SEQ ID NO:2.

The DNA sequence coding for OFP may also be modified by other means such as by conventional chemical mutagenesis or by insertion, deletion or substitution of one or more nucleotides in the sequence, either as random or site-directed mutagenesis. It is expected that such mutants will exhibit altered optical properties or altered heat stability.

B. Creating Novel OFP's with Heterologous β can Constructs

The preferred structure of OFPs of the present invention is the β can as described by Ormo et al., *Science,* 273:1392-1395 (1996). However, the sequence homologies found amongst fluorescent proteins having the β can structure, including OFP's, are limited as illustrated in Table 2:

TABLE 2

Percentage of protein sequence homologies of OFP with various fluorescent proteins

| | |
|---|---|
| *Ptilosarcus sp.* | 42% |
| *Renilla nuelleri* | 40% |
| RFP (dsFP593) | 40% |
| cFP484 | 39% |
| asFP499 | 39% |
| DsRed (drFP583) | 39% |
| zFP506 | 37% |
| zFP538 | 37% |
| amFP486 | 36% |
| asFP595 | 36% |
| *Renilla reniformis* | 35% |
| drFP4S3 | 35% |
| avGFP | 27% |

Recognition of a tolerance for a high degree of variance in the primary sequence of the polypeptide strands forming the β can has led to the realization of the present invention that virtually any peptide strand forming the β can could be substituted with a heterologous strand of similar length, provided the heterologous strand can take on a stable β strand conformation and is positioned to form part of the antiparallel β can structure.

Of course certain residues in certain strands of the β can are in proximity to the chromophore housed within the structure and potentially interact with the chromophore, affecting its fluorescent properties. Identifying these proximal residues in a novel SFP can be done through routine experimentation based on the methodology developed in identifying such residues in other SFP's (see e.g., U.S. Pat. No. 6,319,669), and the structural characteristics common to all SFP's. Common structural characteristics include the positioning of the chromophore approximately in the middle of the β can (when viewed along the latitudinal axis of the protein) and the observation that the β can structure is very uniform and will readily form provided suitable β strands are correctly positioned in the primary structure of the protein. In designing the heterologous β can structures of the present invention, the practitioner is therefore acquainted with the particular constraints present for the small subset of residues that both form the β can and are in close proximity to the OFP chromophore, and the methods for identifying such residues. Heterologous β can structures of the present invention include, but are not limited to, substituting compatible β strands in an existing protein with synthetic β strands, or β strands from other proteins. With reference to FIG. 1, the present invention also includes proteins with a polypeptide from one SFP at the $A_1$ position and a polypeptide from another SFP at the $A_2$ position. Constructs where both the $A_1$ and the A₂ polypeptides are derived from the same SFP are discussed further in the following section.

C. Creating Novel OFP's by Substituting an OFP Chromophore into Existing β can Constructs As noted in the previous section, despite the disparity in sequence homology shown in Table 2, all of the proteins listed in the table comprise functionally competent fluorescent chromophores within a β can structure. The realization of the present invention is that an OFP chromophore can be substituted for the native chromophore of another SFP, resulting in a novel OFP with unique spectroscopic properties. As with the other variant OFP constructs discussed above, creating novel OFP's by substituting an OFP chromophore into the β can of an existing SFP can be accomplished through molecular biological techniques known in the art. For example, if the sequence of the SFP is known, a nucleic acid encoding the SFP can be constructed de novo, and the OFP chromophore inserted simply by altering the codons for the native chromophore to a sequence encoding an OFP chromophore. Alternatively, if the nucleotide sequence around the native SFP chromophore is known, PCR primers can be constructed to amplify the SFP sequence with an OFP chromophore substituted for the native chromophore. Common techniques for generating OFP variants of the present invention are discussed in more detail in the following sections. An exemplary method for substituting an OFP chromophore into a GFP β can is presented in Example 4.

De Novo Synthesis

The DNA construct of the invention encoding OFP, modified OFP or hybrid polypeptide may be prepared synthetically by established standard methods, e.g. the phosphoramidite method described by Beaucage and Caruthers, *Tetrahedron Letters,* 22:1859-1869 (1981), or the method described by Matthes et al., *EMBO J.,* 3:801-805 (1984). According to the phosphoramidite method, oligonucleotides are synthesized, e.g. in an automatic DNA synthesizer, purified, annealed, ligated and cloned in suitable vectors. Moreover, the protein sequence of a number of SFPs has been deduced (e.g., FIG. 7). Using the methods described above, it is within the skill of one in the art to synthesize novel OFPs through de novo synthesis of a polynucleotide that, for example, substantially encodes the cFP484 protein of FIG. 7, with the substitution of a nucleic acid encoding the OFP chromophore pentapeptide, for the nucleic acid sequence encoding amino acids 103-107 in the native cFP484 sequence. The same strategy could be used to create a second novel OFP by substitution of the nucleic acid encoding the OFP chromophore pentapeptide for the nucleic acid encoding amino acids 65-69 in the native DsRed sequence.

Furthermore, the DNA construct may be of mixed synthetic and genomic, mixed synthetic and cDNA or mixed genomic and cDNA origin, prepared by ligating fragments of synthetic, genomic or cDNA origin (as appropriate) in accordance with standard techniques (cf. Sambrook et al., *Molecular Cloning: A Laboratory Manual,* 3$^{rd}$, 2001, Cold Spring Harbor Laboratory, New York, USA). The fragments corresponding to various parts of the entire DNA construct, including the sequence of the substituting OFP chromophore, can optionally be from any source including different SFP's, and combined to form novel OFP's. Alternatively, an OFP chromophore may be "swapped" into different polypeptides or fragments. See, e.g., Cunningham, et al., *Science,* 243:1330-1336 (1989); and O'Dowd, et al., *J. Biol. Chem.,* 263:15985-15992 (1988), each of which is incorporated herein by reference. Thus, new chimeric OFP's exhibiting new combinations of fluorescent properties will result from the functional linkage of the OFP chromophore to alternative heterologous protein scaffolds.

Site-directed Mutagenesis

Site-directed mutagenesis may be used to prepare further variants of nucleic acids encoding OFPs. Site-directed mutagenesis is a technique useful in the preparation of individual peptides, or biologically functional equivalent proteins or peptides, through specific mutagenesis of the underlying DNA. The technique further provides a ready ability to prepare and test sequence variants by introducing one or more nucleotide sequence changes into the DNA.

The technique of site-directed mutagenesis is generally well-known in the art as exemplified by publications (Adelman et al., *DNA,* 2:183, (1983)). As will be appreciated, the technique typically employs a phage vector that exists in both a single-stranded and double-stranded form. Typical vectors useful in site-directed mutagenesis include vectors such as the M13 phage (Messing et al., *Third Cleveland Symposium on Macromolecules and Recombinant DNA,* Ed: A. Walton, Elsevier, Amsterdam, (1981)). These phages are readily commercially available and their use is generally well-known to those skilled in the art. Double-stranded plasmids are also routinely employed in site-directed mutagenesis, which eliminates the step of transferring the gene of interest from a plasmid to a phage.

In general, site-directed mutagenesis in accordance herewith is performed by first obtaining a single-stranded nucleic acid that includes within its sequence the coding sequence for an SFP or SFP peptide. For example, an oligonucleotide that is generally complimentary with the region of the SFP comprising the chromophore but bearing nucleotide substitutions required to encode in frame the OFP chromophore pentapeptide at the position of the original SFP chromophore is generated. This approach is detailed in examples 4 and 5, below. Such oligonucleotides can be generated for example by the de novo (phosphoramidite) synthesis techniques noted above. This oligonucleotide is then annealed with the single-stranded nucleic acid comprising the sequence for the SFP, and subjected to DNA polymerizing enzymes such as *E. coli* polymerase I Klenow fragment, in order to complete the synthesis of the mutation-bearing strand. A heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement. Typically, a primer of about 17 to 25 nucleotides in length is preferred, with about 5 to 10 residues on both sides of the junction of the sequence being altered. Suitable techniques are also described in U.S. Pat. No. 4,888,286, incorporated herein by reference.

The preparation of sequence variants of an OFP using site-directed mutagenesis is provided as a means of producing novel, potentially useful OFP species and is not meant to be limiting as there are other ways in which sequence variants of OFP genes may be obtained. For example, recombinant vectors comprising a nucleic acid encoding OFP may be treated with mutagenic agents to obtain sequence variants (see, e.g., the method described by Eichenlaub, *J. Bacteriol,* 138:559-566 (1979)).

Although the foregoing methods are suitable for use in mutagenesis, the use of the polymerase chain reaction (PCR) is generally now preferred. Briefly, the SFP (e.g., GFP) chromophore pentapeptide is replaced by the OFP chromophore pentapeptide by amplifying a nucleic acid encoding the SFP chromophore with primers generally specific for the SFP nucleotide sequence, but were at least one of the primers comprises nucleotide substitutions creating an in frame coding sequence for the OFP chromophore pentapeptide. This process is discussed in more detail in examples 4 and 5. It should be emphasized again that mutations in the OFP primary sequence outside the chromophore itself may have a significant impact on the fluorescent properties of the protein, as exemplified in FIGS. 2, 3, 4 and 6.

Resulting reaction products should be examined by e.g., restriction mapping, electrophoresis and/or automated nucleotide sequencing to confirm the desired product is obtained. The synthesized nucleic acid containing the OFP chromophore pentapeptide can then be expressed in a suitable system, as described above.

IV. Purification of OFPs

Culture and purification techniques are those standard in the art. (cf., Colley et al., *J. Biol. Chem.*, 264:17619-17622 (1989), and Guide to Protein Purification, in Vol. 182 of Methods in Enzymology (Deutscher ed., 1990), Morrison, D. A., *J. Bact.*, 132:349-351 (1977), or by Clark-Curtiss et al., *Methods in Enzymology*, 101:347-362 (1983), eds. R. Wu et al., Academic Press, New York. (for suitable media, see the catalogues of the American Type Culture Collection)). Additional isolation techniques are described in detail in the following sections.

Either naturally occurring or recombinant OFP can be purified for use in functional assays. Naturally occurring OFP can be purified, e.g., from *Cerianthus* sp., or any other source of an OFP homologue. Recombinant OFP can be purified from any suitable expression system.

OFPs may be purified to substantial purity by standard techniques, including column chromatography, immunopurification methods, electrophoresis, centrifugation, crystallization, isoelectric focusing and others (see, e.g., Scopes, *Protein Purification: Principles and Practice* (1982); U.S. Pat. No. 4,673,641; Ausubel, et al. (1987 and periodic supplements) *Current Protocols in Molecular Biology*; Deutscher (1990) "*Guide to Protein Purification*" in *Methods in Enzymology* vol. 182, and other volumes in this series; and manufacturers' literature on use of protein purification products, e.g., Pharmacia, Piscataway, N.J., or Bio-Rad, Richmond, Calif.; and Sambrook et al., supra).

A number of procedures can be employed when recombinant OFP is being purified. For example, proteins having established molecular adhesion properties can be reversibly fused to the OFP. With the appropriate ligand, OFP can be selectively adsorbed to a purification column and then freed from the column in a relatively pure form. The fused protein is then removed by enzymatic activity. Finally OFP could be purified using immunoaffinity columns.

A. Purification from Recombinant Bacteria.

Recombinant proteins are expressed by transformed bacteria in large amounts, typically after promoter induction; but expression can be constitutive. Promoter induction with IPTG is one example of an inducible promoter system. Bacteria are grown according to standard procedures in the art, as noted above. Fresh or frozen bacteria cells are used for isolation of protein.

Proteins expressed in bacteria may form insoluble aggregates ("inclusion bodies"). Several protocols are suitable for purification of OFP from inclusion bodies. For example, purification of inclusion bodies typically involves the extraction, separation and/or purification of inclusion bodies by disruption of bacterial cells, e.g., by incubation in a buffer of 50 mM Tris/HCl pH 7.5, 50 mM NaCl, 5 mM MgCl$_2$, 1 mM DTT, 0.1 mM ATP, and 1 mM PMSF. The cell suspension can be lysed using 2-3 passages through a French Press, homogenized using a Polytron (Brinkmann Instruments, Inc.) or sonicated on ice. Alternate methods of lysing bacteria are apparent to those of skill in the art (see, e.g., Sambrook et al., supra; Ausubel et al., supra). OFP in the lysate can then be purified using standard techniques (see, e.g., Colley et al., *J. Biol. Chem.*, 264:17619-17622 (1989); *Guide to Protein Purification*, in *Methods in Enzymology*, vol. 182 (Deutscher, ed., 1990)).

If necessary, the inclusion bodies are solubilized, and the lysed cell suspension is typically centrifuged to remove unwanted insoluble matter. OFP comprising the inclusion bodies may be renatured by dilution or dialysis with a compatible buffer. Suitable solvents include, but are not limited to urea (from about 4 M to about 10 M), formamide (at least about 80%, volume/volume basis), and guanidine hydrochloride (from about 4 M to about 8 M). Some solvents, which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is reversible and renaturation may occur upon removal (by dialysis, for example) or dilution of the denaturant, allowing re-formation of immunologically and/or biologically active protein. Other suitable buffers are known to those skilled in the art. It is important to note that the OFP structure is extremely stable once formed, and readily folds in the correct conformation when denaturant is removed.

Alternatively, it is possible to purify OFP from bacteria periplasm. When OFP is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM MgSO$_4$ and kept in an ice bath for approximately 10 minutes. The cell suspension is centrifuged and the supernatant decanted and saved. The recombinant proteins present in the supernatant can be separated from the host proteins by standard separation techniques well-known to those of skill in the art.

B. Standard Purification Techniques

Gel Filtration

The molecular weight of OFP (e.g., approximately 25.2 kDa) can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut-off greater than the molecular weight of the protein of interest. The recombinant protein will pass through the membrane into the filtrate. The filtrate can then be chromatographed as described below.

Exchange Chromatography

OFP can also be separated from other proteins on the basis of size, net surface charge, hydrophobicity, and affinity for ligands. In addition, antibodies raised against proteins can be conjugated to column matrices and the proteins immunopurified. All of these methods are well-known in the art. It will be apparent to one of skill that chromatographic techniques can be performed at any scale and using equipment from many different manufacturers (e.g., Pharmacia Biotech).

Tagging Techniques

Purification segments, or "affinity tags" can be fused to appropriate portions of the receptor to assist in isolation and production. For example, the FLAG™ sequence, or a functional equivalent, can be fused to the protein via a protease-removable sequence, allowing the FLAG™ sequence to be recognized by an affinity reagent, and the purified protein subjected to protease digestion to remove the extension. Many other equivalent segments exist, e.g., poly-histidine segments possessing affinity for heavy metal column reagents. See, e.g., Hochuli, *Chemische Industrie,* 12:69-70 (1989); Hochuli, *Genetic Engineering, Principle and Methods,* 12:87-98 (1990), Plenum Press, N.Y.; and Crowe, et al. (1992) *OIAexpress: The High Level Expression & Protein Purification System*, QIAGEN, Inc. Chatsworth, Calif.; which are incorporated herein by reference.

His-tag

The OFP construct can also contain a string of histidine residues, incorporated at the amino or carboxyl terminal of the OFP. The polyhistidine tag allows convenient isolation of the protein in a single step by nickel-chelate chromatography. When a protein that has been "his-tagged" is placed on the nickel column, the histidine residues form a chelate complex with the nickel bound to the column, immobilizing the tagged protein. Contaminating components of the solution comprising the tagged protein can be washed away prior to elution of the tagged protein with a suitable competing chelator, typically imidazole.

The polyhistidine tag can be added to the protein through the use of peptide linkers as described in detail below. Alternatively, the tag can be linked to OFP by appending a nucleic acid encoding the tag onto the coding region of OFP, the resulting construct being incorporated into a suitable expression vector that is subsequently used to transform an appropriate host cell. Protein produced in the transformed host cell can then be purified as noted above and described in detail in Example 1.

Epitope Tagging

Epitope tags are another useful sequence that can be included in the OFP construct. The epitope tag can consist of an amino acid sequence that allows affinity purification of the activated protein (e.g., on immunoaffinity or chelating matrices). Thus, by including an epitope tag on the activation construct, all of the activated proteins from an activation library can be purified. By purifying the activated proteins away from other cellular and media proteins, screening for novel proteins and enzyme activities can be facilitated. In some instances, it may be desirable to remove the epitope tag following purification of the activated protein. This can be accomplished by including a protease recognition sequence (e.g., Factor Xa or enterokinase cleavage site) downstream from the epitope tag on the activation construct. Incubation of the purified, activated protein(s) with the appropriate protease will release the epitope tag from the proteins(s).

In libraries in which an epitope tag sequence is located in the OFP construct, all of the OFPs can be purified away from all other cellular and media components using affinity purification. In addition to purifying the tagged OFP protein, this method also concentrates the protein sample.

PAGE/blotting

OFPs of the present invention can be purified using native polyacrylamide gel electrophoresis. Briefly, the technique involves preparing a polyacrylamide gel slab by mixing appropriate amounts of acrylamide and bis-acrylamide in a basic buffer solution, typically TRIS® (hydroxymethyl) aminomethane hydrochloride-based, and allowing the mixture to polymerize between a pair of parallel glass plates uniformly-spaced. By modifying the amount of acrylamide added to the mixture, slabs can be optimized for separation of proteins in particular molecular weight ranges. In the case of OFPs, a preferred acrylamide content for the gel would be between 6% and 15%, more preferably between 8% and 12%. The gel is normally loaded and run in the vertical position, with protein resolution resulting by a sieving action of the gel as the proteins are driven through the gel matrix by an electrical current applied across the gel slab. (see Schagger et al., *Anal. Biochem.,* 166:368-379 (1987)).

Once protein resolution is complete, the bands containing OFP are easily recognized as they fluoresce when exposed to a light comprising the appropriate wavelength. The band(s) containing OFP are excised from the gel, and the resulting gel slices placed in a dialysis sack with the appropriate molecular weight cut-off and containing a buffer solution with a pH value preferably between 7 and 9, more preferably between 7.5 and 8.5. The sack is placed on a flat bed electrophoresis unit parallel to the direction of the current. The electrophoresis unit is filled with the same buffer solution placed in the dialysis sack. The electrophoresis unit is run for several hours, preferably overnight, at a low voltage of between 5 and 50 volts, more preferably between 15 and 30 volts (the actual voltage applied depends upon the application, particularly the composition of the buffer solution used in the apparatus).

By subjecting the gel slice containing the OFP protein to the low voltage and current of the flat bed electrophoresis apparatus, the proteins are driven out of the gel slice and into the buffer solution of the dialysis sack. Once electrophoresis is complete, the vacant gel slices can be removed, and the OFP protein in the buffer solution concentrated using any one of the variety of concentration methods known in the art. All chemicals and apparatus used in the methods are described in available scientific literature and commonly available through scientific catalogs. (see, e.g., Scopes, *Protein Purification: Principles and Practice* (1982); Ausubel, et al. (1987 and periodic supplements); *Current Protocols in Molecular Biology*; Deutscher (1990) "*Guide to Protein Purification*" in *Methods in Enzymology* vol. 182, and other volumes in this series; and manufacturers' literature on use of protein purification products, e.g., Pharmacia, Piscataway, N.J., or Bio-Rad, Richmond, Calif.; and Sambrook et al., supra).

Alternatively, proteins resolved by the vertical gel electrophoresis method can be transferred, using Western blotting techniques commonly known in the art, to nylon or PVDF membranes, or the like. Portions of the membranes containing OFP can then be isolated using the fluorescent properties of the protein for identification. The isolated membrane portions can then be analyzed to characterize the fluorescent protein, e.g., Western blotting or N-terminal amino acid sequencing, as described herein. See Mozdzanowsky et al., *Electrophoresis,* 13:59-64 (1992).

Isoelectric Focusing

Isoelectric focusing can be performed in both analytical and preparative applications. The principles of separation are the same regardless of the application, only the quantities of proteins, pH range and quantity of carrier ampholytes employed, and the sample capacity of the apparatus differ between applications.

IEF takes place in a pH gradient and is limited to molecules that can be either positively or negatively charged (amphoteric molecules), like proteins, enzymes and peptides. Protein separation occurs in a pH gradient formed by special amphoteric buffers (ampholytes) having high buffer capacities at their pI (isoelectric point). The pH gradient is produced by an electric field. Before an electric field is applied the gel has a uniform pH-value and almost all the carrier ampholytes are charged. When an electric field is applied, negatively charged ampholytes move towards the anode, the positively charged ampholytes to the cathode. The carrier ampholytes align themselves between the cathode and the anode according to their pI. Hundreds or thousands of carrier ampholytes aligned in this manner form partially overlapping distributions, establishing the pH gradient. As there are no other ionic species in the system, each carrier ampholyte must act as counter ion to other carrier ampholytes consequently each position in the pH gradient will have a unique chemical composition. Electrical conductance and buffer capacity will therefore vary over the pH gradient. Regions with low buffer capacity are more prone to distortion. In preparative experiments with protein loads, buffering capacity form the proteins may affect the pH gradient.

A large number of carrier ampholyte mixtures are available giving different pH gradients. Many can also be obtained in pre-cast gels ready to use. The optimal pH gradient will depend on the purpose of the experiment. For screening purposes, a broad range interval (pH 3-10 or similar) should be used. A narrow pH range interval is useful for careful pI determinations or when analyzing proteins with very similar pI points. Generally, one should not use a narrower gradient than necessary because the shallower gradient will lead to longer focusing times and more diffuse bands. When choosing pH gradient one should be aware that the interval stated by the manufacturer can only be an approximation. The exact gradient obtained depends on many factors such as choice of electrolyte solutions, gradient medium (PAA or agarose), focusing time etc.

In polyacrylamide gels, pore size can be accurately controlled by the total acrylamide-concentration and degree of cross-linking (relationship between acrylamide and bisacrylamide). When cross-linking is kept constant and total concentration increases pore size will decrease (and diffusion is reduced). Gel solution is made from appropriate amounts of acrylamide (~5%), ampholyte (~2%), double distilled H$_2$O, and riboflavin 5' phosphate (for photopolymerization). Gels (approx 250×120×1 mm) are mold between two glass-plates and polymerized overnight in UV-light (requires a pH in the solution >5-6).

Once the pH gradient has formed in the gel, samples are applied cathodically. The charged components in the samples will migrate according to their net charge, until they encounter a region of the gel were the pH is equal to the sample components pI. At this equivalence point, the protein is uncharged and stops migrating. Should the sample component diffuse into an adjacent pH-environment, it will rapidly acquire a charge and move back to the position corresponding to its pI. Most proteins have a pI in the range of 5 to 8.5, with the OFP formed by the polypeptide of SEQ ID NO:2 has a pI of between 6 and 8. Further explanation of IEF techniques may be found in Scopes, *Protein Purification: Principles and Practice* (1982); *Current Protocols in Molecular Biology*; Deutscher (1990) "*Guide to Protein Purification*" in *Methods in Enzymology* vol 182, and other volumes in this series; and manufacturers' literature on use of protein purification products, e.g., Bio-Rad, Richmond, Calif; and Sambrook et al., supra).

The Rotofor™, produced by the Bio-Rad Corporation, is an example of an apparatus suitable for the purification of relatively large quantities of proteins by IEF. By way of example, the OFP formed from the polypeptide of SEQ ID NO:2 can be purified using the Bio-Rad Rotofor™ apparatus in a manner described by the manufacturer. Briefly, after a gradient-forming pre-run of the system with 18 ml 2% ampholyte (pH 3 to 10) for 1 hour, OFP is injected into the system. After focusing the system for several hours, OFPs are enriched in fractions having a pH between 6 and 8. OFP is easily identified by illumination with ultra violet light.

V. Analyzing OFP's

A. Labels for Proteins and Nucleic Acids

The particular label or detectable group used in the assay is not a critical aspect of the invention, as long as it does not significantly interfere with the specific binding of the antibody or protein used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™); fluorescent dyes and techniques capable of monitoring the change in fluorescent intensity, wavelength shift, or fluorescent polarization (e.g., fluorescein isothiocyanate, Texas red, rhodamine, and the like); radiolabels (e.g., $^3$H, $^{125}$I, $^{35}$S, $^{14}$C, or $^{32}$P); enzymes (e.g., horse radish peroxidase, alkaline phosphatase and others commonly used in an ELISA); and colorimetric labels such as colloidal gold or colored glass or plastic beads (e.g., polystyrene, polypropylene, latex, etc.). For exemplary methods for incorporating such labels, see U.S. Pat. Nos. 3,940,475; 3,817,837; 3,850,752; 3,939,350; 3,996,345; 4,277,437; 4,275,149; and 4,366,241.

The label may be coupled directly or indirectly to the desired component of the assay according to methods well-known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecule (e.g., streptavidin), that is either inherently detectable or covalently bound to a signal system, such as a detectable enzyme, a fluorescent compound, or a chemiluminescent compound. The ligands and their targets can be used in any suitable combination with antibodies that recognize OFP, or secondary antibodies that recognize anti-OFP antibodies. Other possibilities for indirect labeling include biotinylation of one constituent followed by binding to avidin coupled to one of the above label groups.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well-known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge-coupled devices (CCDs) or photomultipliers and the like. Similarly, enzymatic labels may be detected by providing the appropriate substrates for the enzyme and detecting the resulting reaction product. Finally, simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

B. Fluorescent Analysis Techniques

Figure 2:
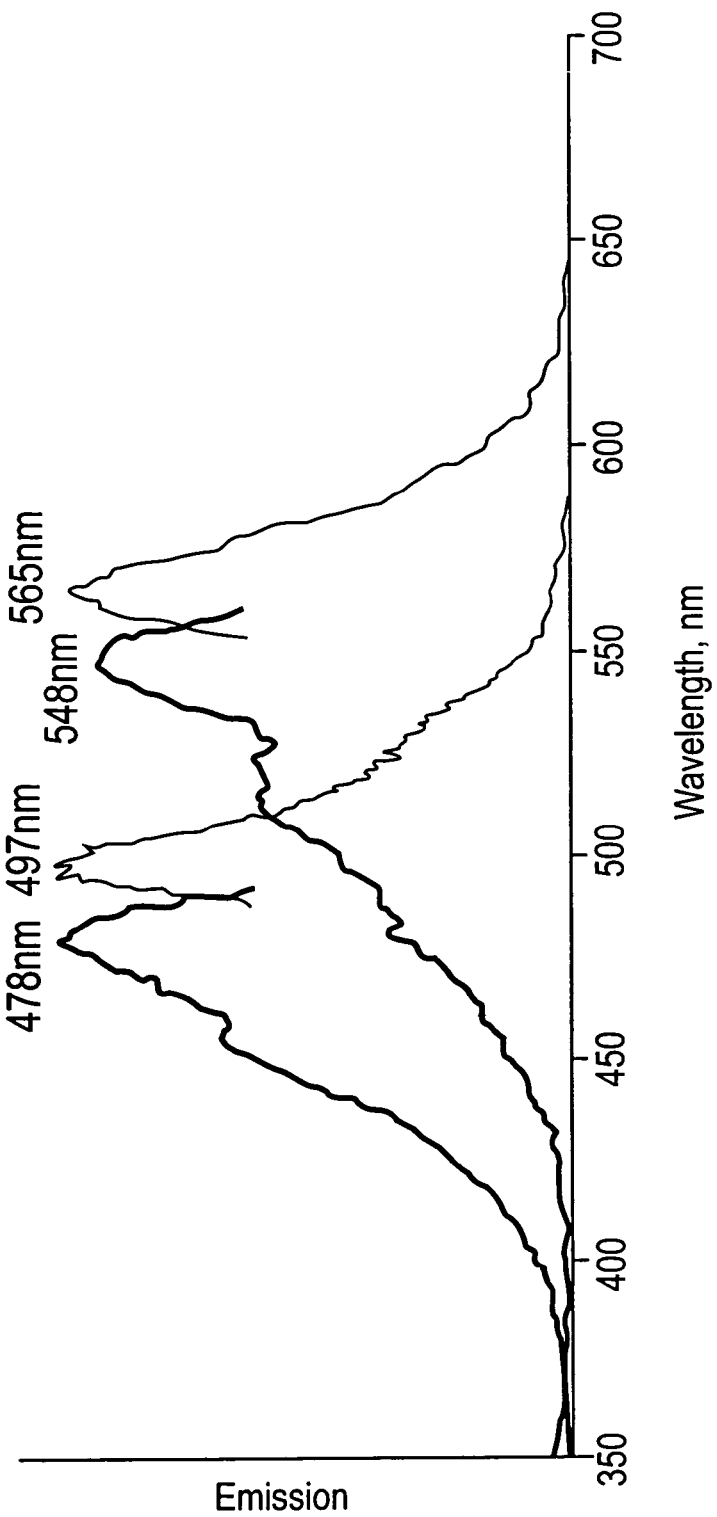
FIG. 2 is a spectrograph of the excitation and emission spectra for the orange fluorescent protein encoded by SEQ ID NO:1 and the OFP generated by the $Tyr^{37}Phe$ and having the primary sequence of SEQ ID NO:22.
Figure 3:
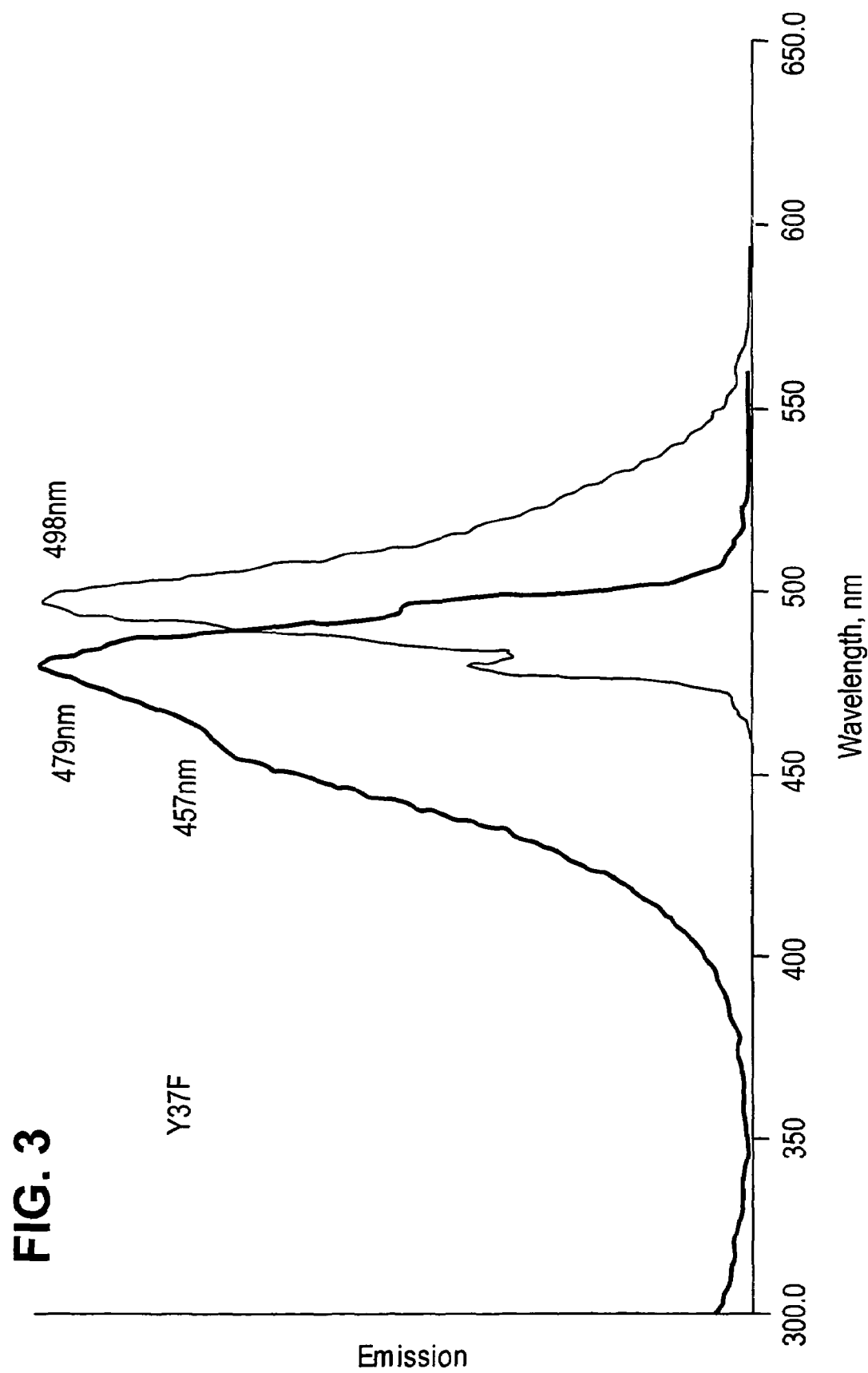
FIG. 3 is a spectrograph of the excitation and emission spectra for the orange fluorescent protein generated by the $Tyr^{37}Phe$ point mutation to the OFP encoded by SEQ ID NO:1, and having the primary sequence of SEQ ID NO:22.

Proteins of the present invention, including fusion molecules comprising proteins of the invention covalently linked to heterologous molecules, such as carbohydrates, nucleic acids, lipids, and other proteins, can be readily detected both in vitro and in vivo using fluorospectroscopic and fluoromicroscopic techniques common in the art. For example, the fluorescence of cells transformed or transfected with a DNA construct of the invention may suitably be measured in a spectrometer where the spectral properties of the cells in liquid culture may be determined as scans of light excitation and emission. Alternatively, such cells grown on nitrocellulose filters placed on plates containing solid media may be illuminated with a scanning polychromatic light source and imaged with an integrating color camera. The color of the emitted light may then be determined by image analysis using specialized software. Exemplary excitation and emission spectra for the OFP purified from *Cerianthus* sp., and the Tyr$^{37}$Phe of the wild-type protein, are depicted in FIG. 2. The spectral data was collected using a Perkin Elmer LS50B Luminescence Spectrometer and analyzed with FL WinLab 4.0™ software.

When a fluorophore, such as an OFP, is exposed to a light of appropriate wavelength, it will absorb photon energy of given wavelength(s) from the light and later release the stored energy in the form of photons of longer wavelength. The range of wavelengths that a fluorophore is capable of absorbing is the excitation spectrum and the range of wavelengths of light that a fluorophore is capable of emitting is the emission or fluorescence spectrum. The excitation and fluorescence spectra for a given fluorophore usually differ and may be readily measured using known instruments and methods. For example, scintillation counters and photometers (e.g. luminometers), photographic film, and solid-state devices such as charge-coupled devices, may be used to detect and measure the emission of light.

The nucleic acids, vectors, mutant proteins provided herein, in combination with well-known techniques for over-expressing recombinant proteins, make it possible to obtain unlimited supplies of homogeneous OFPs. These OFPs have enhanced and/or different fluorescent properties from those of other currently employed tracers in existing diagnostic and assay systems. Such currently employed tracers include radioactive atoms or molecules, other fluorescent markers, including other SFP proteins, and color-producing enzymes such as horseradish peroxidase.

The benefits of using OFPs of the present invention are at least four-fold: OFPs are safer than radioactive-based assays, OFPs can be assayed quickly and easily, and large numbers of samples can be handled simultaneously, reducing overall handling and increasing efficiency. Of great significance, the expression and sub-cellular distribution of OFPs within cells can be detected in living tissues without any other experimental manipulation other than placing the cells on a slide and viewing them through a fluorescence microscope. This represents a significant improvement over, for example, methods of detection that require fixation and subsequent labeling.

The OFPs of the present invention can be used in standard assays involving a fluorescent marker. For example, ligand-ligator binding pairs that can be modified with the proteins of the present invention without disrupting the ability of each to bind to the other can form the basis of an assay encompassed by the present invention. These and other assays are known in the art and their use with OFPs of the present invention will become obvious to one skilled in the art in light of the teachings disclosed herein. Examples of such assays include competitive assays wherein labeled and unlabeled ligands competitively bind to a ligator, noncompetitive assay where a ligand is captured by a ligator and either measured directly or "sandwiched" with a secondary ligator that is labeled. Still other types of assays include immunoassays, single-step homogeneous assays, multiple-step heterogeneous assays, and enzyme assays.

Methods of performing assays on fluorescent materials are well-known in the art and are described in, e.g., Lakowicz, J. R., *Principles of Fluorescence Spectroscopy*, New York:Plenum Press (1983); Herman, B., *Resonance energy transfer microscopy*, in: *Fluorescence Microscopy of Living Cells in Culture, Part B, Methods in Cell Biology*, vol. 30, ed. Taylor, D. L. & Wang, Y.-L., San Diego: Academic Press (1989), pp. 219-243; Turro, N.J., *Modern Molecular Photochemistry*, Menlo Park: Benjamin/Cummings Publishing Col, Inc. (1978), pp. 296-361.

C. N-terminal Sequencing of Proteins

The N-terminal sequence of a purified protein can be obtained by sequential Edman degradation of the protein, followed by HPLC analysis of the degradation product. (see Stone, K. L., Lapresti, M. B., Williams, N. D., Crawford, J. M., DeAngelis, R., and Williams, K. R. (1989) in *Techniques in Protein Chemistry* (Ed. T. Hugli) Academic Press, New York). The analysis can be performed on very small quantities of protein that is either placed on special filter discs, or bound the PVDF membranes (see e.g., Matsudaira, P., *J. Biol. Chem.*, 262:10035-10038 (1987)). The process is routinely automated, providing results from several cycles of Edman degradation in a matter of hours.

The amino acid sequence obtained has a variety of uses including construction of peptides for antibody production and immunogenic analysis. The sequence can also be reverse-translated to provide nucleotide sequences that can be used, for example, in the construction of primers and probes for the isolation and characterization of nucleic acids encoding the protein. By way of example, advantage of this latter use provided the N-terminal amino acid sequence of SEQ ID NO:3. This amino acid sequence was reverse translated and the result used as the basis for the construction of the eight guessmers, SEQ ID NOS:4 to 11. The guessmers were in turn used as part of a 3' RACE protocol to isolate the nucleic acid of SEQ ID NO:1 from a cDNA library of a tube anemone (*Cerianthus* sp).

The Edman degradation cycle used in N-terminal sequencing of a purified protein is identical to that used for sequencing reactions of smaller, internal proteins. The difference in the techniques is in the manner in which the samples are prepared, not in the manner that they are sequenced. An Edman cycle involves reacting phenylisothiocyanate (PITC) with the amino acid residue at the amino terminus under basic conditions (provided by n-methylpiperidine/methanol/water) to form a phenylthiocarbamyl derivative (PTC-protein). Trifluoroacetic acid then cleaves off the first amino acid as its anilinothialinone derivative (ATZ-amino acid) and leaves the new amino terminus for the next degradation cycle. The ATZ amino acid is then removed by extraction with N-butyl chloride and converted to a phenylthiohydantoin derivative (PTH-amino acid) with 25% TFA/water. The PTH-amino acid is transferred to a reverse-phase C-18 column for detection at 270 nm. A standard mixture of 19 PTH-amino acids is also injected onto the column for separation (usually as the first cycle of the sequencing run). This chromatogram provides standard retention times of the amino acids for comparison with each Edman degradation cycle chromatogram. The HPLC chromatograms are collected using a computer data analysis system. To determine the amino acid present at a particular residue number, the chromatogram from the residues of interest is compared with the chromatogram from the previous residue by overlaying one on top of the other. From this, the amino acid for the particular residue can be determined. This process is repeated sequentially to provide the N-terminal sequence of the protein/peptide.

VI. Immunological Detection of OFPs

OFP and fragments thereof, can be used as an immunogen for the production of antisera or antibodies specific for the protein. The purified protein can be used to screen monoclonal antibodies or antigen-binding fragments prepared by immunization with any of the possible forms of pure and impure preparations containing OFP. Recombinant protein is the preferred immunogen for the production of monoclonal or polyclonal antibodies. Alternatively, a synthetic peptide derived from the sequences disclosed herein and conjugated to a carrier protein can be used an immunogen.

Recombinant immunoglobulins may also be produced, see Cabilly, U.S. Pat. No. 4,816,567. These patents are incorporated herein by reference. The polypeptides and antibodies of the present invention may be used with or without modification, including chimeric or humanized antibodies. Immunoassays can be used to qualitatively or quantitatively in the analysis of OFP. A general overview of the applicable technology can be found in Harlow & Lane, *Antibodies: A Laboratory Manual* (1988).

A. Antibodies to OFPs

Methods of producing polyclonal and monoclonal antibodies that react specifically with OFPs, or OFP fragments, are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature*, 256:495-497 (1975). Such techniques include antibody preparation by selection of antibodies from libraries of recombinant antibodies in phage or similar vectors, as well as preparation of polyclonal and monoclonal antibodies by immunizing mammals (see, e.g., Huse et al., *Science*, 246: 1275-1281 (1989); Ward et al., *Nature*, 341:544-546 (1989)).

Antibodies can be raised against folded or denatured OFP, the difference being that antibodies to folded OFP are more likely to recognize epitopes which are only present in the folded protein. Antibodies, including binding fragments and single chain versions, against predetermined fragments of OFP can also be raised by immunization of animals with conjugates of the fragments with immunogenic proteins by methods known in the art.

Monoclonal Antibodies

Monoclonal antibodies can be prepared from various mammalian hosts, such as rodents, cows, sheep, goats, donkeys, primates, humans, etc. Description of techniques for preparing such monoclonal antibodies may be found in, e.g., Stites, et al. (eds.) *Basic and Clinical Immunology* ($4^{th}$ ed.), Lange Medical Publications, Los Altos, Calif., and references cited therein; Harlow and Lane (1988) *Antibodies: A Laboratory Manual*, CSH Press; Goding (1986) *Monoclonal Antibodies: Principles and Practice* ($2^{nd}$ ed.) Academic Press, New York; and particularly in Kohler & Milstein, *Eur. J. Immunol.*, 6:511-519 (1976).

Techniques involving in vitro exposure of lymphocytes to the antigenic polypeptides or alternatively to selection of libraries of antibodies in phage or similar vectors are described in Huse, et al., *Science*, 246:1275-1281 (1989); and Ward et al., *Nature*, 341:544-546 (1989), each of which is hereby incorporated herein by reference.

Monoclonal antibodies and polyclonal sera are tested for specificity by titering against the immunogen protein in an immunoassay, for example, a solid phase immunoassay with the immunogen immobilized on a solid support. Typically, polyclonal antisera with a titer of $10^4$ or greater are selected and tested for their cross reactivity against non-OFPs using a competitive binding immunoassay. Specific polyclonal antisera and monoclonal antibodies will usually bind with a $K_a$ of at least about 1 mM, more usually at least about 300 µM, preferably at least about 3 µM or better, and most preferably, 0.03 µM or better. Antibodies specific only for a particular OFP orthologs, such as *Cerianthus* sp. OFP, can also be made, by subtracting out other cross-reacting orthologs from another species, such as *Aequorea victoria*. Exemplary binding assays are described in more detail below.

Antibody titers of ascites or hybridoma culture fluids are determined by various serological or immunological assays which include, but are not limited to, precipitation, passive agglutination, enzyme-linked immunosorbent assay (ELISA) technique and radioimmunoassay (RIA) techniques. Similar assays are used to detect the presence of OFP in culture media or tissue and cell extracts.

Polyclonal Antibodies

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the protein. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Once the specific antibodies against an OFP are available, the OFP can be detected by a variety of immunoassay methods. For a review of immunological and immunoassay procedures, see *Basic and Clinical Immunology* (Stites & Terr eds., 7$^{th}$ ed., 1991). Moreover, the immunoassays of the present invention can be performed in any of several configurations, which are reviewed extensively in *Enzyme Immunoassay* (Maggio, ed., 1980); and Harlow & Lane, supra.

B. Immunological Binding Assays

OFP polypeptides of the invention can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7$^{th}$ ed. 1991). Immunological binding assays (or immunoassays) typically use an antibody that specifically binds to a protein or antigen of choice (in this case OFP or an antigenic subsequence thereof). The antibody (e.g., anti-OFP) may be produced by any of a number of means well-known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled OFP polypeptide or a labeled anti-OFP antibody. Alternatively, the labeling agent may be a third moiety, such a secondary antibody, which specifically binds to the antibody/OFP complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.*, 111:1401-1406 (1973); Akerstrom et al., *J. Immunol.*, 135:2589-2542 (1985)). The labeling agent can be modified with a detectable moiety, such as biotin, to which another molecule can specifically bind, such as streptavidin. A variety of detectable moieties are well-known to those skilled in the art.

Throughout the assays, incubation and/or washing steps may be required after each combination of reagents. Incubation steps can vary from about 5 seconds to several hours, preferably from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-competitive Assay Formats

Immunoassays for detecting OFP in samples may be either competitive or non-competitive. Non-competitive immunoassays are assays in which the amount of antigen is directly measured. In one preferred "sandwich" assay, for example, the anti-OFP subunit antibodies can be bound directly to a solid substrate on which they are immobilized. These immobilized antibodies then capture OFP present in the test sample. OFPs are thus immobilized and then bound by a labeling agent, such as a second OFP antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of OFP present in the sample is measured indirectly by measuring the amount of known, added (exogenous) OFP displaced (competed away) from an anti-OFP antibody by the unknown OFP present in a sample. In one competitive assay, a known amount of OFP is added to a sample and the sample is then contacted with an antibody that specifically binds to OFP. The amount of exogenous OFP bound to the antibody is inversely proportional to the concentration of the OFP present in the sample. In a particularly preferred embodiment, the antibody is immobilized on a solid substrate. The amount of OFP bound to the antibody may be determined either by measuring the amount of OFP present in an OFP/antibody complex, or alternatively by measuring the amount of remaining uncomplexed protein. The amount of OFP may be detected by providing a labeled OFP molecule.

A hapten inhibition assay is another preferred competitive assay. In this assay the known OFP is immobilized on a solid substrate. A known amount of anti-OFP antibody is added to the sample, and the sample is then contacted with the immobilized OFP. The amount of anti-OFP antibody bound to the known immobilized OFP is inversely proportional to the amount of OFP present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-reactivity Determinations

Immunoassays in the competitive binding format can also be used for cross-reactivity determinations for OFP. For example, a OFP protein at least partially corresponding to an amino acid sequence of SEQ ID NO:2 or an immunogenic region thereof can be immobilized to a solid support. Other proteins, such as other OFPs, are added to the assay so as to compete for binding of the antisera to the immobilized antigen. The ability of the added proteins to compete for binding of the antisera to the immobilized protein is compared to the ability of OFP or immunogenic portion thereof to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs. Antibodies that specifically bind only to particular orthologs of OFP, such as the OFP from *Cerianthus* sp., can also be made using this methodology.

The immunoabsorbed and pooled antisera are then used in a competitive binding immunoassay as described above to compare a second protein, thought to be perhaps an allele, ortholog, or polymorphic variant of OFP, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by OFP that is required to inhibit 50% of binding, then the second protein is said to specifically bind to the polyclonal antibodies generated to the respective OFP immunogen. Therefore, by definition, a protein that specifically binds to antibodies generated to an OFP is an allele, ortholog, or polymorphic variant of OFP and a member of the genus of OFP proteins comprising the present invention.

Other Assay Formats

Western blot (immunoblot) analysis is used to detect and quantify the presence of OFP in the sample. The technique generally comprises separating sample proteins by gel electrophoresis on the basis of molecular weight, transferring the separated proteins to a suitable solid support, (such as a PVDF membrane, a nitrocellulose filter, a nylon filter, or derivatized nylon filter), and incubating the sample with the antibodies that specifically bind OFP. The anti-OFP antibodies specifically bind to OFP on the solid support. These antibodies may be directly labeled or alternatively may be subsequently detected using labeled antibodies (e.g., labeled sheep anti-mouse antibodies) that specifically bind to the anti-OFP antibodies.

Reduction of Non-specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well-known to those of skill in the art. Typically, this technique involves coating the substrate with a proteinaceous composition. In particular, protein compositions such as bovine serum albumin (BSA), non-fat powdered milk, and gelatin are widely used with powdered milk being most preferred.

VII. Fusion Constructs

A particularly useful application of the OFPs of the present invention is their use as molecular markers or "tags". By covalently linking or "fusing" OFP to other molecules, including but not limited to lipids, nucleic acids, polysaccharides, proteins and synthetic polymers, one can easily track the location (and often the concentration) of the tagged molecule using fluorometric techniques previously described. Properly tagged molecules can often be tracked in living organisms, adding a dynamic to the study of cellular processes unattainable prior to the discovery of SFP's. Moreover, the present invention encompasses the fusion of PEST sequences to OFP, thereby decreasing the half-life of the OFP and any molecule tagged with the OFP-PEST marker. Modification of the half-life of an OFP tag facilitates the study of dynamic cellular processes by preventing the build up of tagged fluorescent end-products of the process being studied.

The DNA sequence encoding the fluorescent protein of the invention may be preceded by a signal sequence and optionally a leader sequence, e.g. as described above. Further examples of suitable yeast cells are strains of Kluyveromyces, such as K. lactis, Hansenula, e.g. H. polymorpha, or Pichia, e.g. P. pastoris (cf. Gleeson et al., J. Gen. Microbiol., 132:3459-3465 (1986); U.S. Pat. No. 4,882,279).

Linking agents can be either zero length (directly fuses two molecules together without the introduction of extrinsic material) or can create "spacers" of variable lengths that allow greater separation between the fused molecules. In designing a linking agent, it is important to consider both desired internal and external characteristics. Internally, it is important to choose molecules and binding groups that work well together, ones that do not interact with each other in order to lessen desired functionality. In addition, it is important to maintain an appropriate distance between the fused components so that they are able to operate simultaneously. For example, a carbon chain linker could be incorporated between the two regions (such as (N-substituted) maleimide —$(CH_2)_6$-$His_6$), in order to allow a His-tag to be sufficiently far from the target molecule such that binding of the linking agent to a target molecule does not sterically interfere with the ability of the tag to bind to a nickel column. Desirable external characteristics include selecting a binding group that will bind with a desired specificity to the target macromolecule. In some cases, it might be desirable to create a linking agent that will bind reversibly to a target protein. For example, the use of a linking agent that forms reversible fusions, such as disulfide bonds between cysteines that could be reversed by a reducing agent such as DTT. Such linking agents include those capable of forming disulfide (—S—S—), glycol (—CH(OH) —CH(OH)—), azo (—N=N—), sulfone (—S(=$O_2$)—), or ester (—C(=O)—O—) bridges.

Binding groups reactive with proteins and other polymers are well-known in the literature concerned with creating bifunctional molecules that will act as cross-linking agents. For example, Wong provides a wealth of information on designing and selecting appropriate molecules (see Wong, *Chemistry of Protein Conjugation and Cross-Linking*, CRC Press, 1991 and references therein). An appropriate choice is typically a binding group that reacts relatively non-specifically with the target molecule, but does not react with any component of itself (a binding group that reacts with histidine side chains, for example, would not typically be considered a good choice when using a His-tag, though such a reaction could produce very strong signals akin to the self-reactions in the ubiquitination pathway). Commonly used agents suitable for use as binding groups include aryl halides (which react with histidine side chains), N-maleimide derivatives (react with —SH and —$NH_2$), mercurials (react with —SH), disulfides (react with —SH), acid anhydrides (react with —$NH_2$ and phenols), isocyanates (react with —$NH_2$), isothiocyanates (react with —$NH_2$), sulfonyl halides (react with —$NH_2$), imidoesters (react with —$NH_2$), diazoacetates (react with —COOH and —SH) and dicarbonyl compounds (react with —NH—C(NH)—$NH_2$). Appropriate reactions conditions for using these binding groups are well-known to those of ordinary skill in the art.

Linking agents can also be homo- or heterobifunctional, depending upon whether the reactive binding groups are the same or different. Among the homo-bifunctional coupling agents, there may be mentioned DITC (1,4-phenylene diisothiocyanate), DSS (disuccinimidyl suberate) or the like. Among the hetero-bifunctional coupling agents are SMCC (succinimidyl-4-(N-maleimidomethyl)cyclohexane-1-carboxylate), or SMPB (succinimidyl-4-(p-maleimidophenyl) butyrate) which are capable of reacting, on the one hand, with a primary amine and, on the other hand, with a thiol. A vast majority of the hetero-bifunctional cross-linking agents contains a primary amine-reactive group and a thiol-reactive group. A novel hetero-bifunctional linker for formyl to thiol coupling was disclosed by Heindel et al., *Bioconjugate Chem.*, 2:427-430 (1991).

After coupling the ligand with the copolymer, the possible excess reactive functional groups of the copolymer are neutralized by methods known in the art. For example, the aldehyde groups in excess can be neutralized with a primary amine such as ethanolamine, the maleimide or haloalkyl groups can be neutralized with a thiol (such as thioethanolamine or dithiothreitol), and so on.

Linking agents particularly useful for fusing proteins are those that induce condensation of carboxy and primary amino groups to form an amide bond, such as carbodiimides, ethylchloroformate, Woodward's reagent K1, carbonyldiimidazole, etc.

Polysaccharides can be made reactive through chemical or enzymatic oxidation of oligosaccharides to form aldehyde-binding groups. Such binding groups can react with compounds containing, for example, amines hydrazines, hydrazides, or semicarbazides. Carbohydrate-directed hetero-bifunctional cross-linking agents are, for example, disclosed U.S. Pat. No. 5,329,029.

If the nucleic acid sequence encoding a protein has been isolated, then the protein can be tagged indirectly through recombinant genetic techniques. For example, a PEST sequence can be ligated in frame to the 5' end of the coding sequence of an OFP. Subsequent expression of the fused nucleotide, by methods described above, results in the production of a recombinant OFP-PEST protein with a shortened half-life when expressed intracellularly compared to that of the wild-type OFP. The process can be taken a step further by fusing in frame with the OFP coding sequence, a nucleic acid encoding a target protein. Subsequent expression of this heterologous construct results in a fluorescently-tagged target protein, where the tag (OFP) and possibly the entire recombinant protein has a shortened half-life. Using recombinant DNA technology, the proteins may be fused with no intervening extrinsic linker peptide, or the proteins may be fused through an intervening "spacer" peptide of any length. Spacers are incorporated simply by inserting a nucleic acid encoding the desired spacer between, and in frame with, the nucleic acids encoding the two proteins to be fused. Production and expression of such DNA constructs may be performed using techniques common in the art and discussed above.

Recombinant DNA techniques are the method of choice for introducing PEST sequences into OFP. PEST sequences are polypeptide sequences enriched in Proline (P), glutamic acid (E), serine (S) and threonine (T), and target proteins for rapid destruction. Scientific research has provided strong evidence that PEST sequences do, in fact, serve as proteolytic signals. See for example, Rogers et al., *Science* 234:364-368 (1986); Rechsteiner et al., *TIBS*, 21:267-271 (1996).

VIII. Diagnostic and Therapeutic Uses

A. General

The engineered fluorescent proteins of this invention are useful as fluorescent markers in the many ways fluorescent markers already are used. This includes, for example, coupling OFPs to antibodies, nucleic acids or other receptors for use in detection assays, such as immunoassays or hybridization assays. Such constructs are particularly useful in applications involving the monitoring of gene expression and protein localization. OFP is ideal for such applications as it is readily detectable, can be detected on irradiation using standard long-wave UV light sources; offers the possibility of real-time detection in vivo; the introduction of a substrate is not required to produce a signal; and its relatively small size (25.2 kDa) and monomeric nature, making protein fusions manageable.

B. Cell Dynamics

OFPs of this invention are useful to track the movement of proteins in cells. For example, a nucleic acid encoding OFP is fused to a nucleic acid molecule encoding the protein of interest in an expression vector. Upon expression inside the cell, the protein of interest can be localized based on fluorescence.

OFP may be used to tag virtually any protein and to follow the location of the protein under different conditions. For example, in following a given protein through meiosis, mitosis, apoptosis or other cellular processes. The location of a given protein can also be determined in response to a number of external stimuli. Such stimuli include different physical conditions, such as increasing or decreasing temperature, and also different chemical environments. By the term "chemical environment", it is meant both natural environments that may be encountered, such as compositions with different levels of salt or serum growth factors and the like, and also compositions to which an effector molecule has been added.

For the study of protein localization, concatenation of OFP and a gene of interest encoding for a cellular protein, and subsequent expression of the resulting fusion protein, results in a fluorescent fusion protein that is localized at the normal intracellular location of the protein encoded by the gene of interest. Identifying the intracellular location of OFP thus identifies the intracellular location of the protein of interest. The use of such fusion proteins yields information on the normal cellular role of the protein encoded by the gene of interest.

C. Fluorescence Resonance Energy Transfer (FRET)

Fluorescent molecules are useful in fluorescence resonance energy transfer ("FRET"). FRET involves a donor molecule and an acceptor molecule. To optimize the efficiency and detectability of FRET between a donor and acceptor molecule, several factors need to be balanced. The emission spectrum of the donor should overlap as much as possible with the excitation spectrum of the acceptor to maximize the overlap integral. Also, the quantum yield of the donor moiety and the extinction coefficient of the acceptor should likewise be as high as possible to maximize $R_O$, the distance at which energy transfer efficiency is 50%. However, the excitation spectra of the donor and acceptor should overlap as little as possible so that a wavelength region can be found at which the donor can be excited efficiently without directly exciting the acceptor. Similarly, the emission spectra of the donor and acceptor should overlap as little as possible so that the two emissions can be clearly distinguished. Preferably, the efficiency of FRET between the donor and acceptor is at least 10%, more preferably at least 50% and even more preferably at least 80%.

Engineered OFP's of the present invention enhance FRET by extending the repertoire of donor and acceptor fluorophores, allowing greater selection of fluorophore pairs in designing FRET studies. Moreover, greater selection of FRET donor/acceptor pairs offers the possibility of tracking multiple events, each associated with a donor/acceptor pair having distinct spectral characteristics from other pairs in the assay.

Uses of OFPs in FRET analysis include detecting the cleavage of a substrate having the donor and acceptor coupled to the substrate on opposite sides of the cleavage site. Upon cleavage of the substrate, the donor/acceptor pair are physically separated, eliminating FRET. Assays involve contacting the substrate with a sample, and determining a qualitative or quantitative change in FRET.

Another example is the use of FRET to detect changes in potential across a membrane. A donor and acceptor are placed on opposite sides of a membrane such that one translates across the membrane in response to a voltage change. This creates a measurable FRET.

D. Cell Labeling

It will be appreciated by one of ordinary skill in the art that cells that have been transfected with exogenous DNA can also be identified without creating a fusion protein. The method relies on the identification of cells that have received and express a plasmid or vector that comprises at least a nucleic acid encoding OFP. Cells can be transfected with such a vector by any of the methods known in the art, as detailed above. In the case of stable transformations, both the initially transformed cell and its progeny will carry and express the gene for OFP, consequently fluorescing when exposed to ultra violet light. The technique is particularly useful in cancer and embryological studies. For example, progenitor cells in early embryos can be stably transformed with a vector comprising a nucleic acid encoding OFP. The progenitor cell and its progeny can then be followed throughout the course of development simply by exposing the cells to ultra violet light. Likewise, metastatic cells can be similarly labeled and tracked. Such tracking would allow scientists to follow, for example, the efficacy of treatment regimes in model systems, as the labeled cells not only provide a means for determining the rate of tumor growth, but also the presence and extent of metastatic growths in a simple and quantitative manner.

E. Fluorescent Activated Cell Sorting (FACS)

Many conventional FACS methods require the use of fluorescent dyes conjugated to purified antibodies. Proteins tagged with a fluorescent label would be preferred over antibodies in FACS applications because cells do not have to be incubated with the fluorescent-tagged reagent and because there is no background due to nonspecific binding of an antibody conjugate. OFP is particularly suitable for use in FACS as fluorescence is stable and species-independent and does not require any substrates or cofactors. Moreover, genes of therapeutic interest often do not produce an easily distinguishable phenotype in cells expressing such a gene. Consequently, such a therapeutic gene is usually inserted into a vector that contains a marker gene. The therapeutic gene and the marker gene are placed in the vector under the control of a cellular or viral promoter, and introduced into mammalian cells of interest; subsequently, the transfected cells (the cells containing the vector) are selected according to the phenotype determined by the marker gene. The use of OFP for selection obviates the need to grow the mammalian cells of interest in the presence of drugs in order to select for the transfected cells. Cells transfected with a vector containing OFP and the gene(s) of therapeutic interest are recognized by their fluorescence following excitation, and are sorted by FACS.

In another application, OFP is used to select specific cell lines in which expression vectors that have integrated at a chromosomal location giving very high expression of OFP and of a second gene. An OFP expression vector is transfected into mammalian cells along with a vector expressing a gene of interest. The two vectors become integrated into the chromosome together, and selection of brightly fluorescing cells will yield the cells with high levels of expression of the gene of interest.

F. Inducible Promoters

The engineered OFPs of this invention are useful in systems to detect induction of transcription. In certain embodiments, a nucleotide sequence encoding the engineered OFP is fused to expression control sequences of interest and the expression vector is transfected into a cell. Induction of the promoter can be measured by detecting the expression and/or quantity of fluorescence. Such constructs can be used to follow signaling pathways from receptor to promoter.

OFP can also be used to select bacterial promoters that are induced in response to a specific stimulus. Such an application allows for the systematic scanning of chromosomes of pathogenic and/or commercially important organisms for genes that are regulated in response to environmental stimuli such as iron starvation, transient stress, and antimicrobial agents.

Nucleic acids encoding OFP also provide another dimension to the analysis of promoters in mammalian cells. A range of promoters can be tested for their suitability for use with a given gene, cell, or system. This applies to in vitro uses, such as in identifying a suitable promoter for use in recombinant expression and high-level protein production, and also in in vivo uses, such as in pre-clinical testing or in gene therapy in human subjects.

The testing and ultimate use of inducible and tissue-specific promoters forms another aspect of this invention. In recombinant expression for the purposes of protein production, it may be desired to induce expression at a particular stage of the cell culture or cell cycle, or in a particular cell type. In analyzing the distribution of a given protein within a cell or a given system, it is useful to use a promoter that is only switched on under certain conditions, such as in the presence of certain cytokines or hormones.

In screening embodiments, nucleic acids encoding OFP will be positioned downstream of a promoter that is known to be inducible by the agent that one wishes to identify. Expression of OFP in the cells will normally be silent, and will be switched on by exposing the cell to a composition that contains the selected agent. In using a promoter that is responsive to, for example, a heavy metal, a toxin, a hormone, a cytokine or other defined molecule, the presence of a heavy metal, toxin, hormone, cytokine or such like can readily be determined.

Standard biological applications of OFP should not be overlooked. For example, its use as a molecular weight marker on protein gels and Western blots, in calibration of fluorometers and FACS machines and in microinjection into cells and tissues.

IX. Kits

Expression kits comprising nucleic acids encoding OFPs form another aspect of the invention. Such kits will generally contain, in suitable container means, a formulation of a nucleic acid encoding an OFP or a vector capable of expressing such a nucleic acid, and instructions for using the same.

When the components of the kit are provided in one or more liquid solutions, the liquid solution is an aqueous solution, with a sterile aqueous solution being particularly preferred. The OFP gene or vector may also be formulated into a syringeable composition. If such is the case, the container means may itself be a syringe, pipette, eye dropper, or other such like apparatus, from which the formulation may be applied to a cell, or to an area of the body, or injected into an animal, or applied to and mixed with other components of a kit.

Components of the kit may be provided as dried powder(s). When reagents or components are provided as a dry powder, the powder can be reconstituted by the addition of a suitable solvent. It is envisioned that the solvent may also be provided in another container means.

The container means will generally include at least one vial, test tube, flask, bottle, syringe or other container means, into which the OFP gene or vector may be suitably allocated. A second engineered nucleic acid encoding OFP or vector construct may also be provided, wherein the kit will also generally contain a second vial or other container into which this is placed. The kits may also comprise a second/third container means for containing a sterile, pharmaceutically acceptable buffer or other diluent.

Kits of the present invention will also typically include a means for containing the vials in close confinement for commercial sale, such as, e.g., injection or blow-molded plastic containers into which the desired vials are retained.

Irrespective of the number or type of containers, the kits of the invention may also comprise, or be packaged with, one or more further molecular biological reagents, such as restriction enzymes.

EXAMPLES

Example 1

Expression and Purification of OFP from *E. coli*

This example provides an exemplary procedure for expressing OFP protein in *E. coli*, and purifying the expressed protein from the *E. coli* expression host.

An isolated nucleic acid encoding (OFP) was sub-cloned in frame into the Invitrogen pRSET expression vector, incorporating 6 N-terminal histidine residues into the protein sequence and placing expression of OFP under control of isopropyl β-D-thiogalactoside (IPTG) induction. The recombinant plasmid was transformed into *E. coli* TOP 10, and recombinant clones selected by incubating at 37° C. overnight on standard 1.5% agar plates containing LB medium and ampicillin (100 µg/mL). Positive clones were identified by the colony PCR method (see Gussow et al., *Nucleic Acids Res.*, 17:4000 (1989)) and grown in 3 mL LB-medium (supplemented with 100 µg/mL ampicillin).

Recombinant plasmid was purified by conventional plasmid purification methods and transformed into bacterial expression host BL21 Star™ (DE3) pLysS (Invitrogen, San Diego, Calif.). Transformed BL21 Star™ (DE3) pLysS cells were growth in 5 mL ampicillin (100 µg/mL)/chloramphenicol (34 µg/mL)-containing LB medium at 37° C. overnight. The overnight culture was then transferred to 1L fresh ampicillin (100 µg/mL)/chloramphenicol (34 µg/mL)-containing LB medium and grown to $OD_{600}$=0.6 by incubating at 37° C. on a rotary platform (240 rpm).

Induction of the liquid cultures was performed by adding IPTG to a final concentration of 1 mM and continued incubation for 3 hrs at 37° C. with good oxygen supply (5 L/min air flow). Cells expressing OFP were harvested by centrifugation, washed in PBS pH 7.4, resuspended in 50 mM TRIS® (hydroxymethyl) aminomethane hydrochloride pH 8.0, 300 mM NaCl, and then lysed by passage through a French Press at 10,000 psi. Lysates were clarified by centrifugation at 20 K rpm for 45 min, and the supernatant fraction applied to a Novagen His-bind resin.

Columns containing a Novagen His-bind resin were loaded with 100 µL soluble extract (in 50 mM TRIS® (hydroxymethyl) aminomethane hydrochloride pH 8.0, 300 mM NaCl), washed with 10 bed volumes of the same buffer and with 10 volumes of the buffer containing 20 mM imidazole. The recombinant proteins were then eluted with the same buffer containing 100 mM imidazole. Orange fractions were pooled and subjected to enterokinase (SIGMA, St. Louis, Mo.) proteolysis (1:50 w/w) for 22 hrs at RT. After addition of 0.5 mM PMSF, the digest was reapplied to the Ni column to remove proteins retaining the N-terminal His-tag.

Example 2

Fluoroscopic Analysis of OFP's

This example illustrates both in situ and in vitro assays that may be used to determine the spectral properties of the OFPs provided by the invention.

Excitation spectra are obtained by collecting emission at peak wavelengths and are corrected by a Rhodamine B quantum counter. Emission spectra are likewise measured at the excitation peaks and are corrected using factors from the fluorometer manufacturer (Spex Industries, Edison, N.J.). For measuring molar extinction coefficients, 20 to 30 µg of protein are used in 1 mL of PBS pH 7.4. Quantum yields of OFP's are estimated by comparison with fluorescein in 0.1 N NaOH as a standard of quantum yield 0.91 [ed. Miller, J. N., *Standards in Fluorescence Spectrometry* (Chapman and Hall, New York, 1981)]. Excitation and emission spectra are measured with 1.8 nm bandwidths and the non-scanning wavelength set to the appropriate peak.

OFPs can be assayed in situ, after expression in a suitable host, or may be purified and the fluorescence characteristics of the isolated protein determined.

In Situ Assay

Cells are cultured on top of cover slips to allow observation under a fluorescence microscope. After transfection with a vector containing the OFP coding sequence, the cells are incubated at 37° C. for 24 hours on the cover slips and then fixed with 4% paraformaldehyde for 30 minutes. The cover slips are mounted on a glass slide for fluorescence examination with a Zeiss Axioskop Model 50 fluorescent microscope. To determine protein turnover, the cells are treated with cycloheximide at a final concentration of 100 µg/mL for variable times before paraformaldehyde fixation.

For FACS analysis, the transfected cells as well as cycloheximide-treated cells are collected by EDTA treatment and the cell pellets resuspended in 0.5 mL of PBS. The cell suspensions are analyzed for fluorescence intensity by FACS Calibur (Becton Dickson, Inc., San Jose, Calif.). OFP is excited at 548 nm, and emission is detected at 565 nm using a 550/20 bandpass filter.

In Vitro Assay

Recombinant OFP protein is prepared as described in Example 1. An excitation spectrum is obtained by collecting emission at 565 nm and is corrected by a Rhodamine B quantum counter. An emission spectrum is likewise measured at 548 nm and is corrected using factors from the fluorometer manufacturer (Spex Industries, Edison, N.J.). For measuring molar extinction coefficients, 20 to 30 µg of protein (SEQ ID NO:2) is used in 1 mL of PBS pH 7.4.

OFP is excited at 548 nm and emits orange light with a peak at 565 nm. When the bacterial colonies are viewed under an FITC filter set, an orange fluorescence light is detected and upon examination with a rhodamine filter set, a bright red fluorescence is seen.

Example 3

Isolation of Nucleic Acids Encoding OFPs from a cDNA Library

Example 3 provides exemplary methods for identifying and isolating nucleic acids encoding OFPs from cDNA libraries.

A cDNA library is constructed in, for example, the λZapII (Stratagene, La Jolla, Calif.) cloning vector. Typically, 1 µg of EcoR I-digested and dephosphorylated vector arms (available from Stratagene) are ligated to 0.1 µg of EcoR I linkered cDNA in a 5 µL ligation using about 3 Weiss units T4 DNA ligase (New England Biolabs) in 50 mM TRIS® (hydroxymethyl) aminomethane hydrochloride (pH 7.6), 7 mM MgCl$_2$, 1 mM DTT, 5% PEG8000 and 1 mM ATP. Ligations are carried out at 16° C. overnight. Ligations are packaged in GigapackII Gold packaging extracts (available from Stratagene) according to the protocol provided by the vendor. Libraries are plated for titering and screening on the E. coli XL1-Blue host also available from Stratagene.

Plaque forming units are then plated out on 150 mm diameter, Petri plates. Duplicate nitrocellulose filter lifts are prepared from these plates after the procedures described by Mandates et al. The filters are hybridized to $^{32}$P-labeled oligonucleotide probes:

```
OFP-T58 forward primer
5'-ACGGCATTTCAGTATGGTTTCCGCGTA-3'    SEQ ID NO:14

OFP-M131 reverse primer
5'-CATCACTGGCCCATTCGGCGGGAAGTT-3'    SEQ ID NO:15
```

Hybridization reactions are carried out in 6×SSPE, 0.1% SDS, 0.1 mg/mL tRNA (SIGMA, St. Louis, Mo.), and 2× Denhardt's (0.4 mg/mL each: ficoll, polyvinylpyrrolidine, BSA fraction V) reagent, at 50° C. overnight (about 16 hrs). The hybridization solution contains 2-3×10$^6$ cpm of labeled oligo per ml of solution. Following hybridization, filters are washed twice at room temperature in 2×SSPE, 0.1% SDS and twice in the same solution pre-heated to 50° C. The filters are allowed to air dry and are then exposed to film for 7 days at −70° C. using intensifying screens.

The developed films are examined to identify plaques that hybridize to the screening oligonucleotide. Areas of the library plates corresponding to positive signals are excised, resuspended and replated for a second round of screening via the hybridization procedure detailed above. Positive signals from this second screening are plaque-purified through 1 or 2 additional rounds of hybridization. Positive clones from the final round of hybridization are analyzed by DNA sequencing to determine if they contain DNA sequences that encode an OFP.

The phagemid portion of the λZapII phage, which contains the cloned inserts, is referred to as pBluescript SK$^+$. Phagemid pBluescript SK$^+$ is excised from each of the λZapII recombinants that hybridized to the oligonucleotide probe. The procedure for in vivo excision of the recombinant pBluescript SK$^+$ plasmid from the λZapII vector is given in detail by the vendor protocols. Briefly, coinfection of λZapII and an M13 "helper" phage results in packaging of a single-stranded DNA copy of the recombinant pBluescript SK$^+$ within an infectious M13 virion. When such a virion infects a sensitive cell, the single-stranded DNA is converted to a double-stranded DNA and is propagated vertically as a plasmid. The ampicillin resistance gene encoded on pBluescript SK$^+$ affords selection for this event. Thus E. coli XL1-Blue derivatives containing the "rescued" recombinant pBluescript SK$^+$ plasmid from each of the eight positive λZapII clones were readily obtained following the protocols described by Stratagene and employing the "helper" phage provided along with the λZapII vector.

For DNA sequencing, double-stranded plasmid DNA was prepared from six of these recombinant plasmids by a "mini-prep" procedure based on Birnboim and Doily NAR 7:1513-1523 (1979). DNA sequencing reactions using the dideoxy-chain terminating method are performed using these templates and the screening oligo as the primer. Reagents for sequencing are obtained from United States Biochemical as a kit (Sequenase version 2.0) and sequencing procedures were carried out according to the protocols provided by the vendor.

Example 4

Creating an OFP Protein Chromophore by Site-directed Mutagenesis

This example describes site-directed mutagenesis techniques for creating the OFP chromophores of the present invention.

OFPs can be formed by site-directed mutagenesis of the chromophores of existing spontaneously fluorescent proteins as generally described by Schwartz et al., J. Virol., 66:7176 (1992). In addition to changing specific codons, site-directed mutagenesis can also be used to improve protein expression by replacing potential inhibitory nucleotide sequences without altering the amino acid sequence of the protein. This approach has been successfully employed in the past for other proteins (Schwartz et al., op. cit.).

The general protocol for forming such OFP's entails first cloning into a standard ds-DNA plasmid, a nucleic acid that encodes a spontaneously fluorescent protein, under the control of eukaryotic or prokaryotic promoters. The plasmid vector is then converted to a ss-DNA by standard methods (Maniatas et al.). The ss-DNA is annealed to 40-50 nucleotide DNA oligomers having base mismatches at the site(s) intended to be engineered to create the coding sequence for the OFP chromophore. The hybrid DNA is then converted to a closed ds-DNA plasmid vector by use of DNA polymerase and standard protocols. Plasmids containing the desired mutations are next identified by restriction analysis following plasmid DNA isolation from E. coli strains transformed with the mutagenized DNA. The presence, in the correct position, of a region encoding an amino acid pentamer capable of forming an OFP chromophore is verified by PCR and DNA sequencing.

The oligonucleotides used in site-specific engineering of the chromophores are dependent upon the spontaneously fluorescent protein used as starting material. For example, when using wild type GFP from A. victoria, the 40-50 base nucleic acid containing the appropriate mismatches to form the OFP chromophore is derived from the base sequence surrounding the GFP chromophore. The coding sequence for the engineered OFP can be isolated and expressed as described in Example 1. An exemplary oligomer for such a conversion are presented in SEQ ID NO:25 and 26 listed below;

GFP to OFP forward primer
5'-ACACTTGTCACTACTTTCCAGTATGGTTTTCAATGCTTTTCAAGA-3'   SEQ ID NO:25

GFP to OFP reverse primer
5'-TCTTGAAAAGCATTGAAAACCATACTGGAAAGTAGTGACAAGTGT-3'   SEQ ID NO:26

Vectors used to clone and express the OFPs of the present invention are derivatives of commercially available plasmids such as pcDNA$_4$/HisMax (Invitrogen, San Diego, Calif.), pBluescript SK$^+$ (Stratagene, La Jolla, Calif.) and pET11a (Novagen, Madison, Wis.).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Example 5

Modifying the Spectral Properties of an Existing OFP Protein by Site-directed Mutagenesis Example 4 describes how the chromophore of an OFP can be modified by site-directed mutagenesis to create OFPs with novel spectral properties. The present example illustrates that minor structural changes, including single amino acid substitutions, to the OFP can produce new fluorescent proteins with diverse spectral properties.

Using the methodology of the previous example, a series of spectral variants were generated by single amino acid substitution in the primary sequence of an OFP protein of the present invention.

The mutation Tyr$^{37}$Phe may be incorporated into wild-type OFP to generate the protein of SEQ ID NO:22 by amplifying the wild type nucleotide sequence (SEQ ID NO:1) with the following primer pair;

As can be seen from the spectra depicted in FIG. 2, this single amino acid mutation results in a shift in the excitation/emission spectra from the wild type (excitation/emission 548 nm/565 nm) to the mutant (excitation/emission 478 nm/497 nm).

Using the same primer strategy and PCR techniques, other point mutations can be introduced to produce other proteins with useful spectral characteristics. For example, the mutation Cys$^{48}$Ser can be produced, generating the protein of SEQ ID NO:27. As can be seen from the spectra depicted in FIG. 4, this mutant has almost identical spectral properties to the wild type OFP (excitation/emission 548 nm/565 nm), with the exception of slightly weaker absorption at 488 nm. This mutant will not form inter-disulfide bonds and therefore has less tendency towards oligomerization and aggregation than found in the wild type OFP.

Similarly, the mutation Gln$^{61}$ Ser generates the protein of SEQ ID NO:28. As can be seen from the spectra depicted in FIG. 5, this mutation results in a shift in the excitation/emission spectra from wild type OFP (excitation/emission 548 nm/565 nm) to (excitation/emission 535 nm/548 nm).

As another example, the mutation Lys$^{79}$Arg generates the protein of SEQ ID NO:29. As can be seen from the spectra depicted in FIG. 6, this mutation results in a shift in the excitation/emission spectra from wild type OFP (excitation/emission 548 nm/565 nm) to (excitation/emission 548 nm/575 nm).

These results indicate that minor structural changes in the β-can enclosing the OFP chromophore, that are distant in the primary sequence from the chromophore of the protein, can create OFPs having a wide range of spectral characteristics.

It is understood that the examples and embodiments described herein are for illustrative purposes only and that various modifications or changes in light thereof will be suggested to persons skilled in the art and are to be included within the spirit and purview of this application and scope of the appended claims.

To ensure a full description of the invention, all publications and patent applications cited in this specification are herein incorporated by reference as if each individual publication or patent application were specifically and individually indicated to be incorporated by reference.

OFP-Y37F-F, forward primer 5'-CCTTATACAGGTAAATTTTCCATGAAGATGACG-3'   SEQ ID NO:23

OFP-Y37F-R, reverse primer 5'-CGTCATCTTCATGGAAAATTTACCTGTATAAGG-3'   SEQ ID NO:24

| cDNA nucleotide sequence of Cerianthus sp. OFP |
|---|
| ATG<u>AACCTGAGCAAAAACGTGAGCGTGAGCGTGTATATGAAGGGGAACGTCAA</u>    SEQ ID NO:1 |
| <u>CAATCAT</u>GAGTTTGAGTACGACGGGGAAGGTGGTGGTGATCCTTATACAGGTA |
| AATATTCCATGAAGATGACGCTACGTGGTCAAAATTGCCTACCCTTTTCCTAT |
| GATATCATTACCACGGCATTTCAGTATGGTTTCCGCGTATTTACAAAATACCC |
| TGAGGGAATTGTTGACTATTTTAAGGATTCGCTTCCCGACGCATTCCAGTGGA |
| ACAGACGAATTGTGTTTGAAGATGGTGGAGTACTAAACATGAGCAGTGATATC |
| ACATATAAAGATAATGTTCTGCATGGTGACGTCTGGGCTGTCGGAGTGAACTT |
| CCCGCCGAATGGGCCAGTGATGAAGAATGAAATTGTGATGGAGGAACCGACTG |
| AAGAAACATTTACTCCAAAAAACGGGGTTCTTGTTGGCTTTTGTCCCAAAGCG |
| TACTTACTTAAAGATGGTTCCTATTACTATGGAAATATGACAACATTTTACAG |
| ATCCAAGAAATCTGGCCAGGCACCTCCTGGGTATCACTTTGTTAAGCATCGTC |
| TCGTCAAGACCAATGTGGGACATGGATTTAAGACGGTTGAGCAGACTGAATAT |
| GCCACTGCTCATGTCAGTGATCTTCCCAAGTAA*CATAAATAGTTGCAGCCAC |
| TTCTCAATAAATAGTTGGCCACTTTGGTGAGCTGAAAGCCTTTTCAAGTTTTA |
| TTGCACCTTTGTAGTTTTACATTTGTAGCAAAAAGAAGTAAAAACGATTTTTT |
| GTTTGCTGTAACTTCTGCTTTATAACTGGAGTAAACTATTCTTCTGTATACGA |
| AAAAAAAAAAAAAAA |

NOTE:
The ATG start condon is added to replace the first proline condon at the 5'end of the cloned nucleotide sequence of OFP. The underlined nucleotides are back-translated sequences based on protein sequencing data usind E. coli condon preferences. The stop condon is labeled with an asterisk.

| polypeptide sequence of Cerianthus sp. OFP determined from cDNA |
|---|
| <u>MNLSKNVSVSVYMKGNVNNH</u>EFEYDGEGGGDPYTGKYSMKMTLRGQNCLPFSY    SEQ ID NO:2 |
| DIITTAFQYGFRVFTKYPEGIVDYFKDSLPDAFQWNRRIVFEDGGVLNMSSDI |
| TYKDNVLHGDVWAVGVNFPPNGPVMKNEIVMEEPTEETFTPKNGVLVGFCPKA |
| YLLKDGSYYYGNMTTFYRSKKSGQAPPGYHFVKHRLVKTNVGHGFKTVEQTEY |
| ATAHVSDLPK |

Note:
The underlined peptide sequences are based on protein sequencing results. A methionine was added to the N-terminal of the polypeptide to replace the original proline.

```
N-terminal protein sequencing determination of
Cerianthus sp. OFP
PNLSKNVSVSVYH                                              SEQ ID NO:3

OFP-H1 guessmer nucleic acid sequence
5'-ATGAARGGRAAYGTPAACAACC-3'                               SEQ ID NO:4

OFP-H2 guessmer nucleic acid sequence
5'-ATGAARGGRAAYGTPAACAATC-3'                               SEQ ID NO:5

OFP-H3 guessmer nucleic acid sequence
5'-ATGAARGGRAAYGTRAATAACC-3'                               SEQ ID NO:6

OFP-H4 guessmer nucleic acid sequence
5'-ATGAARGGRAAYGTRAATAATC-3'                               SEQ ID NO:7

OFP-H5 guessmer nucleic acid sequence
5'-ATGAARGGRAAYGTYAACAACC-3'                               SEQ ID NO:8

OFP-H6 guessmer nucleic acid sequence
5'-ATGAARGGRAAYGTYAACAATC-3'                               SEQ ID NO:9

OFP-H7 guessmer nucleic acid sequence
5'-ATGAARGGRAAYGTYAATAACC-3'                               SEQ ID NO:10

OFP-H8 guessmer nucleic acid sequence
5'-ATGAARGGRAAYGTYAATAATC-3'                               SEQ ID NO:11

OFP-M13 forward primer
5'-ATGAAGGGGAATGTCAACAATCAT-3'                             SEQ ID NO:12

OFP-STOP reverse primer
5'-TTACTTGGGAAGATCACTGACGAG-3'                             SEQ ID NO:13

OFP-T58 forward primer
5'-ACGGCATTTCAGTATGGTTTCCGCGTA-3'                          SEQ ID NO:14

OFP-M131 reverse primer
5'-CATCACTGGCCCATTCGGCGGGAAGTT-3'                          SEQ ID NO:15

Invitrogen GeneRacer™ Oligo-dT primer
5'-GCTGTCAACGATACGCTACGTAACGGCATGACAGTGT$_{18}$-3'         SEQ ID NO:16

OFP mutant S$^8$T
MNLSKNVTVSVYMKGNVNNHEFEYDGEGGGDPYTGKYSMKMTLRGQNCLPFSY      SEQ ID NO:17

DIITTAFQYGFRVFTKYPEGIVDYFKDSLPDAFQWNRRIVFEDGGVLNMSSDI

TYKDNVLHGDVWAVGVNFPPNGPVMKNEIVMEEPTEETFTPKNGVLVGFCPKA

YLLKDGSYYYGNMTTFYRSKKSGQAPPGYHEVKHRLVKTNVGHGFKTVEQTEY

ATAHVSDLPK

OFP mutant V$^{120}$I
MNLSKNVSVSVYMKGNVNNHEFEYDGEGGGDPYTGKYSMKMTLRGQNCLPFSY      SEQ ID NO:18

DITTTAFQYGFRVFTKYPEGIVDYFKDSLPDAFQWNRRIVFEDGGVLNMSSDI

TYKDNVLHGDVWAIGVNFPPNGPVMKNEIVMEEPTEETFTPKNGVLVGFCPKA

YLLKDGSYYYGNMTTFYRSKKSGQAPPGYHFVKHRLVKTNVGHGFKTVEQTEY

ATAHVSDLPK

OFP mutant A$^{159}$V
MNLSKNVSVSVYMKGNVNNHEFEYDGEGGGDPYTGKYSMKMTLRGQNCLPFSY      SEQ ID NO:19

DIITTAFQYGFRVFTKYPEGIVDYFKDSLPDAFQWNRRTVFEDGGVLNMSSDI

TYKDNVLHGDVWAVGVNFPPNGPVMKNEIVMEEPTEETFTPKNGVLVGFCPKV

YLLKDGSYYYGNMTTFYRSKKSGQAPPGYHFVKHRLVKTNVGHGFKTVEQTEY

ATAHVSDLPK

OFP mutant N$^{171}$Q
MNLSKNVSVSVYMKGNVNNHEFEYDGEGGGDPYTGKYSMKMTLRGQNCLPFSY      SEQ ID NO:20

DIITTAFQYGFRVFTKYPEGIVDYFKDSLPDAFQWNRRIVFEDGGVLNMSSDI
```

-continued

```
TYKDNVLHGDVWAVGVNFPPNGPVMKNEIVMEEPTEETFTPKNGVLVGFCPKA

YLLKDGSYYYGQMTTFYRSKKSGQAPPGYHFVKHRLVKTNVGHGFKTVEQTEY

ATAHVSDLPK

OFP mutant T²¹⁴S
MNLSKNVSVSVYMKGNVNNHEFEYDGEGGGDPYTGKYSMKNTLRGQNCLPFSY    SEQ ID NO:21

DIITTAFQYGFRVFTKYPEGIVDYFKDSLPDAFQWNRRIVFEDGGVLNMSSDI

TYKDNVLHGDVWAVGVNFPPNGPVMKNEIVMEEPTEETFTPKNGVLVGFCPKA

YLLKDGSYYYGNMTTFYRSKKSGQAPPGYHFVKHRLVKTNVGHGFKTVEQTEY

ASAHVSDLPK

OFP green fluorescent mutant Y³⁷F
MNLSKNVSVSVYMKGNVNNHEFEYDGEGGGDPYTGKFSMKNTLRGQNCLPFSY    SEQ ID NO:22

DIITTAFQYGFRVFTKYPEGIVDYFKDSLPDAFQWNRRIVFEDGGVLNMSSDI

TYKDNVLHGDVWAVGVNFPPNGPVNKNEIVMEEPTEETFTPKNGVLVGFCPKA

YLLKDGSYYYGNMTTFYRSKKSGQAPPGYHFVKHRLVKTNVGHGFKTVEQTEY

ATAHVSDLPK

OFP-Y37F-F, Forward primer
5'-CCTTATACAGGTAAATTTTCCATGAAGATGACG-3'                   SEQ ID NO:23

OFP-Y37F-R, Reverse primer
5'-CGTCATCTTCATGGAAAATTTACCTGTATAAGG-3'                   SEQ ID NO:24

GFP to OFP Forward primer
5'-ACACTTGTCACTACTTTCCAGTATGGTTTTCAATGCTTTTCAAGA-3'       SEQ ID NO:25

GFP to OFP Reverse primer
5'-TCTTGAAAAGCATTGAAAACCATACTGGAAAGTAGTGACAAGTGT-3'       SEQ ID NO:26

OFP orange fluorescent mutant C⁴⁸S
MNLSKNVSVSVYMKGNVNNHEFEYDGEGGGDPYTGKYSMKNTLRGQNSLPFSY    SEQ ID NO:27

DIITTAFQYGFRVFTKYPEGIVDYFKDSLPDAFQWNRRIVFEDGGVLNMSSDI

TYKDNVLHGDVWAVGVNFPPNGPVMKNEIVMEEPTEETFTPKNGVLVGFCPKA

YLLKDGSYYYGNMTTFYRSKKSGQAPPGYHFVKHRLVKTNVGHGFKTVEQTEY

ATAHVSDLPK

OFP golden-yellow fluorescent mutant Q⁶¹S
MNLSKNVSVSVYMKGNVNNHEFEYDGEGGGDPYTGKYSMKMTLRGQNCLPFSY    SEQ ID NO:28

DIITTAFSYGFRVFTKYPEGIVDYFKDSLPDAFQWNRRIVFEDGGVLNMSSDI

TYKDNVLHGDVWAVGVNFPPNGPVMKNEIVNEEPTEETFTPKNGVLVGFCPKA

YLLKDGSYYYGNMTTFYRSKKSGQAPPGYHFVKHRLVKTNVGHGFKTVEQTEY

ATAHVSDLPK

OFP magenta fluorescent mutant K⁷⁹R
MNLSKNVSVSVYMKGNVNNHEFEYDGEGGGDPYTGKYSMKNTLRGQNCLPFSY    SEQ ID NO:29

DIITTAFQYGFRVFTKYPEGIVDYFRDSLPDAFQWNRRIVFEDGGVLNSSDI

TYKDNVLHGDVWAVGVNFPPNGPVMKNEIVMEEPTEETFTPKNGVLVGFCPKA

YLLKDGSYYYGNMTTFYRSKKSGQAPPGYHFVKHRLVKTNVGHGFKTVEQTEY

ATAHVSDLPK
```

What is claimed is:

1. An isolated nucleic acid encoding a spontaneously fluorescent protein having a β can structure, the protein consisting of:
   a. an amino acid sequence having 95% or greater sequence identity to the orange fluorescent protein of SEQ ID NO:2;
   b. a sequence segment of SEQ ID NO:34 wherein five contiguous amino acids in the sequence segment are $FR_1R_2R_3F$, where:
   $R_1$ is Q or S,
   $R_2$ is selected from the group consisting of Y, W, F and H,
   $R_3$ is selected from the group consisting of G, A and S; and,
   c. eleven β strands, each β strand having a continuous amino acid sequence of between 7 and 15 amino acids, wherein the eleven β strands form a cylinder within which resides the sequence segment.

2. The isolated nucleic acid of claim 1, wherein the nucleic acid encodes a polypeptide comprising the amino acid sequence of SEQ ID NO:2.

3. The isolated nucleic acid of claim 1, wherein the nucleic acid comprises the nucleotide sequence of SEQ ID NO:1.

4. The isolated nucleic acid of claim 1, further characterized by being able to be PCR amplified by primers selectively hybridizing under stringent hybridization conditions to the same sequence as one of the primer pairs selected from the group consisting of: SEQ ID NOS:12 and 13; and, SEQ ID NOS:14 and 15 where the stringent hybridization conditions are 5×SSC and 1% SDS incubated at 65° C., with a wash in 0.2×SSC and 0.1% SDS at 65° C.

5. The isolated nucleic acid of claim 1, wherein the nucleic acid hybridizes under stringent conditions to the nucleic acid of SEQ ID NO:1 where the stringent hybridization conditions are 5×SSC and 1% SDS incubated at 65° C., with a wash in 0.2×SSC and 0.1% SDS at 65° C.

6. An expression vector comprising:
   a. a nucleotide sequence encoding a spontaneously fluorescent protein having a β can structure, the β can structure consisting of:
      i. an amino acid sequence having 95% or greater sequence identity to the orange fluorescent protein of SEQ ID NO:2;
      ii. a sequence segment of SEQ ID NO:34 wherein five contiguous amino acids in the sequence segment are $FR_1R_2R_3F$, where:
   $R_1$ is Q or S,
   $R_2$ is selected from the group consisting of Y, W, F and H,
   $R_3$ is selected from the group consisting of G, A and S; and,
      iii. eleven β strands, each β strand having a continuous amino acid sequence of between 7 and 15 amino acids, wherein the eleven β strands form a cylinder within which resides the sequence segment; and,
   b. regulatory sequences operably linked to the coding sequence.

7. The expression vector of claim 6, wherein the coding sequence further comprises a nucleotide sequence encoding a second polypeptide, the nucleotide sequence encoding the second polypeptide being in frame with the nucleotide sequence encoding the spontaneously fluorescent protein.

8. A recombinant cell comprising the expression vector of claim 6.

9. A recombinant cell comprising the expression vector of claim 7.

10. The recombinant cell of claim 8, wherein the cell is selected from the group consisting of a bacterium, an insect cell and a mammalian cell.

11. A kit comprising a sealed container having a measured amount of the expression vector of claim 6 and instructions for using the expression vector.

* * * * *

SEQUENCE LISTING

<160> NUMBER OF SEQ ID NOS: 32

<210> SEQ ID NO 1
<211> LENGTH: 864
<212> TYPE: DNA
<213> ORGANISM: Cerianthus sp.
<220> FEATURE:
<223> OTHER INFORMATION: cDNA sequence for orange flourescent protein
      (OFP)

<400> SEQUENCE: 1

```
atgaacctga gcaaaaacgt gagcgtgagc gtgtatatga aggggaacgt caacaatcat      60
gagtttgagt acgacgggga aggtggtggt gatccttata caggtaaaata ttccatgaag    120 atgacgctac gtggtcaaaa ttgcctaccc ttttcctatg atatcattac cacggcattt    180
cagtatggtt ccgcgtatt tacaaaatac cctgagggaa ttgttgacta ttttaaggat      240
tcgcttcccg acgcattcca gtggaacaga cgaattgtgt ttgaagatgg tggagtacta    300
aacatgagca gtgatatcac atataaagat aatgttctgc atggtgacgt ctgggctgtc    360
ggagtgaact tcccgccgaa tgggccagtg atgaagaatg aaattgtgat ggaggaaccg    420
actgaagaaa catttactcc aaaaaacggg gttcttgttg gcttttgtcc caaagcgtac    480
ttacttaaag atggttccta ttactatgga aatatgacaa cattttacag atccaagaaa    540
tctggccagg cacctcctgg gtatcacttt gttaagcatc gtctcgtcaa gaccaatgtg    600
ggacatggat taagacggt tgagcagact gaatatgcca ctgctcatgt cagtgatctt    660
cccaagtaac ataaatagtt gcagccactt ctcaataaat agttggccac tttggtgagc    720
tgaaagcctt ttcaagtttt attgcacctt tgtagtttta catttgtagc aaaaagaagt    780
aaaaacgatt ttttgtttgc tgtaacttct gctttataac tggagtaaac tattcttctg    840
tatacgaaaa aaaaaaaaaa aaaa                                             864
```

<210> SEQ ID NO 2
<211> LENGTH: 222
<212> TYPE: PRT
<213> ORGANISM: Cerianthus sp.
<220> FEATURE:
<223> OTHER INFORMATION: Orange fluorescent protein (OFP)

<400> SEQUENCE: 2

Met Asn Leu Ser Lys Asn Val Ser Val Ser Val Tyr Met Lys Gly Asn
  1               5                  10                  15

Val Asn Asn His Glu Phe Glu Tyr Asp Gly Glu Gly Gly Asp Pro
                 20                  25                  30

Tyr Thr Gly Lys Tyr Ser Met Lys Met Thr Leu Arg Gly Gln Asn Cys
             35                  40                  45

Leu Pro Phe Ser Tyr Asp Ile Ile Thr Thr Ala Phe Gln Tyr Gly Phe
         50                  55                  60

Arg Val Phe Thr Lys Tyr Pro Glu Gly Ile Val Asp Tyr Phe Lys Asp
 65                  70                  75                  80

Ser Leu Pro Asp Ala Phe Gln Trp Asn Arg Arg Ile Val Phe Glu Asp
                 85                  90                  95

Gly Gly Val Leu Asn Met Ser Ser Asp Ile Thr Tyr Lys Asp Asn Val
            100                 105                 110

Leu His Gly Asp Val Trp Ala Val Gly Val Asn Phe Pro Pro Asn Gly
        115                 120                 125

```
Pro Val Met Lys Asn Glu Ile Val Met Glu Glu Pro Thr Glu Glu Thr
            130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Gly Asn Met Thr Thr Phe Tyr
                165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Thr Ala His Val Ser Asp Leu Pro Lys
    210                 215                 220

<210> SEQ ID NO 3
<211> LENGTH: 20
<212> TYPE: PRT
<213> ORGANISM: Cerianthus sp.
<220> FEATURE:
<223> OTHER INFORMATION: N-terminal protein sequencing determination of
      Cerianthus sp. OFP.

<400> SEQUENCE: 3

Pro Asn Leu Ser Lys Asn Val Ser Val Ser Val Tyr Met Lys Gly Asn
 1               5                   10                  15

Val Asn Asn His
            20

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence:OFP-H1
      guessmer nucleic acid sequence.

<400> SEQUENCE: 4
atgaarggra aygtraacaa cc                                              22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: OFP-H2
      guessmer nucleic acid sequence.

<400> SEQUENCE: 5
atgaarggra aygtraacaa tc                                              22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: OFP-H3
      guessmer nucleic acid sequence.

<400> SEQUENCE: 6
atgaarggra aygtraataa cc                                              22

<210> SEQ ID NO 7
<211> LENGTH: 22
<212> TYPE: DNA
<213> ORGANISM: Artificial Sequence
```

```
<220> FEATURE:
<223> OTHER INFORMATION: Description of Artificial Sequence: OFP-H4
      guessmer nucleic acid sequence.

<400> SEQUENCE: 7
atgaarggra aygtraataa tc                                                  22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: OFP-H5
      guessmer nucleic acid sequence.

<400> SEQUENCE: 8
atgaarggra aygtyaacaa cc                                                  22

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: OFP-H6
      guessmer nucleic acid sequence.

<400> SEQUENCE: 9
atgaarggra aygtyaacaa tc                                                  22

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence: OFP-H7
      guessmer nucleic acid sequence.

<400> SEQUENCE: 10
atgaarggra aygtyaataa cc                                                  22

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: OFP-H8
      guessmer nucleic acid sequence.

<400> SEQUENCE: 11
atgaarggra aygtyaataa tc                                                  22

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: OFP-m13
      forward primer.

<400> SEQUENCE: 12
atgaagggga atgtcaacaa tcat                                                24

<210> SEQ ID NO 13
<211> LENGTH: 24
<212> TYPE: DNA
<213> ORGANISM: Artificial Sequence
<220> FEATURE:
```

<223> OTHER INFORMATION: Description of Artificial Sequence: OFP-STOP
reverse primer

<400> SEQUENCE: 13
ttacttggga agatcactga cgag    24

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: OFP-T58
forward primer.

<400> SEQUENCE: 14
acggcatttc agtatggttt ccgcgta    27

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: OFP-M131
reverse primer.

<400> SEQUENCE: 15
catcactggc ccattcggcg ggaagtt    27

<210> SEQ ID NO 16
<211> LENGTH: 54
<212> TYPE: DNA
<213> ORGANISM: Artificial Sequence
<220> FEATURE:
<223> OTHER INFORMATION: Description of Artificial Sequence: Invitrogen
Gene Race (tm) Oligo-dt primer.

<400> SEQUENCE: 16
gctgtcaacg atacgctacg taacggcatg acagtgtttt ttttttttt tttt    54

<210> SEQ ID NO 17
<211> LENGTH: 222
<212> TYPE: PRT
<213> ORGANISM: Artificial Sequence
<220> FEATURE:
<223> OTHER INFORMATION: Description of Artificial Sequence:OFP mutant
S8T

<400> SEQUENCE: 17

Met Asn Leu Ser Lys Asn Val Thr Val Ser Val Tyr Met Lys Gly Asn
 1               5                  10                  15

Val Asn Asn His Glu Phe Glu Tyr Asp Gly Glu Gly Gly Gly Asp Pro
            20                  25                  30

Tyr Thr Gly Lys Tyr Ser Met Lys Met Thr Leu Arg Gly Gln Asn Cys
        35                  40                  45

Leu Pro Phe Ser Tyr Asp Ile Ile Thr Thr Ala Phe Gln Tyr Gly Phe
    50                  55                  60

Arg Val Phe Thr Lys Tyr Pro Glu Gly Ile Val Asp Tyr Phe Lys Asp
65                  70                  75                  80

Ser Leu Pro Asp Ala Phe Gln Trp Asn Arg Arg Ile Val Phe Glu Asp
                85                  90                  95

Gly Gly Val Leu Asn Met Ser Ser Asp Ile Thr Tyr Lys Asp Asn Val
            100                 105                 110

Leu His Gly Asp Val Trp Ala Val Gly Val Asn Phe Pro Pro Asn Gly

```
                115                 120                 125
Pro Val Met Lys Asn Glu Ile Val Met Glu Glu Pro Thr Glu Glu Thr
    130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Tyr Gly Asn Met Thr Thr Phe Tyr
                165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Thr Ala His Val Ser Asp Leu Pro Lys
    210                 215                 220

<210> SEQ ID NO 18
<211> LENGTH: 222
<212> TYPE: PRT
<213> ORGANISM: Artificial Sequence
<220> FEATURE:
<223> OTHER INFORMATION: Description of Artificial Sequence: OFP mutant
      V120I.

<400> SEQUENCE: 18

Met Asn Leu Ser Lys Asn Val Ser Val Ser Val Tyr Met Lys Gly Asn
1               5                   10                  15

Val Asn Asn His Glu Phe Glu Tyr Asp Gly Glu Gly Gly Gly Asp Pro
            20                  25                  30

Tyr Thr Gly Lys Tyr Ser Met Lys Met Thr Leu Arg Gly Gln Asn Cys
        35                  40                  45

Leu Pro Phe Ser Tyr Asp Ile Ile Thr Thr Ala Phe Gln Tyr Gly Phe
    50                  55                  60

Arg Val Phe Thr Lys Tyr Pro Glu Gly Ile Val Asp Tyr Phe Lys Asp
65                  70                  75                  80

Ser Leu Pro Asp Ala Phe Gln Trp Asn Arg Arg Ile Val Phe Glu Asp
                85                  90                  95

Gly Gly Val Leu Asn Met Ser Ser Asp Ile Thr Tyr Lys Asp Asn Val
            100                 105                 110

Leu His Gly Asp Val Trp Ala Ile Gly Val Asn Phe Pro Pro Asn Gly
        115                 120                 125

Pro Val Met Lys Asn Glu Ile Val Met Glu Glu Pro Thr Glu Glu Thr
    130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Tyr Gly Asn Met Thr Thr Phe Tyr
                165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Thr Ala His Val Ser Asp Leu Pro Lys
    210                 215                 220

<210> SEQ ID NO 19
<211> LENGTH: 222
<212> TYPE: PRT
<213> ORGANISM: Artificial Sequence
<220> FEATURE:
```

-continued

<223> OTHER INFORMATION: Description of Artificial Sequence: OFP mutant
     A159V

<400> SEQUENCE: 19

Met Asn Leu Ser Lys Asn Val Ser Val Ser Val Tyr Met Lys Gly Asn
1               5                   10                  15

Val Asn Asn His Glu Phe Glu Tyr Asp Gly Glu Gly Gly Gly Asp Pro
            20                  25                  30

Tyr Thr Gly Lys Tyr Ser Met Lys Met Thr Leu Arg Gly Gln Asn Cys
        35                  40                  45

Leu Pro Phe Ser Tyr Asp Ile Ile Thr Thr Ala Phe Gln Tyr Gly Phe
    50                  55                  60

Arg Val Phe Thr Lys Tyr Pro Glu Gly Ile Val Asp Tyr Phe Lys Asp
65                  70                  75                  80

Ser Leu Pro Asp Ala Phe Gln Trp Asn Arg Arg Ile Val Phe Glu Asp
                85                  90                  95

Gly Gly Val Leu Asn Met Ser Ser Asp Ile Thr Tyr Lys Asp Asn Val
            100                 105                 110

Leu His Gly Asp Val Trp Ala Val Gly Val Asn Phe Pro Pro Asn Gly
        115                 120                 125

Pro Val Met Lys Asn Glu Ile Val Met Glu Glu Pro Thr Glu Glu Thr
    130                 135                 140

Phe Thr Pro Lys Asn Gly Val Leu Val Gly Phe Cys Pro Lys Val Tyr
145                 150                 155                 160

Leu Leu Lys Asp Gly Ser Tyr Tyr Gly Asn Met Thr Thr Phe Tyr
                165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Thr Ala His Val Ser Asp Leu Pro Lys
    210                 215                 220

<210> SEQ ID NO 20
<211> LENGTH: 222
<212> TYPE: PRT
<213> ORGANISM: Artificial Sequence
<220> FEATURE:
<223> OTHER INFORMATION: Description of Artificial Sequence: OFP mutant
     N171Q

<400> SEQUENCE: 20

Met Asn Leu Ser Lys Asn Val Ser Val Ser Val Tyr Met Lys Gly Asn
1               5                   10                  15

Val Asn Asn His Glu Phe Glu Tyr Asp Gly Glu Gly Gly Gly Asp Pro
            20                  25                  30

Tyr Thr Gly Lys Tyr Ser Met Lys Met Thr Leu Arg Gly Gln Asn Cys
        35                  40                  45

Leu Pro Phe Ser Tyr Asp Ile Ile Thr Thr Ala Phe Gln Tyr Gly Phe
    50                  55                  60

Arg Val Phe Thr Lys Tyr Pro Glu Gly Ile Val Asp Tyr Phe Lys Asp
65                  70                  75                  80

Ser Leu Pro Asp Ala Phe Gln Trp Asn Arg Arg Ile Val Phe Glu Asp
                85                  90                  95

Gly Gly Val Leu Asn Met Ser Ser Asp Ile Thr Tyr Lys Asp Asn Val
            100                 105                 110

-continued

Leu His Gly Asp Val Trp Ala Val Gly Val Asn Phe Pro Pro Asn Gly
        115                 120                 125

Pro Val Met Lys Asn Glu Ile Val Met Glu Pro Thr Glu Glu Thr
130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Gly Gln Met Thr Thr Phe Tyr
            165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Thr Ala His Val Ser Asp Leu Pro Lys
        210                 215                 220

<210> SEQ ID NO 21
<211> LENGTH: 222
<212> TYPE: PRT
<213> ORGANISM: Artificial Sequence
<220> FEATURE:
<223> OTHER INFORMATION: Description of Artificial Sequence: OFP mutant
      T214S

<400> SEQUENCE: 21

Met Asn Leu Ser Lys Asn Val Ser Val Ser Val Tyr Met Lys Gly Asn
1               5                   10                  15

Val Asn Asn His Glu Phe Glu Tyr Asp Gly Glu Gly Gly Gly Asp Pro
            20                  25                  30

Tyr Thr Gly Lys Tyr Ser Met Lys Met Thr Leu Arg Gly Gln Asn Cys
        35                  40                  45

Leu Pro Phe Ser Tyr Asp Ile Ile Thr Thr Ala Phe Gln Tyr Gly Phe
    50                  55                  60

Arg Val Phe Thr Lys Tyr Pro Glu Gly Ile Val Asp Tyr Phe Lys Asp
65                  70                  75                  80

Ser Leu Pro Asp Ala Phe Gln Trp Asn Arg Arg Ile Val Phe Glu Asp
                85                  90                  95

Gly Gly Val Leu Asn Met Ser Ser Asp Ile Thr Tyr Lys Asp Asn Val
            100                 105                 110

Leu His Gly Asp Val Trp Ala Val Gly Val Asn Phe Pro Pro Asn Gly
        115                 120                 125

Pro Val Met Lys Asn Glu Ile Val Met Glu Pro Thr Glu Glu Thr
130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Gly Asn Met Thr Thr Phe Tyr
            165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Ser Ala His Val Ser Asp Leu Pro Lys
        210                 215                 220

<210> SEQ ID NO 22
<211> LENGTH: 222
<212> TYPE: PRT
<213> ORGANISM: Artificial Sequence
<220> FEATURE:
<223> OTHER INFORMATION: Description of Artificial Sequence: OFP green flourescent mutant Y37F

<400> SEQUENCE: 22

```
Met Asn Leu Ser Lys Asn Val Ser Val Ser Val Tyr Met Lys Gly Asn
 1               5                  10                  15

Val Asn Asn His Glu Phe Glu Tyr Asp Gly Glu Gly Gly Gly Asp Pro
            20                  25                  30

Tyr Thr Gly Lys Phe Ser Met Lys Met Thr Leu Arg Gly Gln Asn Cys
        35                  40                  45

Leu Pro Phe Ser Tyr Asp Ile Ile Thr Thr Ala Phe Gln Tyr Gly Phe
 50                  55                  60

Arg Val Phe Thr Lys Tyr Pro Glu Gly Ile Val Asp Tyr Phe Lys Asp
 65                  70                  75                  80

Ser Leu Pro Asp Ala Phe Gln Trp Asn Arg Arg Ile Val Phe Glu Asp
                85                  90                  95

Gly Gly Val Leu Asn Met Ser Ser Asp Ile Thr Tyr Lys Asp Asn Val
            100                 105                 110

Leu His Gly Asp Val Trp Ala Val Gly Val Asn Phe Pro Pro Asn Gly
        115                 120                 125

Pro Val Met Lys Asn Glu Ile Val Met Glu Glu Pro Thr Glu Glu Thr
130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Tyr Gly Asn Met Thr Thr Phe Tyr
                165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Thr Ala His Val Ser Asp Leu Pro Lys
210                 215                 220
```

<210> SEQ ID NO 23
<211> LENGTH: 33
<212> TYPE: DNA
<213> ORGANISM: Artificial Sequence
<220> FEATURE:
<223> OTHER INFORMATION: Description of Artificial Sequence: OFP-Y37F-F forward primer

<400> SEQUENCE: 23
ccttatacag gtaaattttc catgaagatg acg                          33

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: OFP-Y37F-R reverse primer

<400> SEQUENCE: 24
cgtcatcttc atggaaaatt tacctgtata agg                          33

<210> SEQ ID NO 25
<211> LENGTH: 45
<212> TYPE: DNA
<213> ORGANISM: Artificial Sequence

```
<220> FEATURE:
<223> OTHER INFORMATION: Description of Artificial Sequence: GFP to OFP
      forward primer

<400> SEQUENCE: 25
acacttgtca ctactttcca gtatggtttt caatgctttt caaga              45

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: GFP to OFP
      reverse primer.

<400> SEQUENCE: 26
tcttgaaaag cattgaaaac catactggaa agtagtgaca agtgt              45

<210> SEQ ID NO 27
<211> LENGTH: 222
<212> TYPE: PRT
<213> ORGANISM: Artificial Sequence
<220> FEATURE:
<223> OTHER INFORMATION: Description of Artificial Sequence: OFP mutant
      C48S

<400> SEQUENCE: 27
```

Met Asn Leu Ser Lys Asn Val Ser Val Ser Val Tyr Met Lys Gly Asn
 1               5                  10                  15

Val Asn Asn His Glu Phe Glu Tyr Asp Gly Glu Gly Gly Gly Asp Pro
            20                  25                  30

Tyr Thr Gly Lys Tyr Ser Met Lys Met Thr Leu Arg Gly Gln Asn Ser
        35                  40                  45

Leu Pro Phe Ser Tyr Asp Ile Ile Thr Thr Ala Phe Gln Tyr Gly Phe
    50                  55                  60

Arg Val Phe Thr Lys Tyr Pro Glu Gly Ile Val Asp Tyr Phe Lys Asp
65                  70                  75                  80

Ser Leu Pro Asp Ala Phe Gln Trp Asn Arg Arg Ile Val Phe Glu Asp
                85                  90                  95

Gly Gly Val Leu Asn Met Ser Ser Asp Ile Thr Tyr Lys Asp Asn Val
            100                 105                 110

Leu His Gly Asp Val Trp Ala Val Gly Val Asn Phe Pro Pro Asn Gly
        115                 120                 125

Pro Val Met Lys Asn Glu Ile Val Met Glu Glu Pro Thr Glu Glu Thr
    130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Tyr Gly Asn Met Thr Thr Phe Tyr
                165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Thr Ala His Val Ser Asp Leu Pro Lys
    210                 215                 220

```
<210> SEQ ID NO 28
<211> LENGTH: 222
<212> TYPE: PRT
<213> ORGANISM: Artificial Sequence
```

-continued

```
<220> FEATURE:
<223> OTHER INFORMATION: Description of Artificial Sequence: OFP
      golden-yellow fluotescent mutant Q61S

<400> SEQUENCE: 28

Met Asn Leu Ser Lys Asn Val Ser Val Ser Val Tyr Met Lys Gly Asn
 1               5                  10                  15

Val Asn Asn His Glu Phe Glu Tyr Asp Gly Glu Gly Gly Asp Pro
             20                  25                  30

Tyr Thr Gly Lys Tyr Ser Met Lys Met Thr Leu Arg Gly Gln Asn Cys
         35                  40                  45

Leu Pro Phe Ser Tyr Asp Ile Ile Thr Thr Ala Phe Ser Tyr Gly Phe
     50                  55                  60

Arg Val Phe Thr Lys Tyr Pro Glu Gly Ile Val Asp Tyr Phe Lys Asp
 65                  70                  75                  80

Ser Leu Pro Asp Ala Phe Gln Trp Asn Arg Arg Ile Val Phe Glu Asp
                 85                  90                  95

Gly Gly Val Leu Asn Met Ser Ser Asp Ile Thr Tyr Lys Asp Asn Val
            100                 105                 110

Leu His Gly Asp Val Trp Ala Val Gly Val Asn Phe Pro Pro Asn Gly
            115                 120                 125

Pro Val Met Lys Asn Glu Ile Val Met Glu Glu Pro Thr Glu Glu Thr
        130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Tyr Gly Asn Met Thr Thr Phe Tyr
                165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Thr Ala His Val Ser Asp Leu Pro Lys
    210                 215                 220

<210> SEQ ID NO 29
<211> LENGTH: 222
<212> TYPE: PRT
<213> ORGANISM: Artificial Sequence
<220> FEATURE:
<223> OTHER INFORMATION: Description of Artificial Sequence: OFP magenta
      fluorescent mutant K79R.

<400> SEQUENCE: 29

Met Asn Leu Ser Lys Asn Val Ser Val Ser Val Tyr Met Lys Gly Asn
 1               5                  10                  15

Val Asn Asn His Glu Phe Glu Tyr Asp Gly Glu Gly Gly Asp Pro
             20                  25                  30

Tyr Thr Gly Lys Tyr Ser Met Lys Met Thr Leu Arg Gly Gln Asn Cys
         35                  40                  45

Leu Pro Phe Ser Tyr Asp Ile Ile Thr Thr Ala Phe Gln Tyr Gly Phe
     50                  55                  60

Arg Val Phe Thr Lys Tyr Pro Glu Gly Ile Val Asp Tyr Phe Arg Asp
 65                  70                  75                  80

Ser Leu Pro Asp Ala Phe Gln Trp Asn Arg Arg Ile Val Phe Glu Asp
                 85                  90                  95

Gly Gly Val Leu Asn Met Ser Ser Asp Ile Thr Tyr Lys Asp Asn Val
            100                 105                 110
```

```
Leu His Gly Asp Val Trp Ala Val Gly Val Asn Phe Pro Pro Asn Gly
        115                 120                 125

Pro Val Met Lys Asn Glu Ile Val Met Glu Glu Pro Thr Glu Glu Thr
        130                 135                 140

Phe Thr Pro Lys Asn Gly Val Leu Val Gly Phe Cys Pro Lys Ala Tyr
145                 150                 155                 160

Leu Leu Lys Asp Gly Ser Tyr Tyr Tyr Gly Asn Met Thr Thr Phe Tyr
                165                 170                 175

Arg Ser Lys Lys Ser Gly Gln Ala Pro Pro Gly Tyr His Phe Val Lys
            180                 185                 190

His Arg Leu Val Lys Thr Asn Val Gly His Gly Phe Lys Thr Val Glu
        195                 200                 205

Gln Thr Glu Tyr Ala Thr Ala His Val Ser Asp Leu Pro Lys
    210                 215                 220

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Chromophore
      pentapeptide capable of fluorescing.

<400> SEQUENCE: 30

Phe Gln Tyr Gly Phe
1               5

<210> SEQ ID NO 31
<211> LENGTH: 265
<212> TYPE: PRT
<213> ORGANISM: Artificial Sequence
<220> FEATURE:
<223> OTHER INFORMATION: Description of Artificial Sequence: Green
      fluororescent protein  CFP484.

<400> SEQUENCE: 31

Met Lys Cys Lys Phe Val Phe Cys Leu Ser Phe Leu Val Leu Ala Ile
1               5                   10                  15

Thr Asn Ala Asn Ile Phe Leu Arg Asn Glu Ala Asp Leu Glu Glu Lys
            20                  25                  30

Thr Leu Arg Ile Pro Lys Ala Leu Thr Thr Met Gly Val Ile Lys Pro
        35                  40                  45

Asp Met Lys Ile Lys Leu Lys Met Glu Gly Asn Val Asn Gly His Ala
    50                  55                  60

Phe Val Ile Glu Gly Glu Gly Glu Gly Lys Pro Tyr Asp Gly Thr His
65                  70                  75                  80

Thr Leu Asn Leu Glu Val Lys Glu Gly Ala Pro Leu Pro Phe Ser Tyr
                85                  90                  95

Asp Ile Leu Ser Asn Ala Phe Gln Tyr Gly Asn Arg Ala Leu Thr Lys
            100                 105                 110

Tyr Pro Asp Asp Ile Ala Asp Tyr Phe Gln Lys Ser Phe Pro Glu Gly
        115                 120                 125

Tyr Ser Trp Glu Arg Thr Met Thr Phe Glu Asp Lys Gly Ile Val Lys
    130                 135                 140

Val Lys Ser Asp Ile Ser Met Glu Glu Asp Ser Phe Ile Tyr Glu Ile
145                 150                 155                 160

Arg Phe Asp Gly Met Asn Phe Pro Pro Asn Gly Pro Val Met Gln Lys
                165                 170                 175
```

```
Lys Thr Leu Lys Trp Glu Pro Ser Thr Glu Ile Met Tyr Val Arg Asp
            180                 185                 190
Gly Val Leu Val Gly Asp Ile Ser His Ser Leu Leu Glu Gly Gly
        195                 200                 205
His Tyr Arg Cys Asp Phe Lys Ser Ile Tyr Lys Ala Lys Lys Val Val
            210                 215                 220
Lys Leu Pro Asp Tyr His Phe Val Asp His Arg Ile Glu Ile Leu Asn
225                 230                 235                 240
His Asp Lys Asp Tyr Asn Lys Val Thr Leu Tyr Glu Asn Ala Val Ala
                245                 250                 255
Arg Tyr Ser Leu Leu Pro Ser Gln Ala
                260                 265

<210> SEQ ID NO 32
<211> LENGTH: 225
<212> TYPE: PRT
<213> ORGANISM: Artificial Sequence
<220> FEATURE:
<223> OTHER INFORMATION: Description of Artificial Sequence:
      Spontaneously fluororescent protein DsRed.

<400> SEQUENCE: 32

Met Arg Ser Ser Lys Asn Val Ile Lys Glu Phe Met Arg Phe Lys Val
  1               5                  10                  15
Arg Met Glu Gly Thr Val Asn Gly His Glu Phe Glu Ile Glu Gly Glu
             20                  25                  30
Gly Glu Gly Arg Pro Tyr Glu Gly His Asn Thr Val Lys Leu Lys Val
         35                  40                  45
Thr Lys Gly Gly Pro Leu Pro Phe Ala Trp Asp Ile Leu Ser Pro Gln
 50                  55                  60
Phe Gln Tyr Gly Ser Lys Val Tyr Val Lys His Pro Ala Asp Ile Pro
 65                  70                  75                  80
Asp Tyr Lys Lys Leu Ser Phe Pro Glu Gly Phe Lys Trp Glu Arg Val
                 85                  90                  95
Met Asn Phe Glu Asp Gly Gly Val Val Thr Val Thr Gln Asp Ser Ser
            100                 105                 110
Leu Gln Asp Gly Cys Phe Ile Tyr Lys Val Lys Phe Ile Gly Val Asn
        115                 120                 125
Phe Pro Ser Asp Gly Pro Val Met Gln Lys Lys Thr Met Gly Trp Glu
    130                 135                 140
Ala Ser Thr Glu Arg Leu Tyr Pro Arg Asp Gly Val Leu Lys Gly Glu
145                 150                 155                 160
Ile His Lys Ala Leu Lys Leu Lys Asp Gly Gly His Tyr Leu Val Glu
                165                 170                 175
Phe Lys Ser Ile Tyr Met Ala Lys Lys Pro Val Gln Leu Pro Gly Tyr
            180                 185                 190
Tyr Tyr Val Asp Ser Lys Leu Asp Ile Thr Ser His Asn Glu Asp Tyr
        195                 200                 205
Thr Ile Val Glu Gln Tyr Glu Arg Thr Glu Gly Arg His His Leu Phe
    210                 215                 220
Leu
225
```